Figure 1A:
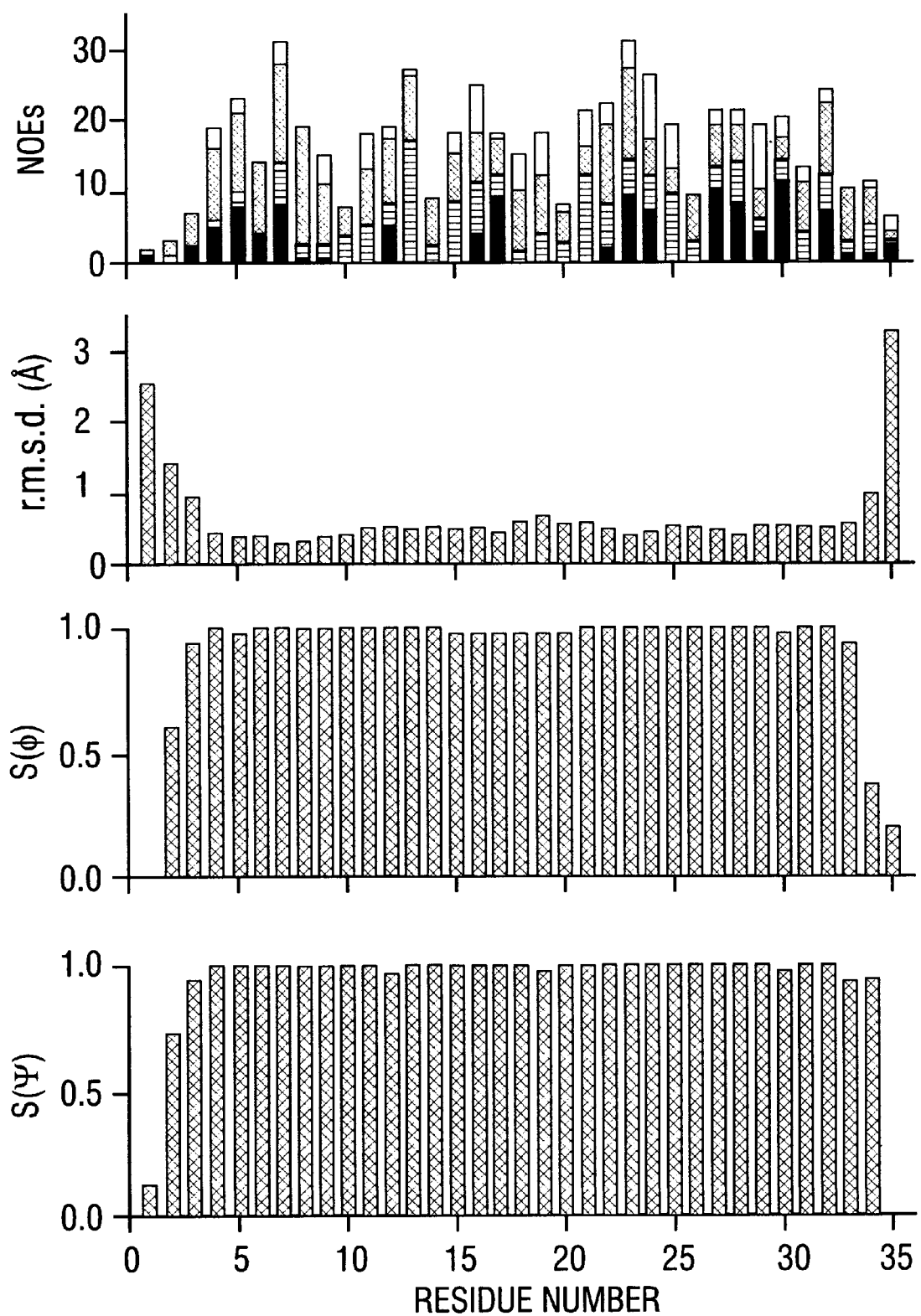

US006077680A

United States Patent [19]
Kem et al.

[11] Patent Number: 6,077,680
[45] Date of Patent: Jun. 20, 2000

[54] SHK TOXIN COMPOSITIONS AND METHODS OF USE

[75] Inventors: William R. Kem, Gainesville, Fla.; Michael W. Pennington, Cherry Hill, N.J.; Raymond S. Norton, Ivanhoe, Australia; K. George Chandy, Laguna Beach; Katalin Kalman, Irvine, both of Calif.

[73] Assignees: The University of Florida, Gainesville, Fla.; Bachem Bioscience, Ing., King of Prussia, Pa.; Biomolecular Research Institute, Parkville, Australia; Regents of the University of California, Oakland, Calif.

[21] Appl. No.: 08/980,858

[22] Filed: Nov. 26, 1997

Related U.S. Application Data

[60] Provisional application No. 60/059,126, Sep. 17, 1997, and provisional application No. 60/031,860, Nov. 27, 1996.

[51] Int. Cl.[7] .................. G01N 33/566; A61K 38/17; C07K 14/435; A01N 37/20
[52] U.S. Cl. .................. 435/7.24; 514/12; 514/9; 514/2; 424/185.1; 530/300; 530/324; 530/855
[58] Field of Search .................. 514/12, 2, 9; 530/300, 530/324, 855; 424/185.1; 435/7.24

[56] References Cited

U.S. PATENT DOCUMENTS

| | | | |
|---|---|---|---|
| 4,196,265 | 4/1980 | Koprowski et al. | 435/70.21 |
| 4,554,101 | 11/1985 | Hopp | 530/324 |
| 4,683,195 | 7/1987 | Mullis et al. | 435/6 |
| 4,683,202 | 7/1987 | Mullis | 435/91.2 |
| 4,757,011 | 7/1988 | Chaleff et al. | 800/276 |
| 4,769,061 | 9/1988 | Comai | 504/206 |
| 4,940,835 | 7/1990 | Shah et al. | 800/288 |
| 4,965,188 | 10/1990 | Mullis et al. | 435/6 |
| 4,971,908 | 11/1990 | Kishore et al. | 536/23.2 |
| 5,176,995 | 1/1993 | Sninsky et al. | 435/6 |
| 5,494,895 | 2/1996 | Garcia et al. | 514/12 |
| 5,763,478 | 6/1998 | Baker et al. | 514/450 |

FOREIGN PATENT DOCUMENTS

| | | |
|---|---|---|
| 0219716 | 4/1987 | European Pat. Off. . |
| WO 88/06451 | 9/1988 | WIPO . |

OTHER PUBLICATIONS

Lin et al. Voltage–gated potassium channels regulate Calcium–dependent Pathways involed in Human T Lymphocyte Activation. J. Exp. Med. 177: 637–645, Mar. 1993.

Bowie et al. Deciphering the message in protein sequences: tolerance to amino acid substitutions. Science, vol. 247, pp. 1306–1310, Mar. 16, 1990.

Wells, JA. Additivity of mutational effects in proteins. Biochemistry 29(37):8509–8516, Sep. 18, 1990.

Pennington et al., "Identification of essential residues in the potassium channel inhibitor ShK toxins: Analysis of mono-subsitiuted analogs," *Peptides: Chemistry, Structure and Biology—Proceedings of the 14th American Peptide Symposium*, pp. 192–194, 1996.

Tudor et al., "Solution structure of ShK toxin, a novel potassium channel inhibitor from a sea anemone," *Nature Structural Biology*, 3(4):317–320, 1996.

(List continued on next page.)

*Primary Examiner*—Karen Cochrane Carlson
*Assistant Examiner*—Gabriele E. Bugaisky
*Attorney, Agent, or Firm*—Williams, Morgan, & Amerson

[57] ABSTRACT

Disclosed are methods and compositions comprising DNA segments, and proteins derived from sea anemone species. More particularly, it concerns the novel ShK toxin, ShK toxin analogs, chemically-modified toxin analogs, and nucleic acid segments encoding the ShK toxin from *Stichodactyla helianthus*. Various methods for making and using these DNA segments, DNA segments encoding synthetically-modified ShK toxins, and native and synthetic ShK peptides are disclosed, such as, for example, the use of DNA segments as diagnostic probes and templates for protein production, and the use of proteins, fusion protein carriers and peptides in various immunological and diagnostic applications.

42 Claims, 25 Drawing Sheets

R-S-$C^3$-I-D-T-I-P-K-S-R-$C^{12}$-T-A-F-Q-$C^{17}$-K-H-S-M-K-Y-R-L-S-F-$C^{28}$-R-K-T-$C^{32}$-G-T-$C^{35}$

OTHER PUBLICATIONS

Bednarek, Bugianesi, Leonard, Felix, "Chemical synthesis and structure–function studies of margatoxin, a potent inhibitor of voltage–dependent potassium channel in human T lymphocytes," *Biochem. Biophys. Res. Comm.*, 198:619–625, 1994.

Benedetti et al., "Intrasplenic hepatocyte allotransplantation in Dalmatian dogs with and without cyclosporine immunosuppression," *Transplantation*, 63(9):1206–1209, May 1997.

Benelli et al., "FK–506 delays corneal graft rejection in a model of corneal xenotransplantation," *J. Ocular Pharmacology and Therapeutics*, 12(4):425–431, 1996.

Bouchard et al., "The role of systemic cyclosporine dosing schedule on corneal allograft survival in the rat model," *Curr. Eye Res.*, 14(5):421–424, 1995.

Bullard et al., "A polygenic mouse model of psoriasiform skin disease in CD18–deficient mice," *Proc. Natl. Acad. Sci. USA*, 93:2116–2121, Mar. 1996.

Escobar, Root, MacKinnon, "Influence of protein surface charge on the bimolecular kinetics of a potassium channel peptide inhibitor," *Biochem.*, 32:6982–6987, 1993.

Fujihara et al., "Establishment of a rabbit short–term dry eye model," *J. Ocular Pharmacology and Therapeutics*, 11(4):503–508, 1995.

Granger et al., "Prolongation of renal allograft survival in a large animal model by oral rapamycin monotherapy," *Transplantation*, 59(2):183–186, Jan. 1995.

Kem, Parten, Pennington, Dunn, Price, "Isolation, characterization and amino acid sequence of a polypeptide neurotoxin occurring in the sea anemone *Stichodactyla helianthus*," *Biochem.*, 28:3483–3489, 1989.

Leach et al., "Inflammatory bowel disease in C.B–17 scid mice reconstituted with the CD45RB[high] subset of CD4[+] T cells," *Amer. J. of Path.*, 148(5):11503–1515, May 1996.

Leonard, Garcia, Slaughter, Reuben, "Selective blockers of voltage–gate K+ channels depolarize human T–lymphocytes: Mechanism of the antiproliferative effect of charybdotoxin," *Proc. Natl. Acad. Sci. USA*, 89:10094–10098, 1992.

Lewis and Cahalan, "Potassium and calcium channels in lymphocytes," *Ann. Rev. Immunol.*, 13:623–653, 1995.

Massacesi et al., "Active and passively induced experimental autoimmune encephalomyelitis in common marmosets: a new model for multiple sclerosis," *Annals of Neurology*, 37(4):519–530, Apr. 1995.

Nguyen et al., "Novel nonpeptide agents potently block the C–type inactivated conformation of Kv1.3 and suppress T cell activation," *Mol. Pharmacol*, 50(6):1672–1679, 1996.

Pennington et al., "An Essential Binding Surface for SkH Toxin Interaction with Rat Brain Potassium Channels," *Biochem.*, 35(51):16407–16411, 1996.

Pennington et al., "Chemical synthesis and characterization of ShK toxin; a potent potassium channel inhibitor from a sea anemone," *Int. J. Peptide Res.*, 46:354–358, 1995.

Pennington, Kem, Dunn, "Synthesis and biological activity of six monosubstituted analogs of a sea anemone polypeptide neurotoxin," *Peptide Res.*, 3:228–232, 1990.

Pennington, Mahnir, Baur, MacVaugh, Behm, Kem, "The effect of truncation on SHK toxin: elimination of the amino–carboxyl terminal (3–35) disulfide linkage stabilizing the amino and carboxyl terminal segments," *Protein and Peptide Letters*, 4(4):237–242, 1997.

Pennington, Mahnir, Krafte, Zaydenberg, Byrnes, Khaytin, Crowley, Kem, "Identification of three separate binding sites on SHK toxin, a potent inhibitor of voltage–dependent potassium channels in human T–lymphocytes and rat brain," *Biochem. Biophys, Res. Comm.*, 219:696–701, 1996.

Pohl, Hubalek, Byrnes, Nielsen, Woods, Pennington, "Assignment of the three disulfide bonds in Shk toxin: a potent potassium channel inhibitor from the sea anemone *Stichodactyla helianthus*," *Letter in Peptide Sci.*, 1:291–297, 1995.

Rothschild et al., "Naturally occurring inflammatory arthritis of the spondyloarthropathy variety in Cayo Santiago rhesus macques (Macaca mulatta)," *Clin. & Experimental Rheumatology*, 15(1):45–51, 1997.

Salgado and Kem, "Actions of three structurally distinct sea anemone toxins on crustacean and insect sodium channels," *Toxicon*, 30(11):1365–1381, 1992.

Schmid et al., "A chronic large animal model of lung allograft rejection," *Transplantaion Proceedings*, 29:1521, 1997.

Scott, Muniz, Sewing, Lichtinghagen, Parcej, Pongs, Dolly, "Antibodies specific for distinct Kv subunits unveil a hetero–oligomeric basis for subtypes of alpha–dendrotoxin–sensitive K+ channels in bovine brain," *Biochem.*, 33(7):1617–1623, 1994.

Tanabe et al., "Effect of deoxyspergualin on vascular rejection in canine kidney transplation," *J. of Urology*, 152:562–566, 1994.

ShK  ChTx  AgTx2

```
           10              20            30
RSCIDTIPKS R CTAFQ- - - - -C KHSMKYRLSF CRKTCGTC    ShK
-VCRDWFKETA CRHAKSLGNC RTSQKYRAN-C AKTLQCC         BgK
```

FIG. 3

ShK TOXIN

R-S-C$_3$-I-D-T-I-P-K-S-R-C$_{12}$-T-A-F-Q-C$_{17}$-K-H-S-M-K-Y-R-L-S-F-C$_{28}$-R-K-T-C$_{32}$-G-T-C$_{35}$ with disulfide bonds: C$_3$–C$_{35}$, C$_{12}$–C$_{28}$, C$_{17}$–C$_{32}$

Monocyclic

K S R C T A F Q C K H S (Nle) K Y R L S F C R K T C (bond between the two internal C residues)

Dicyclic

K S R C T A F Q C K H S (Nle) K Y R L S F C R K T C (two disulfide bonds)

FIG. 20

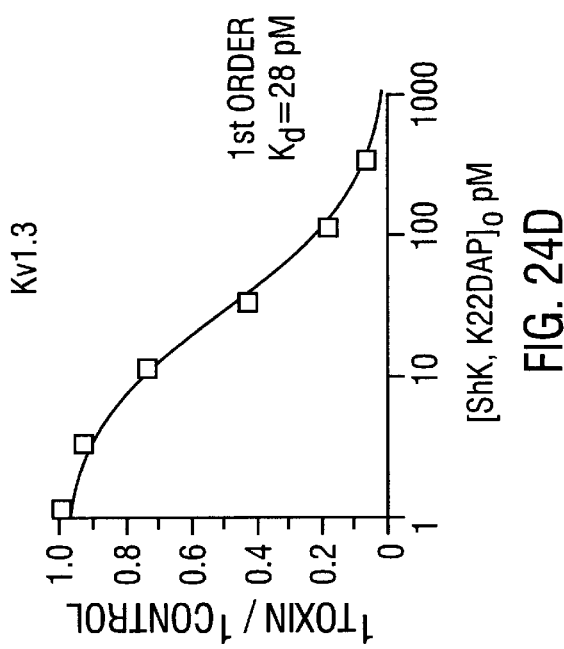
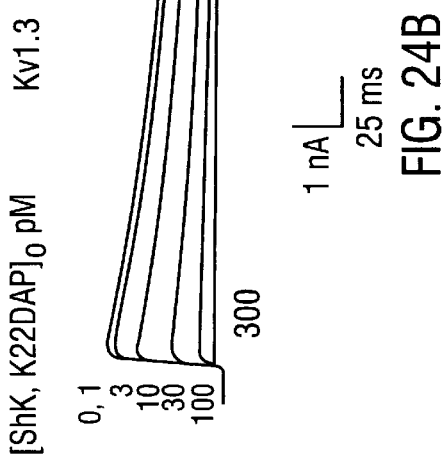
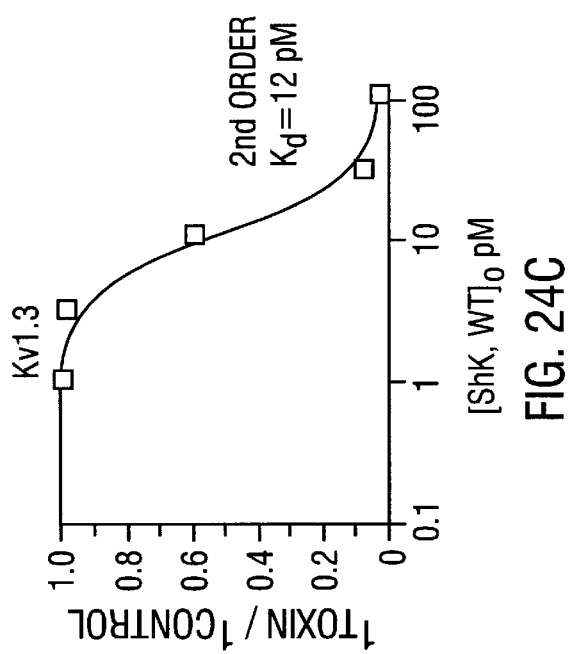
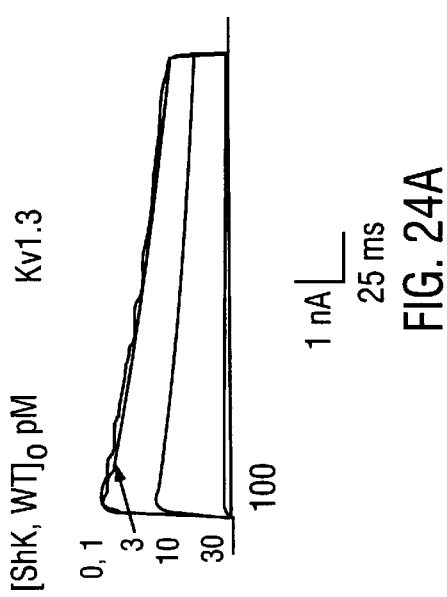

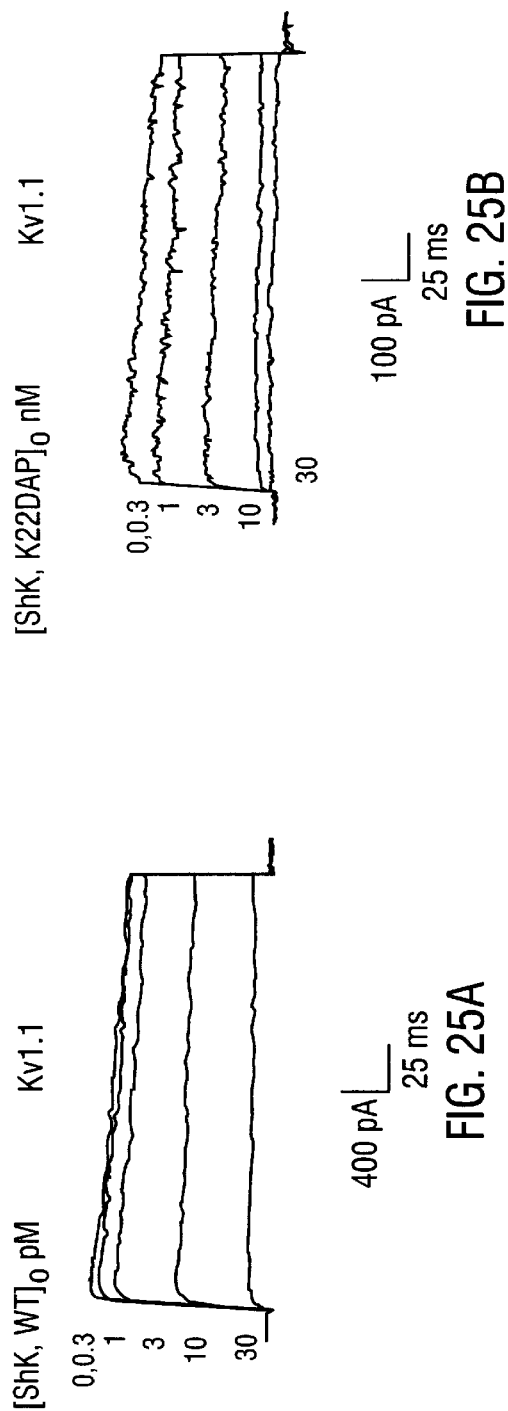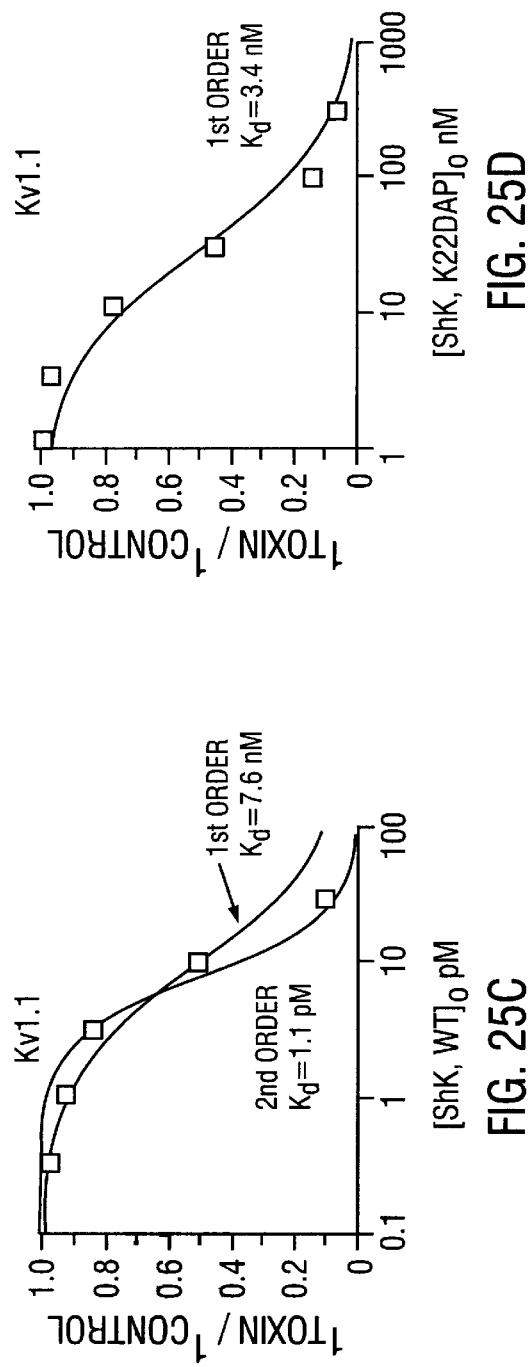
FIG. 25A, FIG. 25B, FIG. 25C, FIG. 25D

SHK TOXIN COMPOSITIONS AND METHODS OF USE

The present application is a continuing application of U.S. Provisional Serial No. 60/059,126, filed Sep.17, 1997, which was a continuing application of U.S. Provisional Serial No. 60/031,860, filed Nov. 27, 1996, the contents of which are specifically incorporated herein in their entirety.

The United States government has rights in the present invention pursuant to Grant RO1-GM-54221 from the National Institutes of Health.

BACKGROUND OF THE INVENTION

1.1 Field of the Invention

The present invention relates generally to the fields of molecular biology. Disclosed are methods and compositions comprising DNA segments, and proteins derived from sea anemone species. More particularly, it concerns novel ShK toxin, toxin analogs, modified toxin analogs, and genes encoding the ShK toxin from *Stichodactyla helianthus*. Various methods for making and using these DNA segments, DNA segments encoding synthetically-modified ShK toxins, and native and synthetic ShK peptides are disclosed, such as, for example, the use of DNA segments as diagnostic probes; and templates for protein production, and the use of proteins, fusion protein carriers and peptides in various immunological and diagnostic applications.

1.2 Description of Related Art

A multitude of potassium (K) channels have been discovered in the past decade. The synergistic interplay of molecular biological and electrophysiological approaches has permitted the isolation, individual expression, and functional analysis of many K channels within the past five years. K channels can be conveniently though arbitrarily divided into voltage-gated and chemically-gated types. The voltage-gated channels primarily consist of delayed-rectifiers (DR) and inward-rectifiers. These are primarily important for modulating excitability and determining the rate of repolarization during action potentials. Chemically-gated K channels include ATP-inhibited, Ca-activated, and neurotransmitter-gated channels. These function in the long-term modulation of cell membrane potential, thereby affecting smooth muscle tone, synaptic excitability, neurotransmitter release, and other processes. While many types of K channel are widely distributed in various tissues of the body, one of the delayed-rectifier channels, Kv1.3, is almost exclusively located in T lymphocytes (Cahalan et al., 1991; Lewis and Cahalan, 1995). This lymphocyte K channel has been shown to be homo-oligomeric, in contrast with many DR channels in the nervous and muscular systems, which can exist as hetero-oligomers containing more than one subunit. For instance, in the rat brain, most DR channels are of the Kv1.2 and Kv1.1 types, and these two types of subunits also may be present in the same channel (Scott et al., 1994).

The mechanisms by which Kv1.3 channels affect lymphocyte proliferation are being investigated in several laboratories. The major evidence that they are involved is the ability of ChTx and margatoxin to inhibit lymphocyte proliferation and interleukin 2 production (Chandy et al., 1984; Price et al, 1989; Garcia-Calvo et al., 1993). Inhibition of Kv1.3 depolarizes the cell membrane sufficiently to decrease calcium influx, and this prevents elevation of free intracellular calcium concentration which is the stimulus for these two responses. Other K channel inhibitors such as TEA, 4-aminopyridine, and quinidine also inhibit proliferation, but they often have other effects as well. Other K channels like K(Ca) channels are also present, but their blockade does not inhibit interleukin release or proliferation (Leonard et al., 1992; 1995). The restricted tissue distribution of Kv1.3 and its immunosuppressive action upon T-cells has prompted several pharmaceutical companies to attempt development of specific Kv1.3 blockers for therapeutic use as immunosuppressants. Blockade of other DR K channels in the body is thought to be deleterious to health, with two possible exceptions. The Kv1.5 channel occurring in the myocardium, when blocked, leads to prolongation of the cardiac action potential. So there is interest in developing Kv1.5 channel-selective blockers as anti-arrhythmic agents. Second, selective inhibition of certain DR K channels in the hippocampus might be useful in enhancing memory in Alzheimer's patients (Lavretsky et al., 1992).

Until recently, K channel investigations were hampered by a paucity of selective neurotoxin probes, which have been so important for investigating sodium and calcium channels. But this has dramatically changed in the past few years. The sea anemone K channel toxins are the most recent addition to the K channel armamentarium. The dendrotoxins are relatively large peptides, and this has limited their utility in determining where they bind to the DR K channels, because of difficulties in preparing analogs or mutants of this toxin, of which the solid-phase synthesis has been recently accomplished. By exchanging functional domains of two DR channels, only one of which is sensitive to dendrotoxin, Stocker et al. (1991) showed that the external loop between S5 and S6 contains at least part of the dendrotoxin receptor. Using K channel mutants, Hurst et al. (1991) reached a similar conclusion. This region contains over 40 residues of sequence, and about half of these contribute towards pore formation. Besides the dendrotoxins, other known K channel toxins include the mast cell degranulating peptide (MCDP), various homologous scorpion peptides (Garcia et al., 1991), two sea anemone toxins (ShK and BgK toxins, Castaneda et al., 1995), and several as yet unpurified molluscan peptides.

Chandy et al. (1995) have shown that the scorpion K channel toxins (charybdotoxin as prototype) are potent blockers of Kv1.1, Kv1.2, and 1.3 Shaker type DR channels. While charybdotoxin (ChTx) also blocks maxi-type K(Ca) channels, some newer ChTx homologs including margatoxin lack K(Ca) channel blocking activity. The scorpion K channel toxins are valuable tools for investigating these ER channels as well as the maxi-K(Ca) channels. Since they are also rather rigid molecules, they are also proving useful as "molecular calipers" for measuring distances between K channel amino acid residues in the outer vestibule of these channels (Stocker and Miller, 1994; Chandy, 1995). A functional map of the interactive surface of the scorpion K channel blocker charybdotoxin has been derived by cloning, expressing, and testing numerous monosubstituted ChTx analogs (Park and Miller, 1992; Stampe et al., 1994). Eight residues (Ser10, Trp14, Arg25, Lys27, Met29, Asn30 and Tyr36) were identified as crucial for ChTx's channel-blocking function. Replacement of any of these residues increased the dissociation rate constant at least 8-fold. Thus, ChTx utilizes a combination of hydrophobic, H-bonding and ionic interactions in its interactions with the Shaker DR (Goldstein et al., 1994) and skeletal muscle maxi-K(Ca) channels (Siampe et al., 1994). The K-channel receptor site may be thought of as reciprocally endowed with the appropriate chemical features to accommodate these interactions.

Both of the two antiparallel B-sheets in the scorpion DR blocking toxins are within the C-terminal region. By preparing and testing various chimeric toxins of the homologous pharmacologically different scorpion toxins ChTx and iberiotoxin, it was shown that the C-terminal third of ChTx confers DR blocking activity, which suggests that residues in the C-terminal β-sheet are interacting with the K channel (Giangiacomo et al., 1993). ShK toxin is structurally quite different from the scorpion toxins and our initial pharmacological data (next section) indicate that it also uses its helical portion to interact with the Shaker-type K channels.

Voltage-gated potassium ($K^+$) channels regulate diverse biological processes (Chandy and Gutman, 1995). A short stretch of amino acids, the P-region, located Between the fifth and sixth transmembrane segments, contributes to the formation of the channel pore. Delineation of the spatial organization of the residues in the P-region would help define the structure of the ion conduction pathway and be valuable for understanding the mechanisms of ion permeation. Scorpion (ChTx, KTx) and sea anemone toxins (ShK) apparently interact strongly with residues in the P-region. It should be possible to deduce the spatial arrangement of the residues in the P-region by using these toxins as structural templates, provided the three-dimensional structures of the toxins is known. In preliminary studies using NMR and molecular modeling, The inventors have shown that four scorpion toxin-blockers of $K^+$ channels, kaliotoxin (KTX), margatoxin (MgTX), noxiustoxin (NTX) and charybdotoxin (ChTX) have a similar tertiary fold.

Many times different molecules utilize the same functional groups to bind with their receptors. In the case of the Na-channel, the toxins tetrodotoxin and saxitoxin are heterocyclic organic compounds which utilize essential guanidinium functionalities to block Na channel function by binding to the Site I receptor (Catterall, 1980). Mu-conotoxins, short peptide toxins isolated from Conus venoms, also competitively bind to the same site I receptor. Interestingly, these toxins are able to discriminate between the tetrodotoxin/saxitoxin receptor on muscle and nerve sodium channels (Ohizumi et al., 1986). Structurally, these peptide toxins are highly constrained by three disulfide bonds which are utilized to correctly position a guanidinium functionality present on an invariant Arg residue (Arg13 in μ-CgTX GIIIA) for channel-blocking activity (Sato et al., 1991). Thus, in tetrodotoxin and saxitoxin, the essential binding features of μ-conotoxin have been naturally incorporated into a small organic type of scaffold. Design of similarly peptidomimetic compounds (but inhibiting Kv1.3 channels) is one major goal of the inventors' project.

Peptides are characteristically highly flexible molecules whose structure is strongly influenced by their environment (Marshall et al., 1978). Nature introduces conformational constraints such as disulfide bonds to help lock a molecule into the biologically active structure. These types of constraints and other structures such as α-helix, β-sheet and reverse turns combine to form the architecture for a peptide/protein's three dimensional structure. The surface localization of turns in proteins, and the predominance of residues containing potentially pharmacophoric information has lead to the hypothesis that turns play a critical role in recognition events (Rose et al., 1985). The stability of α-helical conformations in peptides has also been found to be essential for biological activity in many different systems (Kaiser and Kezdy, 1983).

While the receptor binding domain of an antigenic site, toxin, or hormone may be relatively large, only a relatively small subpopulation of contact residues contribute most of the free energy decrease upon binding. For instance, co-crystallization of human growth hormone with the extracellular domain of its receptor using an Ala scan type of substitution approach has been utilized to identify critical residues providing large contributions to the binding energy of this interaction (Clackson and Wells, 1995). The receptor surface and protein ligand surface each contributed approximately 30 amino acid sidechain contact points. Using Ala-based substitutions at each of these contact points on the receptor, these researchers were able to determine that over 75% of the binding free energy was accounted for by two tryptophan residues. These functionally important residues on human growth hormone receptor make direct contact with those on human growth hormone.

This and other studies provide considerable optimism that it is possible to design small molecules incorporating at least some of the critical chemical groups crucial for interaction with a target receptor. These peptidomimetic compounds should have better use as drugs than the peptides or proteins which they resemble, because they will be more readily absorbed when administered orally, display little or no antigenicity, and be less susceptible to proteolytic attack.

SUMMARY OF THE INVENTION

ShK Toxin-Encoding DNA Segments

The present invention also concerns DNA segments, that can be isolated from virtually any source, that are free from total genomic DNA and that encode the novel peptides disclosed herein. DNA segments encoding these peptide species may prove to encode proteins, polypeptides, subunits, functional domains, and the like of ShK toxin-related or other non-related gene products. In addition these DNA segments may be synthesized entirely in vitro using methods that are well-known to those of skill in the art.

As used herein, the term "DNA segment" refers to a DNA molecule that has been isolated free of total genomic DNA of a particular species. Therefore, a DNA segment encoding a ShK toxin or peptide refers to a DNA segment that contains ShK toxin coding sequences yet is isolated away from, or purified free from, total genomic DNA of the species from which the DNA segment is obtained, which in the instant case is the genome of sea anemones of the genus Stichodactyla, and in particular, the species of Stichodactyla known as *S. helianthus*. Included within the term "DNA segment", are DNA segments and smaller fragments of such segments, and also recombinant vectors, including, for example, plasmids, cosmids, phagemids, phage, viruses, and the like.

Similarly, a DNA segment comprising an isolated or purified ShK toxin-encoding gene refers to a DNA segment which may include in addition to peptide encoding sequences, certain other elements such as, regulatory sequences, isolated substantially away from other naturally occurring genes or protein-encoding sequences. In this respect, the term "gene" is used for simplicity to refer to a functional protein-, polypeptide- or peptide-encoding unit. As will be understood by those skilled in the art, this functional term includes both genomic sequences, operon sequences and smaller engineered gene segments that express, or may be adapted to express, proteins, polypeptides or peptides.

"Isolated substantially away from other coding sequences" means that the gene of interest, in this case, a gene encoding a ShK toxin, forms the significant part of the coding region of the DNA segment, and that the DNA segment does not contain large portions of naturally-occurring coding DNA, such as large chromosomal fragments or other functional genes or operon coding regions. Of course, this refers to the DNA segment as originally isolated, and does not exclude genes, recombinant genes, synthetic linkers, or coding regions later added to the segment by the hand of man.

In particular embodiments, the invention concerns isolated DNA segments and recombinant vectors incorporating DNA sequences that encode a ShK toxin peptide species that includes within its amino acid sequence an amino acid sequence essentially as set forth in SEQ ID NO:1.

The term "a sequence essentially as set forth in SEQ ID NO:1," means that the sequence substantially corresponds to a portion of the sequence of SEQ ID NO:1 and has relatively few amino acids that are not identical to, or a biologically functional equivalent of, the amino acids of any of these sequences. The term "biologically functional equivalent" is well understood in the art and is further defined in detail herein (e.g., see Illustrative Embodiments). Accordingly, sequences that have between about 70% and about 80%, or more preferably between about 81% and about 90%, or even more preferably between about 91% and about 99% amino acid sequence identity or functional equivalence to the amino acids of SEQ ID NO:1 will be sequences that are "essentially as set forth in SEQ ID NO:1."

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared that include a short contiguous stretch encoding either of the peptide sequence disclosed in SEQ ID NO:1, or that are identical to or complementary to DNA sequences which encode any of the peptides disclosed in SEQ ID NO:1. For example, DNA sequences such as about 18 nucleotides, and that are up to about 10,000, about 5,000, about 3,000, about 2,000, about 1,000, about 500, about 200, about 100, about 50, and about 14 base pairs in length (including all intermediate lengths) are also contemplated to be useful.

It will be readily understood that "intermediate lengths", in these contexts, means any length between the quoted ranges, such as 18, 19, 20, 21, 22, 23, etc.; 30, 31, 32, etc.; 50, 51, 52, 53, etc.; 100, 101, 102, 103, etc.; 150, 151, 152, 153, etc.; including all integers through the 200–500; 500–1,000; 1,000–2,000; 2,000–3,000; 3,000–5,000; and up to and including sequences of about 5200 nucleotides and the like.

It will also be understood that this invention is not limited to the particular nucleic acid sequences which encode peptides of the present invention, or which encode the amino acid sequence of SEQ ID NO:1. Recombinant vectors and isolated DNA segments may therefore variously include the peptide-coding regions themselves, coding regions bearing selected alterations or modifications in the basic coding region, or they may encode larger polypeptides that nevertheless include these peptide-coding regions or may encode biologically functional equivalent proteins or peptides that have variant amino acids sequences.

The DNA segments of the present invention encompass biologically-functional, equivalent peptides. Such sequences may arise as a consequence of codon degeneracy and functional equivalency that are known to occur naturally within nucleic acid sequences and the proteins thus encoded. Alternatively, functionally-equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test mutants in order to examine activity at the molecular level.

If desired, one may also prepare fusion proteins and peptides, e.g., where the peptide-coding regions are aligned within the same expression unit with other proteins or peptides having desired functions, such as for purification or immunodetection purposes (e.g., proteins that may be purified by affinity chromatography and enzyme label coding regions, respectively).

Recombinant vectors form further aspects of the present invention. Particularly useful vectors are contemplated to be those vectors in which the coding portion of the DNA segment, whether encoding a full length protein or smaller peptide, is positioned under the control of a promoter. The promoter may be in the form of the promoter that is naturally associated with a gene encoding peptides of the present invention, as may be obtained by isolating the 5' non-coding sequences located upstream of the coding segment or exon, for example, using recombinant cloning and/or PCR™ technology, in connection with the compositions disclosed herein.

DNA Segments as Hybridization Probes and Primers

In addition to their use in directing the expression of ShK toxins or peptides of the present invention, the nucleic acid sequences contemplated herein also have a variety of other uses. For example, they also have utility as probes or primers in nucleic acid hybridization embodiments. As such, it is contemplated that nucleic acid segments encoding ShK or ShK analogs that comprise a sequence region that consists of at least a 14 nucleotide long contiguous sequence will find particular utility. Longer contiguous identical or complementary sequences, e.g., those of about 20, 30, 40, 50, 100, 200, 500, 1000, 2000, 5000 bp, etc. (including all intermediate lengths and up to and including the full-length sequence of 5200 basepairs will also be of use in certain embodiments.

The ability of such nucleic acid probes to specifically hybridize to ShK toxin-encoding sequences will enable them to be of use in detecting the presence of complementary sequences in a given sample. However, other uses are envisioned, including the use of the sequence information for the preparation of mutant species primers, or primers for use in preparing other genetic constructions.

Nucleic acid molecules having sequence regions consisting of contiguous nucleotide stretches of about 10 to about 14, or from about 15 to about 20, or about 30, or about 40, or about 50, or even of from about 100 to about 200 nucleotides or so, identical or complementary to a DNA sequence encoding ShK or ShK analogs, are particularly contemplated as hybridization probes for use in, e.g., Southern and Northern blotting. Smaller fragments will generally find use in hybridization embodiments, wherein the length of the contiguous complementary region may be varied, such as between about 10 and 14 up to about 100 or about 200 nucleotides, but larger contiguous complementary stretches may be used, according to the length complementary sequences one wishes to detect.

Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCRTM technology of U.S. Pat. Nos. 4,683,195 and 4,683,202 (each incorporated herein by reference), by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of DNA fragments. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by about 0.02 M to about 0.15 M NaCl at temperatures of about 50° C. to about 70° C. Such selective conditions tolerate little, if any, mismatch between the probe and the template or target strand, and would be particularly suitable for isolating ShK toxin-encoding DNA segments. Detection of DNA segments via hybridization is well-known to those of skill in the art, and the teachings of U.S. Pat. Nos. 4,965,188 and 5,176,995 (each incorporated herein by reference) are exemplary of the methods of hybridization analyses. Teachings such as those found in the texts of Maloy et al., 1990, 1994; Segal 1976; Prokop, 1991; and Kuby, 1994, are particularly relevant.

Of course, for some applications, for example, where one desires to prepare mutants employing a mutant primer strand hybridized to an underlying template or where one seeks to isolate ShK toxin-encoding sequences from related species, functional equivalents, or the like, less stringent hybridization conditions will typically be needed in order to allow formation of the heteroduplex. In these circumstances, one may desire to employ conditions such as about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmentally undesirable reagents. In the case of enzyme tags, calorimetric indicator substrates are known that can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface so as to remove nonspecific ally bound probe molecules, specific hybridization is detected, or even quantitated, by means of the label.

Recombinant Vectors and ShK Toxin Expression

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a DNA segment encoding a ShK toxin or peptide in its natural environment. Such promoters may include promoters normally associated with other genes, and/or promoters isolated from any animal, bacterial, viral, eukaryotic, or plant cell. Naturally, it will be important to employ a promoter that effectively directs the expression of the DNA segment in the cell type, organism, or animal, chosen for expression. The use of promoter and cell type combinations for protein expression is generally known to those of skill in the art of molecular biology, for example, see Sambrook et al., 1989. The promoters employed may be constitutive, or inducible, and can be used under the appropriate conditions to direct high level expression of the introduced DNA segment, such as is advantageous in the large-scale production of recombinant proteins or peptides. Appropriate promoter systems contemplated for use in high-level expression include, but are not limited to, the Pichia expression vector system (Pharmacia LKB Biotechnology).

In connection with expression embodiments to prepare recombinant proteins and peptides, it is contemplated that longer DNA segments will most often be used, with DNA segments encoding the entire peptide sequence being most preferred. However, it will be appreciated that the use of shorter DNA segments to direct the expression of ShK peptides or epitopic core regions, such as may be used to generate anti-ShK toxin antibodies, also falls within the scope of the invention. DNA segments that encode peptide antigens from about 8 to about 50 amino acids in length, or more preferably, from about 8 to about 30 amino acids in length, or even more preferably, from about 8 to about 20 amino acids in length are contemplated to be particularly useful. Such peptide epitopes may be amino acid sequences which comprise contiguous amino acid sequence from SEQ ID NO:1.

ShK Toxin Transgenes and Transgenic Cells

In yet another aspect, the present invention provides methods for producing a transgenic cell which expresses a nucleic acid segment encoding the novel ShK toxin and toxin analogs of the present invention. The process of producing transgenic cells is well-known in the art. In general, the method comprises transforming a suitable host cell with a DNA segment which contains a promoter operatively linked to a coding region that encodes a S. helianthus ShK toxin or a ShK toxin analog, or synthetically-modified ShK toxin. Such a coding region is generally operatively linked to a transcription-terminating region, whereby the promoter is capable of driving the transcription of the coding region in the cell, and hence providing the cell the ability to produce the recombinant protein in vivo. Alternatively, in instances where it is desirable to control, regulate, or decrease the amount of a particular recombinant ShK toxin expressed in a particular transgenic cell, the invention also provides for the expression of ShK toxin antisense mRNA. The use of antisense mRNA as a means of controlling or decreasing the amount of a given protein of interest in a cell is well-known in the art.

Another aspect of the invention comprises transgenic cells which express a gene or gene segment encoding one or more of the novel polypeptide compositions disclosed herein. As used herein, the term "transgenic cell" is intended to refer to a cell that has incorporated DNA sequences, including but not limited to genes which are perhaps not normally present, DNA sequences not normally transcribed into RNA or translated into a protein ("expressed"), or any other genes or DNA sequences which one desires to introduce into the non-transformed cell, such as genes which may normally be present in the non-transformed cell but which one desires to either genetically engineer or to have altered expression.

It is contemplated that in some instances the genome of a transgenic cell of the present invention will have been augmented through the stable introduction of one or more ShK transgenes, either native, synthetically modified, or mutated. In some instances, more than one transgene will be incorporated into the genome of the transformed host cell. Such is the case when more than one ShK toxin-encoding DNA segment is incorporated into the genome of such a cell. In certain situations, it may be desirable to have one, two, three, four, or even more S. helianthus ShK toxins (either native or recombinantly-engineered) incorporated and stably expressed in the transformed transgenic cell.

A preferred gene which may be introduced includes, for example, a ShK toxin-encoding DNA sequence from sea anemone origin, and particularly one or more of those described herein which are obtained from Stichodactyla spp. Highly preferred nucleic acid sequences are those obtained from S. helianthus, or any of those sequences which have been genetically engineered to decrease or increase the activity of the ShK toxin in such a transformed host cell.

Means for transforming a host cell and the preparation of a transgenic cell line are well-known in the art, and are discussed herein. Vectors, plasmids, cosmids, YACs (yeast artificial chromosomes) and DNA segments for use in transforming such cells will, of course, generally comprise either the operons, genes, or gene-derived sequences of the present invention, either native, or synthetically-derived, and particularly those encoding the disclosed ShK toxins and toxin analogs. These DNA constructs can further include structures such as promoters, enhancers, polylinkers, or even gene sequences which have positively- or negatively-regulating activity upon the particular genes of interest as desired. The DNA segment or gene may encode either a native or modified ShK toxin, which will be expressed in the resultant recombinant cells, and/or which will impart an improved phenotype to the transformed cell.

Site-Specific Mutagenesis

Site-specific mutagenesis is a technique useful in the preparation of individual peptides, or biologically functional equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart of two strands of a double stranded vector which includes within its sequence a DNA sequence which encodes the desired peptide. An oligonucleotide primer bearing the desired mutated sequence is prepared, generally synthetically. This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected which include recombinant vectors bearing the mutated sequence arrangement.

The preparation of sequence variants of the selected peptide-encoding DNA segments using site-directed mutagenesis is provided as a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants.

Antibody Compositions and Methods of Making

In particular embodiments, the inventors contemplate the use of antibodies, either monoclonal or polyclonal which bind to the ShK toxins and toxin analogs disclosed herein. Means for preparing and characterizing antibodies are well known in the art (See, e.g., Antibodies: A Laboratory Manual, Cold Spring Harbor Laboratory, 1988; incorporated herein by reference). The methods for generating monoclonal antibodies (mAbs) generally begin along the same lines as those for preparing polyclonal antibodies. Briefly, a polyclonal antibody is prepared by immunizing an animal with an immunogenic composition in accordance with the present invention and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bis-biazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicily is obtained, the immunized animal can be bled and the serum isolated and stored, and/or the animal can be used to generate mAbs.

mAbs may be readily prepared through use of well-known Techniques, such as those exemplified in U.S. Pat. No. 4,196,265, incorporated herein by reference. Typically, this technique involves immunizing a suitable animal with a selected immunogen composition, e.g., a purified or partially purified ShK toxin, polypeptide or peptide. The immunizing composition is administered in a manner effective to stimulate antibody producing cells. Rodents such as mice and rats are preferred animals, however, the use of rabbit, sheep, or frog cells is also possible. The use of rats may provide certain advantages (Goding, 1986, pp. 60–61), but mice are preferred, with the BALB/c mouse being most preferred as this is most routinely used and generally gives a higher percentage of stable fusions.

Following immunization, somatic cells with the potential for producing antibodies, specifically B lymphocytes (B cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render them incapable of growing in certain selective media which support the growth of only the desired fused cells (hybridomas).

Any one of a number of myeloma cells may be used, as are known to those of skill in the art (Goding, pp. 65–66, 1986; Campbell, pp. 75–83, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XXO Bul; for rats, one may use R210.RCY3, Y3-Ag 1.2.3, IR983F and 4B210; and U-266, GM1500-GRG2, LICR—LON—HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, 1975; 1976), and those using polyethylene glycol (PEG), such as 37% (vol./vol.) PEG, (Gefter et al., 1977). The use of electrically induced fusion methods is also appropriate (Goding, 1986, pp. 71–74).

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

ELISAs and Immunoprecipitation

ELISAs may be used in conjunction with the invention. In an ELISA assay, proteins or peptides incorporating ShK toxin antigen sequences are immobilized onto a selected surface, preferably a surface exhibiting a protein affinity such as the wells of a polystyrene microtiter plate. After washing to remove incompletely adsorbed material, it is desirable to bind or coat the assay plate wells with a nonspecific protein that is known to be antigenically neutral with regard to the test antisera such as bovine serum albumin (BSA), casein or solutions of milk powder. This allows for blocking of nonspecific adsorption sites on the immobilizing surface and thus reduces the background caused by nonspecific binding of antisera onto the surface.

After binding of antigenic material to the well, coating with a non-reactive material to reduce background, and washing to remove unbound material, the immobilizing surface is contacted with the antisera or clinical or biological extract to be tested in a manner conducive to immune complex (antigen/antibody) formation. Such conditions preferably include diluting the antisera with diluents such as BSA, bovine gamma globulin (BGG) and phosphate buffered saline (PBS)/Tween®. These added agents also tend to assist in the reduction of nonspecific background. The layered antisera is then allowed to incubate for from about 2 to about 4 hours, at temperatures preferably on the order of about 25° to about 27° C. Following incubation, the antisera-contacted surface is washed so as to remove non-immunocomplexed material. A preferred washing procedure includes washing with a solution such as PBS/Tween®, or borate buffer.

Following formation of specific immunocomplexes between the test sample and the bound antigen, and subsequent washing, the occurrence and even amount of immunocomplex formation may be determined by subjecting same to a second antibody having specificity for the first. To provide a detecting means, the second antibody will preferably have an associated enzyme that will generate a color development upon incubating with an appropriate chromogenic substrate. Thus, for example, one will desire to contact and incubate the antisera-bound surface with a urease or peroxidase-conjugated anti-human IgG for a period of time and under conditions which favor the development of immunocomplex formation (e.g., incubation for 2 hours at room temperature in a PBS-containing solution such as PBS Tween®).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generation, e.g., using a visible spectra spectrophotometer.

The anti-ShK toxin antibodies of the present invention are particularly useful for the isolation of other ShK toxin antigens by immunoprecipitation. Irimunoprecipitation involves the separation of the target antigen component from a complex mixture, and is used to discriminate or isolate minute amounts of protein. For the isolation of membrane proteins cells must be solubilized into detergent micelles. Nonionic salts are preferred, since other agents such as bile salts, precipitate at acid pH or in the presence of bivalent cations.

In an alternative embodiment the antibodies of the present invention are useful for the close juxtaposition of two antigens. This is particularly useful for increasing the localized concentration of antigens, e.g. enzyme-substrate pairs.

Western Blots

The compositions of the present invention will find great use in immunoblot or western blot analysis. The anti-peptide antibodies may be used as high-affinity primary reagents for the identification of proteins immobilized onto a solid support matrix, such as nitrocellulose, nylon or combinations thereof. In conjunction with immuno-precipitation, followed by gel electrophoresis, these may be used as a single step reagent for use in detecting antigens against which secondary reagents used in the detection of the antigen cause an adverse background. This is especially useful when the antigens studied are immunoglobulins (precluding the use of immunoglobulins binding bacterial cell wall components), the antigens studied cross-react with the detecting agent, or they migrate at the same relative molecular weight as a cross-reacting signal.

Immunologically-based detection methods for use in conjunction with Western blotting include enzymatically-, radiolabel-, or fluorescently-tagged secondary antibodies against the toxin moiety are considered to be of particular use in this regard.

ShK Toxin Screening and Detection Kits

The present invention contemplates methods and kits for screening samples suspected of containing ShK toxin polypeptides or ShK toxin-related polypeptides, or cells producing such polypeptides. A kit may contain one or more antibodies of the present invention, and may also contain reagent(s) for detecting an interaction between a sample and an antibody of the present invention. The provided reagent (s) can be radio-, fluorescently- or enzymatically-labeled. The kit can contain a known radiolabeled agent capable of binding or interacting with a nucleic acid or antibody of the present invention.

The reagent(s) of the kit can be provided as a liquid solution, attached to a solid support or as a dried powder. Preferably, when the reagent(s) are provided in a liquid solution, the liquid solution is an aqueous solution. Preferably, when the reagent(s) provided are attached to a solid support, the solid support can be chroinatograph media, a test plate having a plurality of wells, or a microscope slide. When the reagent(s) provided are a dry powder, the powder can be reconstituted by the addition of a suitable solvent, that may be provided.

In still further embodiments, the present invention concerns immunodetection methods and associated kits. It is proposed that the ShK toxins or peptides of the present invention may be employed to detect antibodies having reactivity therewith, or, alternatively, antibodies prepared in accordance with the present invention, may be employed to detect ShK toxins or ShK toxin-related epitope-containing peptides. In general, these methods will include first obtaining a sample suspected of containing such a protein, peptide or antibody, contacting the sample with an antibody or peptide in accordance with the present invention, as the case may be, under conditions effective to allow the formation of an immunocomplex, and then detecting the presence of the immunocomplex.

In general, the detection of immunocomplex formation is quite well known in the art and may be achieved through the application of numerous approaches. For example, the present invention contemplates the application of ELISA, RIA, immunoblot (e.g., dot blot), indirect immunofluorescence techniques and the like. Generally, immunocomplex formation will be detected through the use of a label, such as a radiclabel or an enzyme tag (such as alkaline phosphatase, horseradish peroxidase, or the like). Of course, one may find additional advantages through the use of a secondary binding ligand such as a second antibody or a biotin/avidin ligand binding arrangement, as is known in the art.

For assaying purposes, it is proposed that virtually any sample suspected of comprising either a ShK toxin or peptide or a ShK toxin-related peptide or antibody sought to be detected, as the case may be, may be employed. It is contemplated that such embodiments may have application in the titering of antigen or antibody samples, in the selection of hybridomas, and the like. In related embodiments, the present invention contemplates the preparation of kits that may be employed to detect the presence of ShK toxins or related peptides and/or antibodies in a sample. Samples may include cells, cell supernatants, cell suspensions, cell extracts, enzyme fractions, protein extracts, or other cell-free compositions suspected of containing ShK toxins or peptides. Generally speaking, kits in accordance with the present invention will include a suitable ShK toxin, peptide or an antibody directed against such a protein or peptide, together with an immunodetection reagent and a means for containing the antibody or antigen and reagent. The immunodetection reagent will typically comprise a label associated with the antibody or antigen, or associated with a secondary binding ligand. Exemplary ligands might include a secondary antibody directed against the first antibody or antigen or a biotin or avidin (or streptavidin) ligand having an associated label. Of course, as noted above, a number of exemplary labels are known in the art and all such labels may be employed in connection with the present invention.

The container will generally include a vial into which the antibody, antigen or detection reagent may be placed, and preferably suitably aliquotted. The kits of the present invention will also typically include a means for containing the antibody, antigen, and reagent containers in close confinement for commercial sale. Such containers may include injection or blow-molded plastic containers into which the desired vials are retained.

Epitopic Core Sequences

The present invention is also directed to protein or peptide compositions, free from total cells and other peptides, which comprise a purified protein or peptide which incorporates an epitope that is immunologically cross-reactive with one or more anti-ShK toxin antibodies. In particular, the invention concerns epitopic core sequences derived from ShK proteins or peptides.

As used herein, the term "incorporating an epitope(s) that is immunologically cross-reactive with one or more anti-ShK toxin antibodies" is intended to refer to a peptide or protein antigen which includes a primary, secondary or tertiary structure similar to an epitope located within a ShK toxin or polypeptide. The level of similarity will generally be to such a degree that monoclonal or polyclonal antibodies directed against the ShK toxin or polypeptide will also bind to, react with, or otherwise recognize, the cross-reactive peptide or protein antigen. Various immunoassay methods may be employed in conjunction with such antibodies, such as, for example, Western blotting, ELISA, RIA, and the like, all of which are known to those of skill in the art.

The identification of immunodominant epitopes, and/or their functional equivalents, suitable for use in vaccines is a relatively straightforward matter. For example, one may employ the methods of Hopp, as taught in U.S. Pat. No. 4,554,101, incorporated herein by reference, which teaches the identification and preparation of epitopes from amino acid sequences on the basis of hydrophilicity. The methods described in several other papers, and software programs based thereon, can also be used to identify epitopic core sequences (see, for example, Jameson and Wolf, 1988; Wolf et al., 1988; U.S. Pat. No. 4,554,101). The amino acid sequence of these "epitopic core sequences" may then be readily incorporated into peptides, either through the application of either peptide synthesis or recombinant technology.

Preferred peptides for use in accordance with the present invention will generally be on the order of about 8 to about 20 amino acids in length, and more preferably about 8 to about 15 amino acids in length. It is proposed that shorter antigenic ShK toxin-derived peptides will provide advantages in certain circumstances, for example, in the preparation of immunologic detection assays. Exemplary advantages include the ease of preparation and purification, the relatively low cost and improved reproducibility of production, and advantageous biodistribution.

It is proposed that particular advantages of the present invention may be realized through the preparation of synthetic peptides which include modified and/or extended epitopic/immunogenic core sequences which result in a "universal" epitopic peptide directed to ShK toxins. These epitopic core sequences are identified herein in particular aspects as hydrophilic regions of the particular polypeptide antigen. It is proposed that these regions represent those which are most likely to promote T-cell or B-cell stimulation, and, hence, elicit specific antibody production.

An epitopic core sequence, as used herein, is a relatively short stretch of amino acids that is "complementary" to, and therefore will bind, antigen binding sites on the ShK toxin-directed antibodies disclosed herein. Additionally or alternatively, an epitopic core sequence is one that will elicit antibodies that are cross-reactive with antibodies directed against the peptide compositions of the present invention. It will be understood that in the context of the present disclosure, the term "complementary" refers to amino acids or peptides that exhibit an attractive force towards each other. Thus, certain epitope core sequences of the present invention may be operationally defined in terms of their ability to compete with or perhaps displace the binding of the desired protein antigen with the corresponding protein-directed antisera.

In general, the size of the polypeptide antigen is not believed to be particularly crucial, so long as it is at least large enough to carry the identified core sequence or sequences. The smallest useful core sequence anticipated by the present disclosure would generally be on the order of about 8 amino acids in length, with sequences on the order of 10 to 20 being more preferred. Thus, this size will generally correspond to the smallest peptide antigens prepared in accordance with the invention. However, the size of the antigen may be larger where desired, so long as it contains a basic epitopic core sequence.

The identification of epitopic core sequences is known to those of skill in the art, for example, as described in U.S. Pat. No. 4,554,101, incorporated herein by reference, which teaches the identification and preparation of epitopes from amino acid sequences on the basis of hydrophilicity. Moreover, numerous computer programs are available for use in predicting antigenic portions of proteins (see e.g., Jameson and Wolf, 1988; Wolf et al., 1988). Computerized peptide sequence analysis programs (e.g., DNAStar® software, DNAStar, Inc., Madison, Wis.) may also be useful in designing synthetic peptides in accordance with the present disclosure.

Syntheses of epitopic sequences, or peptides which include an antigenic epitope within their sequence, are readily achieved using conventional synthetic techniques such as the solid phase method (e.g., through the use of commercially available peptide synthesizer such as an Applied Biosystems Model 430A Peptide Synthesizer). Peptide antigens synthesized in this manner may then be aliquotted in predetermined amounts and stored in conventional manners, such as in aqueous solutions or, even more preferably, in a powder or lyophilized state pending use.

In general, due to the relative stability of peptides, they may be readily stored in aqueous solutions for fairly long periods of time if desired, e.g., up to six months or more, in virtually any aqueous solution without appreciable degradation or loss of antigenic activity. However, where extended aqueous storage is contemplated it will generally be desirable to include agents including buffers such as Tris or phosphate buffers to maintain a pH of about 7.0 to about 7.5. Moreover, it may be desirable to include agents which will inhibit microbial growth, such as sodium azide or Merthiolate. For extended storage in an aqueous state it will be desirable to store the solutions at about 4° C., or more preferably, frozen. Of course, where the peptides are stored in a lyophilized or powdered state, they may be stored virtually indefinitely, e.g., in metered aliquots that may be rehydrated with a predetermined amount of water (preferably distilled) or buffer prior to use.

Biological Functional Equivalents

Modification and changes may be made in the structure of the peptides of the present invention and DNA segments which encode them and still obtain a functional molecule that encodes a protein or peptide with desirable characteristics. The following is a discussion based upon changing the amino acids of a protein to create an equivalent, or even an improved, second-generation molecule. In particular embodiments of the invention, mutated ShK toxins are contemplated to be useful for increasing the insecticidal activity of the protein, and consequently increasing the activity and/or expression of the recombinant transgene in a cell. The amino acid changes may be achieved by changing the codons of the DNA sequence, according to the codons in Table 1.

TABLE 1

| Amino Acids | | | Codons | | | | |
|---|---|---|---|---|---|---|---|
| Alanine | Ala | A | GCA | GCC | GCG | GCU | |
| Cysteine | Cys | C | UGC | UGU | | | |
| Aspartic acid | Asp | D | GAC | GAU | | | |
| Glutamic acid | Glu | E | GAA | GAG | | | |
| Phenylalanine | Phe | F | UUC | UUU | | | |
| Glycine | Gly | G | GGA | GGC | GGG | GGU | |
| Histidine | His | H | CAC | CAU | | | |
| Isoleucine | Ile | I | AUA | AUC | AUU | | |
| Lysine | Lys | K | AAA | AAG | | | |
| Leucine | Leu | L | UUA | UUG | CUA | CUC | CUG | CUU |
| Methionine | Met | M | AUG | | | | |
| Asparagine | Asn | N | AAC | AAU | | | |
| Proline | Pro | P | CCA | CCC | CCG | CCU | |
| Glutamine | Gln | Q | CAA | CAG | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | |
| Valine | Val | V | GUA | GUC | GUG | GUU | |
| Tryptophan | Trp | W | UGG | | | | |
| Tyrosine | Tyr | Y | UAC | UAU | | | |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8,); tyrosine (−2.3); phenylalanine (−2.5); tryptophan (−3.4).

Figure 9:
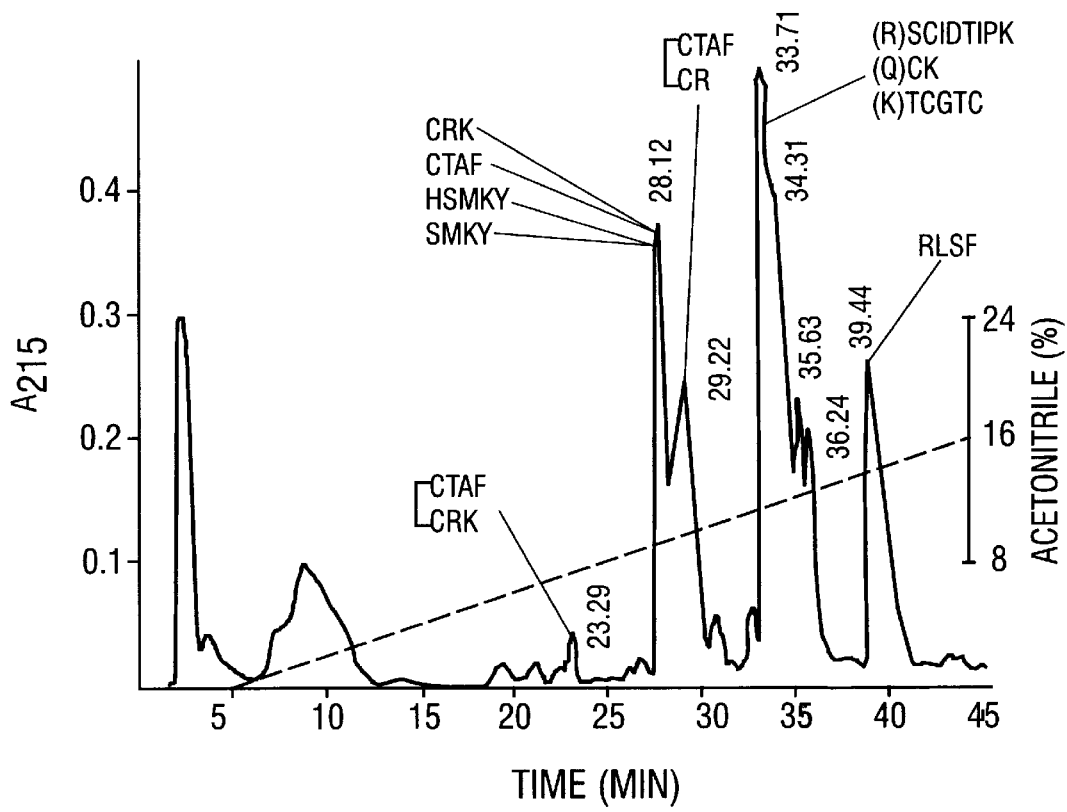

It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A. Structure of ShK toxin. Plots as a function of residue number of the number of NOEs used in the final structure calculation, r.m.s. differences from the average for the backbone heavy atoms N, Cα and C, superimposed over the whole molecule, and ϕ and ψ angular order parameters. NOE categories are shown as follows: long-range, black; medium-range, horizontal lines; sequential, cross-hatching; intraresidue, open.

FIG. 1B. Stereo view of the best 20 structures of ShK toxin, superimposed over the backbone heavy atoms N, Cα and C for residues 3–33. Only the backbone heavy atoms are shown, except for the three disulfide bonds (3–35, 12–28 and 17–32), which are shaded gray.

FIG. 1C. Two views of a ribbon diagram of the structure of ShK toxin which is closest to the average, showing the backbone and disulfide bones. The two short helices are colored magenta and the helical turns are blue. The two views are related by a ~90° rotation about the vertical axis.

FIG. 2A. Comparison of the structures and sequences of ShK toxin and the scorpion-derived toxins charybdotoxin and agitoxin 2. For ShK toxin the structure closest to the average is shown, while for each of the scorpion toxins the first entry from the Brookhaven Protein Data Bank (Bernstein et al., 1977) files 2CRD (charybdotoxin) and 1AGT (agitoxin 2) was used. The structure diagrams were generated using MOLSCRIPT (Kraulis, 1991). Dots in the sequence of agitoxin 2 denote residues identical with charybdotoxin.

FIG. 2B. Ribbon diagram of the structure of ShK toxin which is closest to the average. The side chains of Lys 9 (blue) and Arg (11 (cyan), which are important in binding to the Kv1.3 channel (see text) and Lys 22, which is important in binding to both the Kv1.3 and Kv1.2 channels, are shown. Also highlighted are Lys 30 and Asp 5 (red), which may form a salt bridge important in folding.

FIG. 2C. CPK surface of the same view as in (b), with the side chains of residues 9, 11 and 22 highlighted.

FIG. 3. Sequence comparison between ShK toxin (Karlsson et al., 1992) BgK toxin (Aneiros et al., 1993). Boxed-in residues are either conservative substitutions or identical.

FIG. 4A. Oxidation profile of the folding of synthetic ShK toxin as determined by RP-HPLC. Time 0, fully reduced peptide. Gradient conditions were 5–55% MeCN into 0.1% TFA in $H_2O$ in 25 min at 1.5 ml/min on a VCydac $C_{18}$ column. Peak identification: 9.14 min scavenger 1,2-ethanedithiol, 10.76 min oxidized ShK toxin panels B and C, and 13.57 min reduced ShK toxin panel A.

FIG. 4B. Oxidation profile of the folding of synthetic ShK toxin as determined by RP-HPLC. After 18 h oxidation. . Gradient conditions were 5–55% MeCN into 0.1% TFA in $H_2O$ in 25 min at 1.5 ml/min on a Vydac $C_{18}$ column. Peak identification: 9.14 min scavenger 1,2ethanedithiol, 10.76 min oxidized ShK toxin panels B and C, and 13.57 min reduced ShK toxin panel A.

FIG. 4C. Oxidation profile of the folding of synthetic ShK toxin as determined by RP-HPLC. After 36 h oxidation. Gradient conditions vere 5–55% MeCN into 0.1% TFA in $H_2O$ in 25 min at 1.5 ml/min on a Vydac $C_{18}$ column. Peak identification: 9.14 min scavenger 1,2ethanedithiol, 10.76 min oxidized ShK toxin panels B and C, and 13.57 min reduced ShK toxin panel A.

FIG. 5A. HPLC comparison of synthetic and natural ShK toxin. Synthetic toxin (5 nmol). The peptides were eluted using a gradient from 5 to 45% of MeCN versus 0.1% TFA in $H_2O$ in 20 min at 1.0 ml/min.

FIG. 5B. HPLC comparison of synthetic and natural ShK toxin. Natural toxin (5 nmol). The peptides were eluted using a gradient from 5 to 45% of MeCN versus 0.1% TFA in $H_2O$ in 20 min at 1.0 ml/min.

FIG. 5C. HPLC comparison of synthetic and natural ShK toxin. Coinjection of a 1:1 mixture of synthetic and natural.. The peptides were eluted using a gradient from 5 to 45% of MeCN versus 0.1% TFA in $H_2O$ in 20 min at 1.0 ml/min.

FIG. 6. Inhibition of specific [$^{125}$I]DTX binding to rat brain membranes by natural 0 and synthetic ♦ ShK toxin. Mean data of two experiments. Each measurement was performed in triplicate.

FIG. 7. Inhibition of [$^{125}$I]-ChTX binding to Kv1.3 channels by ShK toxin. Jurkat T lymphocytes were incubated for 20 min at 22° C. with 25 pM [$^{125}$I]-ChTX in the presence of increasing concentrations of ShK toxin. Specifically bound [$^{125}$I]-ChTX was determined as described, and plotted as percentage inhibition of [$^{125}$I]-ChTX vs. Test concentration of ShK toxin. Data are presented as means±SEM (n=4).

FIG. 8. Functional blockade of potassium currents by ShK toxin. Membrane current was measured in Jurkat T lymphocytes as described in Experimental Procedures and percentage current block plotted versus test concentration of ShK toxin. Data are presented as means±SEM at each concentration and the smooth curve is the best fit to the data of a single binding site isotherm with an $IC_{50}$-value of 133 pM (95% c.i. 105–168 pM) and a Hill coefficient of 1.7 (95% c.i. 1.0–2.5). Each cell was exposed to a single concentration of toxin and the data pooled to construct the concentration response curve (n=23).

FIG. 9. RP-HPLC profile of chymotryptic-tryptic digest of ShK toxin at pH 6.5. Residues in parentheses represent N-terminally truncated species also present.

Figure 1B:
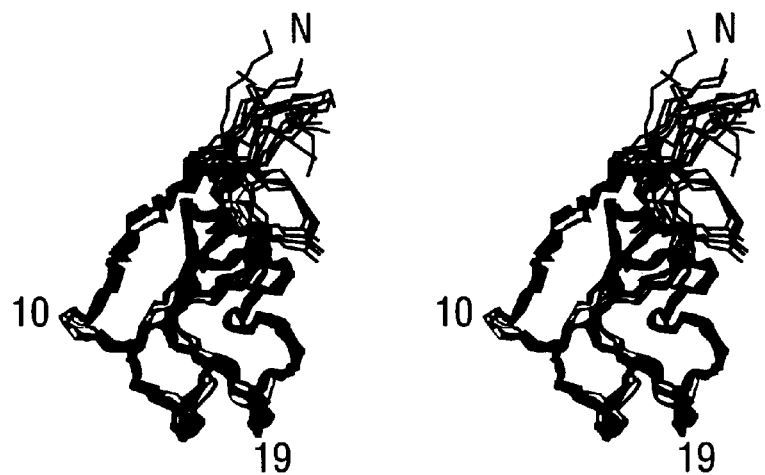
Figure 1C:
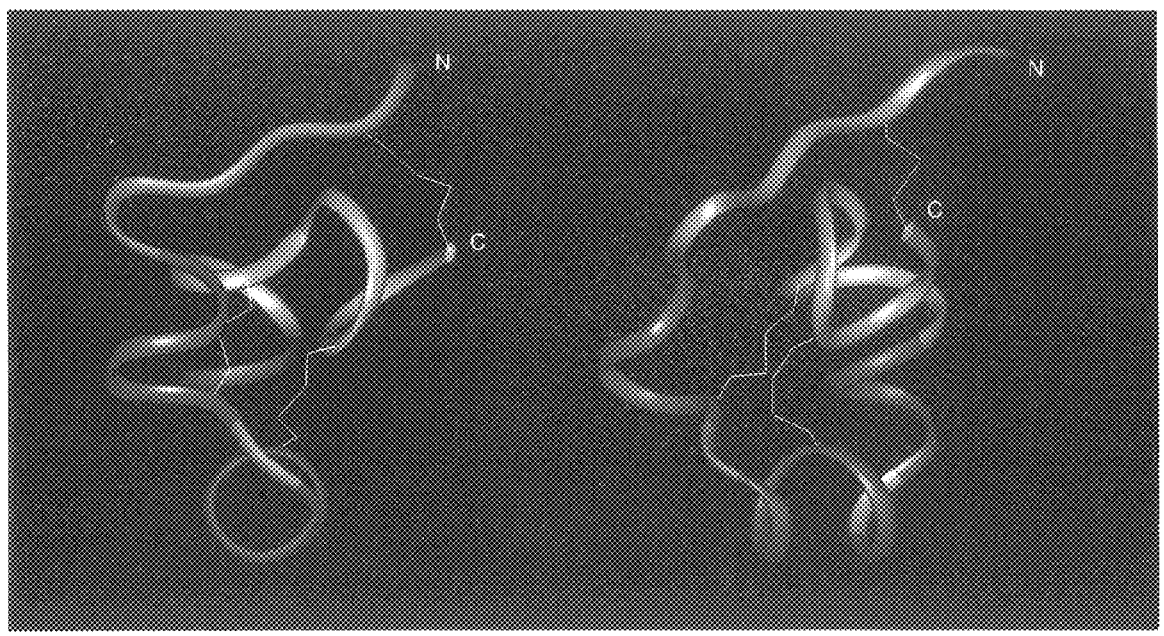
Figure 10:
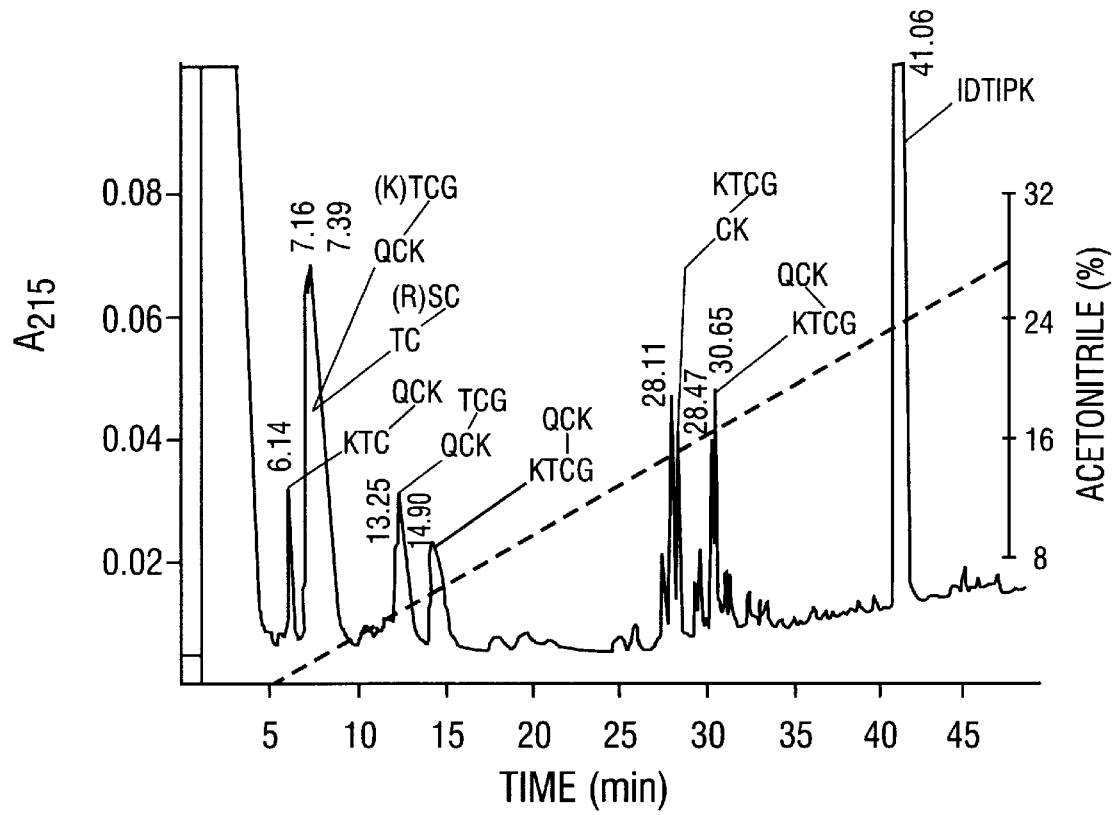

FIG. 10. RP-HPLC profile of thermolysin digest (pH 6.5) of the tryptic-chymotryptic disulfide cluster (33.71 min peak in FIG. 1A, FIG. 1B and FIG. 1C). Residues in parentheses represent N-terminally truncated species also present.

Figure 2A:
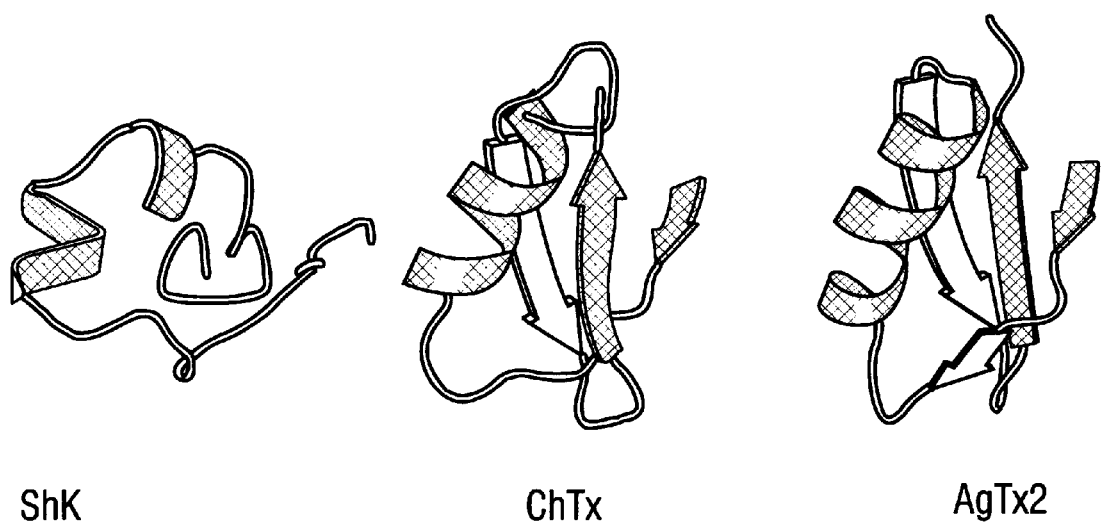
Figure 2B:
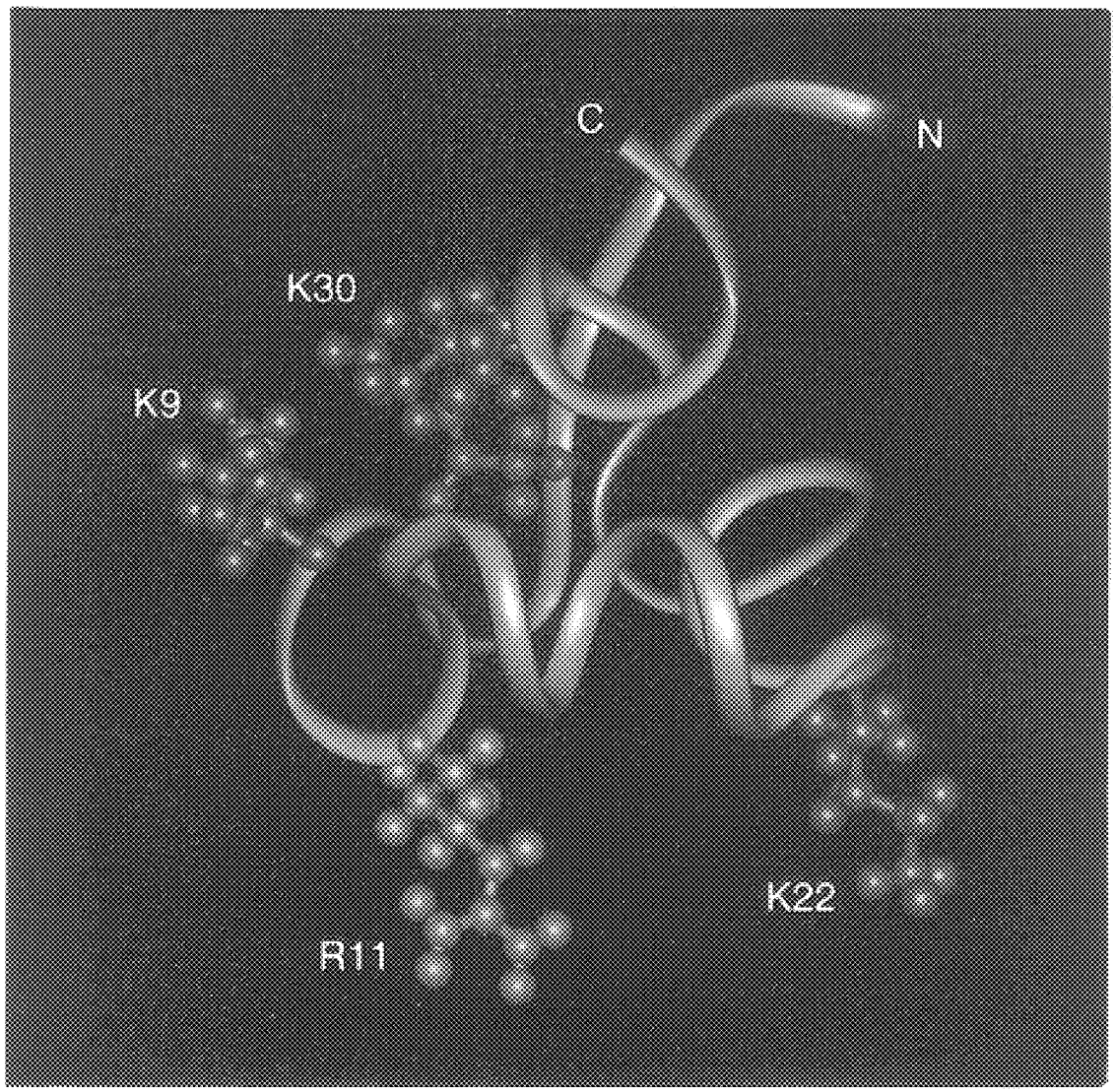
Figure 2C:
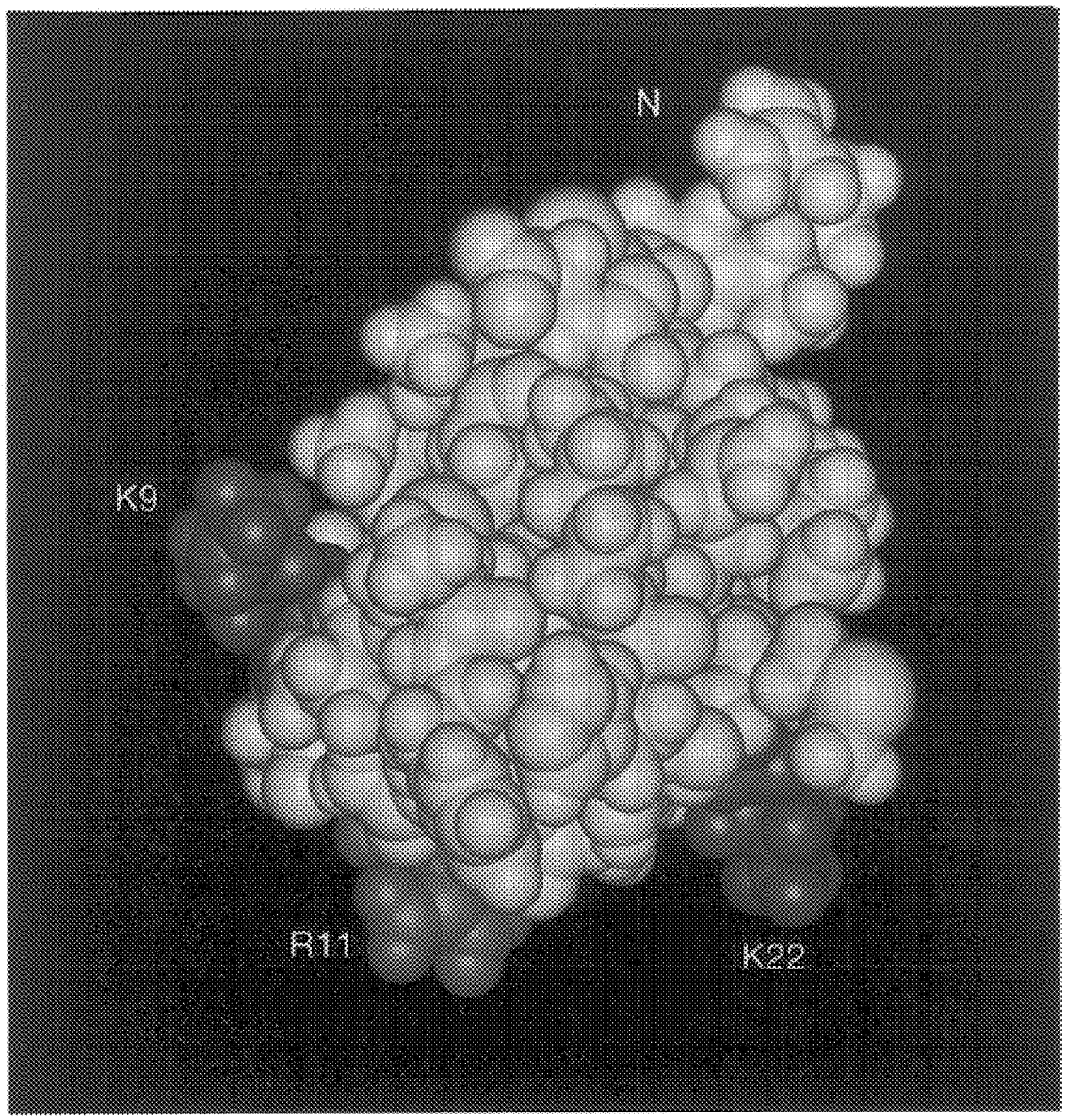
Figure 11:
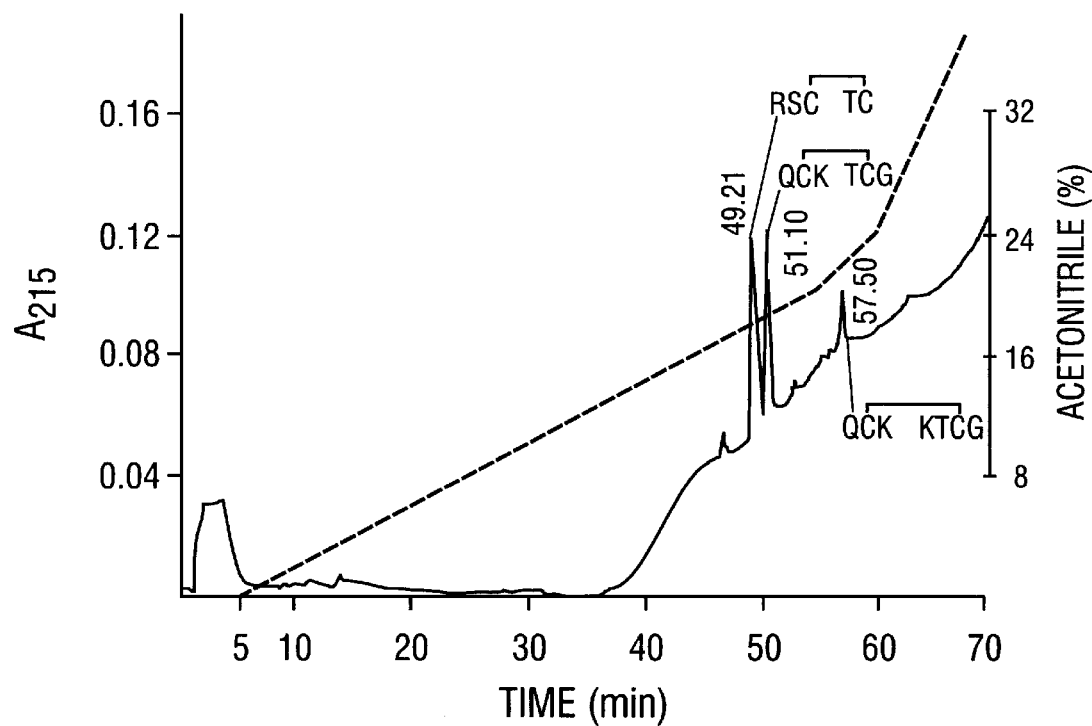

FIG. 11. RP-HPLC purification of the early eluting fragments (7–9 min peak in FIG. 2A, FIG. 2B and FIG. 2C) derived from the thermolytic digest of the disulfide cluster peak at 33.71 min derived from the tryptic-chymotryptic digest. Gradient conditions are as indicated, using HFE as the ion-pairing reagent.

Figure 12:
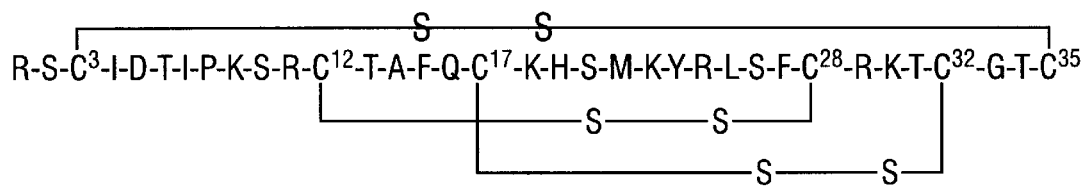

FIG. 12. Schema tic representation of ShK disulfide pairings.

Figure 13:
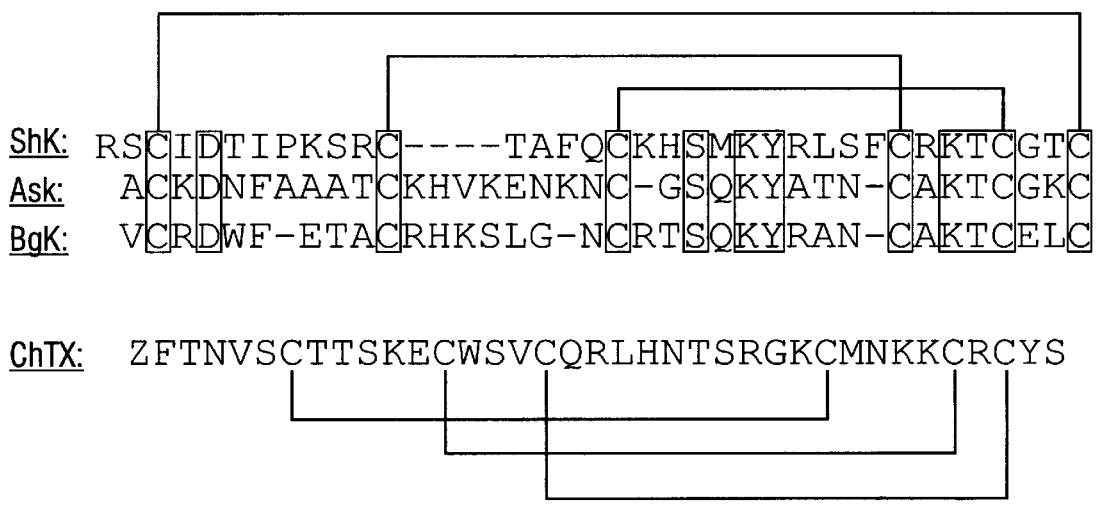

FIG. 13. Sequence of wild-type ShK toxin (Karilssori et al., 1992), BgK toxin (Aneiros et al., 1993; revised, Karlsson et al, 1992), AsK (Schweitz et al., 1995) and ChTX (Sugg et al., 1990).

Figure 14A:
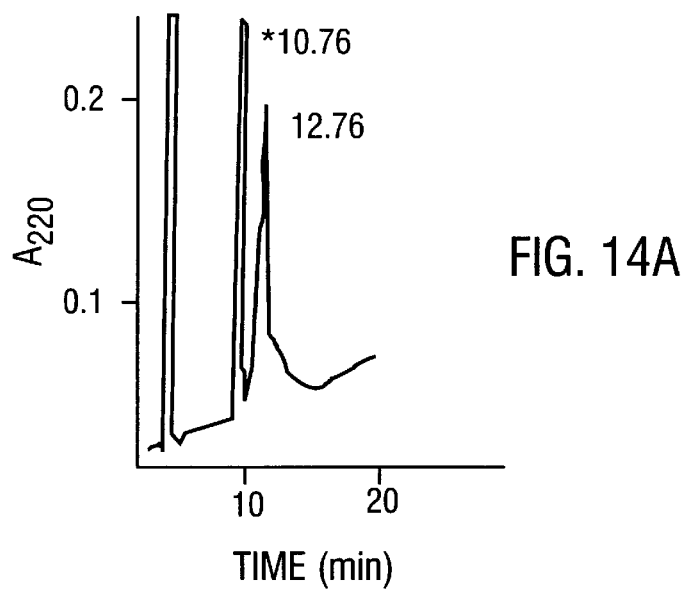

FIG. 14A. RP-HPLC analysis of the oxidative folding of crude wild-type ShK. HPLC conditions were as follows: a linear gradient of aqueous acetonitrile from 5 to 45% in 20 min at a flow rate of 1.5 ml/min on a Vydac $C_{18}$ column (300 Å; 0.46×25 cm).

Figure 14B:
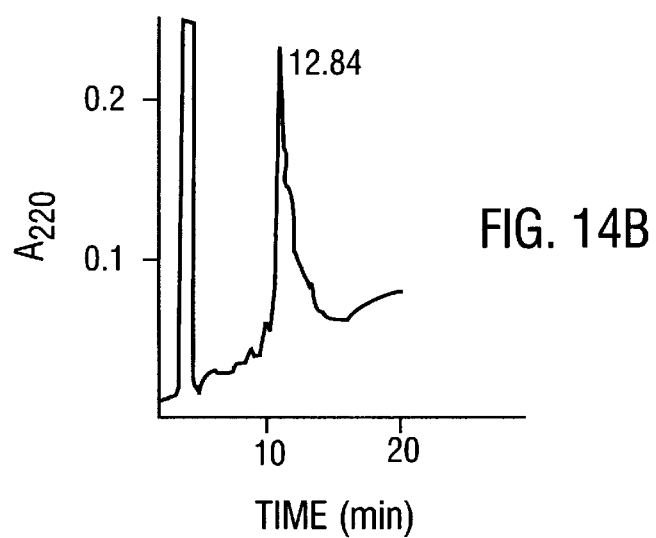

FIG. 14B. RP-HPLC analysis of the oxidative folding of crude ShK D5N. HPLC conditions were as follows: a linear gradient of aqueous acetonitrile from 5 to 45% in 20 min at a flow rate of 1.5 ml /min on a Vydac $C_{18}$ column (300 Å; 0.46×25 cm).

Figure 14C:
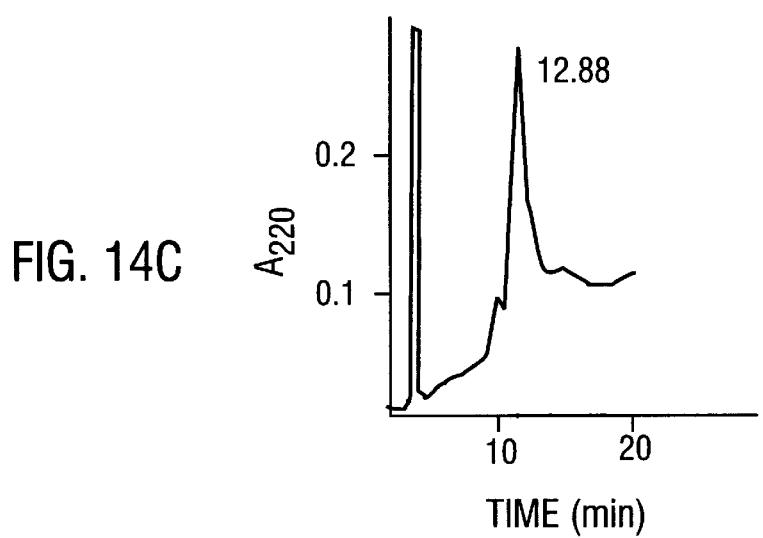

FIG. 14C. RP-HPLC analysis of the oxidative folding of crude ShK K30A. HPLC conditions were as follows: a linear gradient of aqueous acetonitrile from 5 to 45% in 20 min at a flow rate of 1.5 ml/min on a Vydac $C_{18}$ column (300 Å; 0.46×25 cm).

Figure 15:
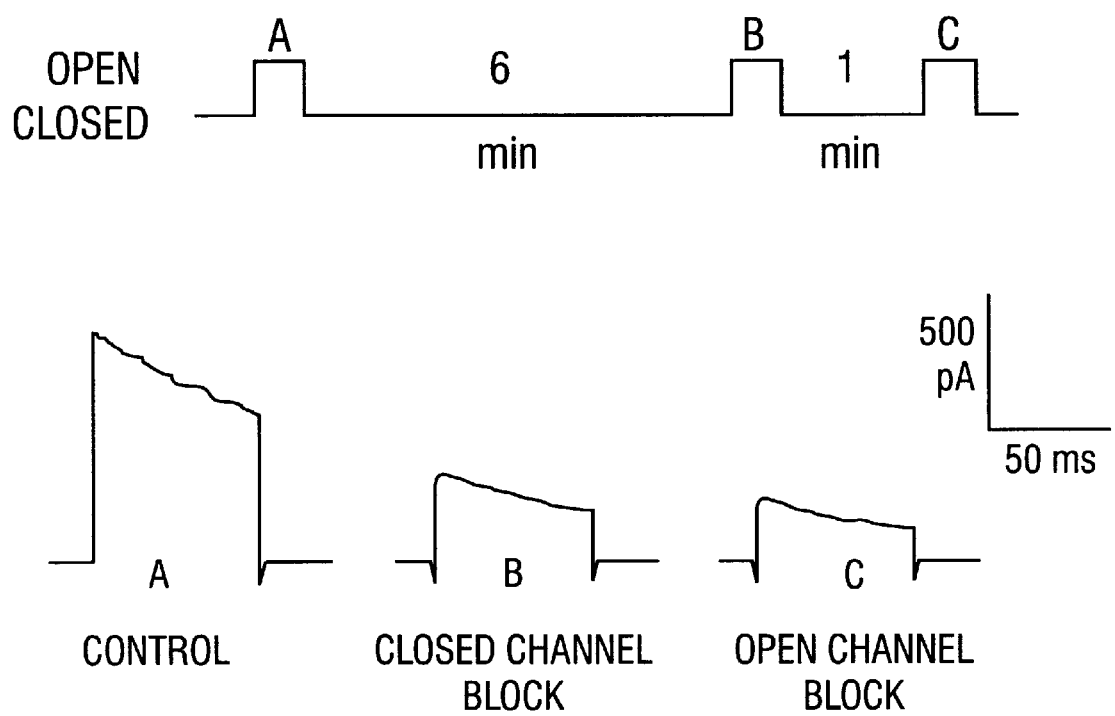

FIG. 15. Block of Kv1.3 current by ShK toxin. The voltage protocol is illustrated above the current traces Holding potential was −80 mV ani test potential was +30 mV. Current traces are shown immediately prior to exposure to ShK toxin (100 pM) and following 6 minutes after exposure with no pulsing (closed channel block). Open channel block was assessed by applying an additional pulse 1 minute later.

Figure 16A:
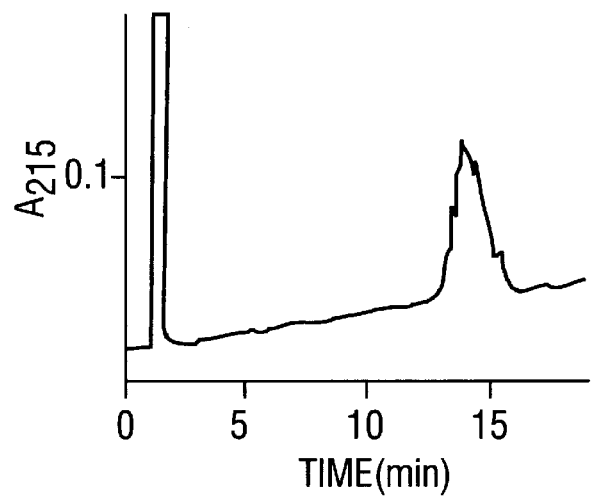

FIG. 16A. Analysis of oxidative folding of ShK toxin analogs by RP-HPLC. Each trace represents an injection of 50 μg total peptide onto a ODS column (Vydac 0.46×25 cm) developed with linear gradient of aqueous acetonitrile gradient from 5 to 45% in 20 min with a flow rate of 1.5 ml/min. K30A after folding for 36 hr in the presence of air.

Figure 16B:
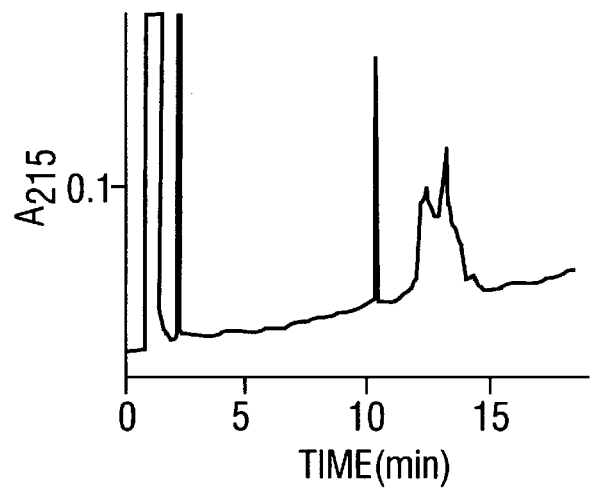

FIG. 16B. Analysis of oxidative folding of ShK toxin analogs by RP-HPLC. Each trace represents an injection of 50 μg total peptide onto a ODS column (Vydac 0.46×25 cm) developed with linear gradient of aqueous acetonitrile gradient from 5 to 45% in 20 min with a flow rate of 1.5 ml/min. K30A after folding for 18 hr in the presence of 1 mM reduced and oxidized glutathione.

Figure 16C:
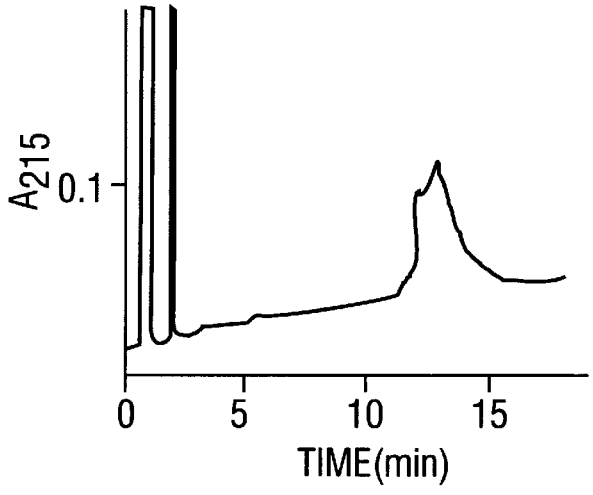

FIG. 16C. Analysis of oxidative folding of ShK toxin analogs by RP-HPLC. Each trace represents an injection of 50 μg total peptide onto a ODS column (Vydac 0.46×25 cm) developed with linear gradient of aqueous acetonitrile gradient from 5 to 45% in 20 min with a flow rate of 1.5 m/min. D5A after folding for 36 hr in the presence of 1 mM reduced and oxidized glutathione.

Figure 16D:
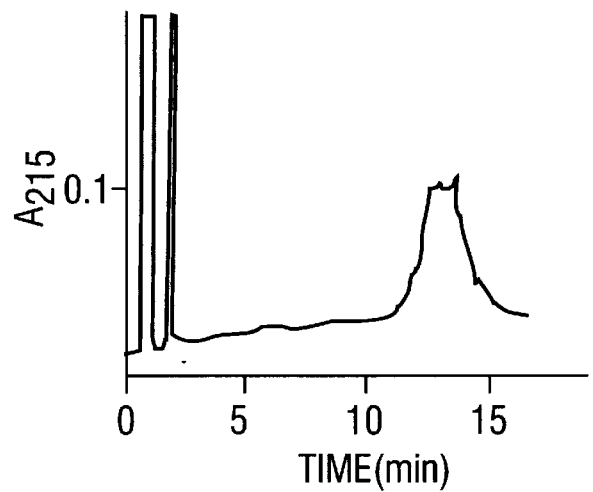

FIG. 16D. Analysis of oxidative folding of ShK toxin analogs by RP-HPLC. Each trace represents an injection of 50 μg total peptide onto a ODS column (Vydac 0.46×25 cm) developed with linear gradient of aqueous acetonitrile gradient from 5 to 45% in 20 min with a flow rate of 1.5 ml/min. D5E after folding for 36 hr in the presence of 1 mM reduced and oxidized glutathione.

Figure 16E:
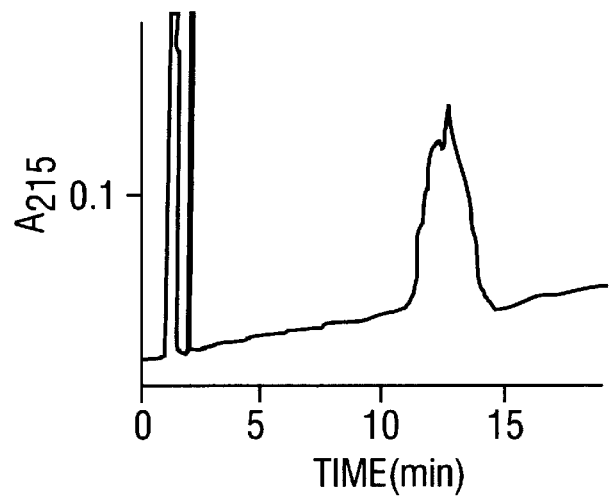

FIG. 16E. Analysis of oxidative folding of ShK toxin analogs by RP-HPLC. Each trace represents an injection of 50 μg total peptide onto a ODS column (Vydac 0.46×25 cm) developed with linear gradient of aqueous acetonitrile gradient from 5 to 45% in 20 min with a flow rate of 1.5 ml/min. H19A after folding for 36 hr in the presence of 1 mM reduced and oxidized glutathione.

Figure 16F:
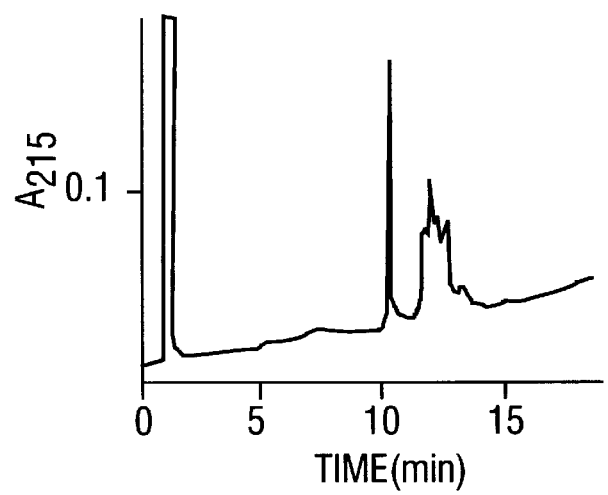

FIG. 16F. Analysis of oxidative folding of ShK toxin analogs by RP-HPLC. Each trace represents an injection of 50 μg total peptide onto a ODS column (Vydac 0.46×25 cm) developed with linear gradient of aqueous acetonitrile gradient from 5 to 45% in 20 min with a flow rate of 1.5 ml/min. H19K after oxidative folding for 18 hr in the presence of air.

Figure 17:
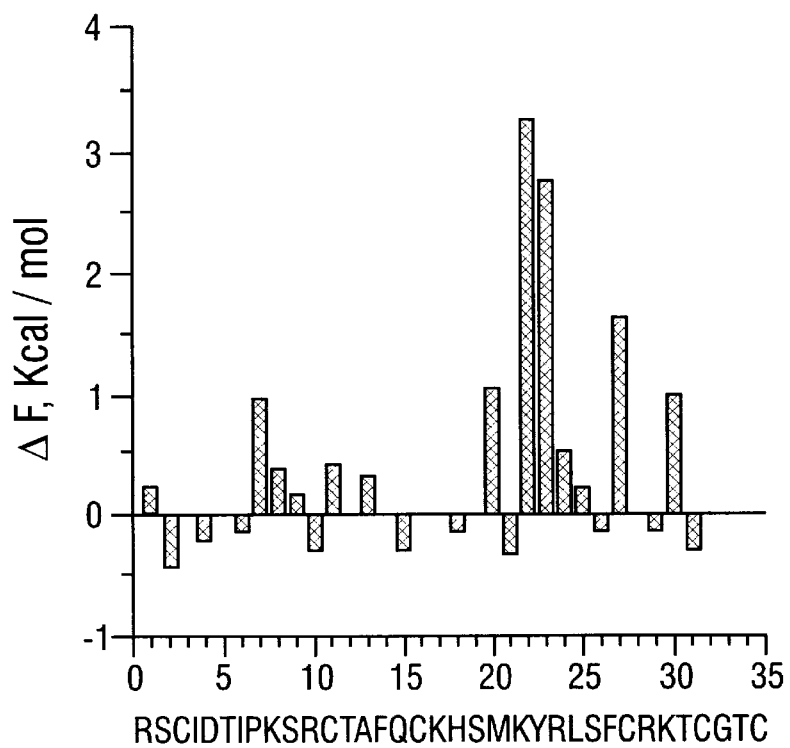

FIG. 17. Free energy difference of binding for ShK toxin analog as determined by displacement of $^{125}$I-dendrotoxin binding to rat brain membranes of ShK analogs. The free energy difference of binding was calculated as $\Delta F = RT \ln$ ($IC_{50}$ Analog$IC_{50}$ WT-Toxin) (R=1.987 cal/mole, T=295° K.). Amino acid residues substituted with Ala are shown in single letter code. The analogs with a single substitution for Cys (C) or Gly (G) were not synthesized in the present study as these residues were expected to be important for proper folding of the toxin. Data for Ala substitutions at positions Arg1, Phe15, Lys18, Lys22 and Arg24 were previously reported (Pennington et al., 1966), but here have been converted to free energy values and included to make this "Ala scan" analysis complete.

Figure 18:
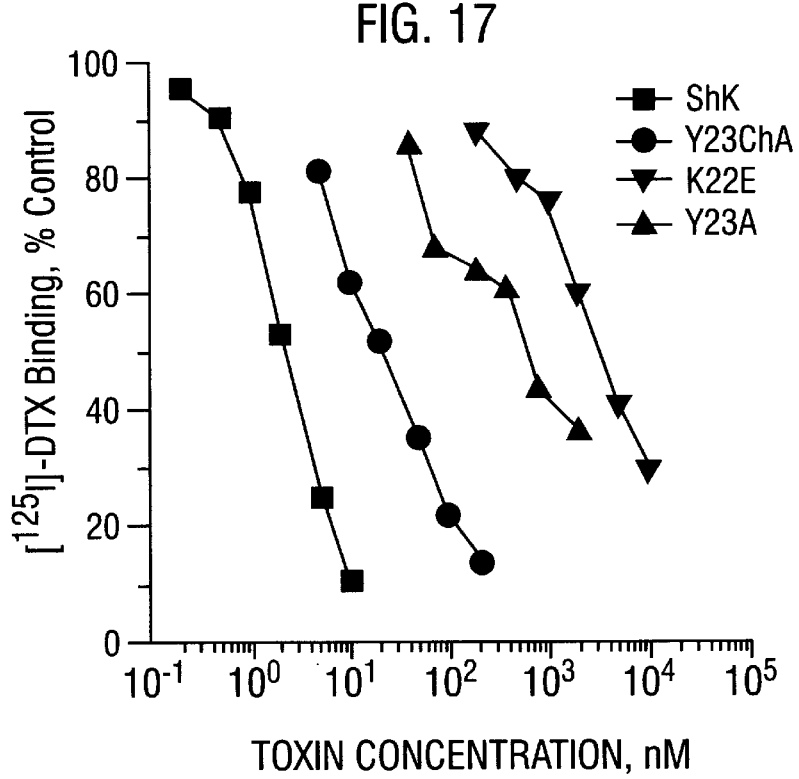

FIG. 18. Displacement of 125I-DTX (1 nM) specific binding to rat brain membranes by ShK toxin and several analogs.

Figure 19:
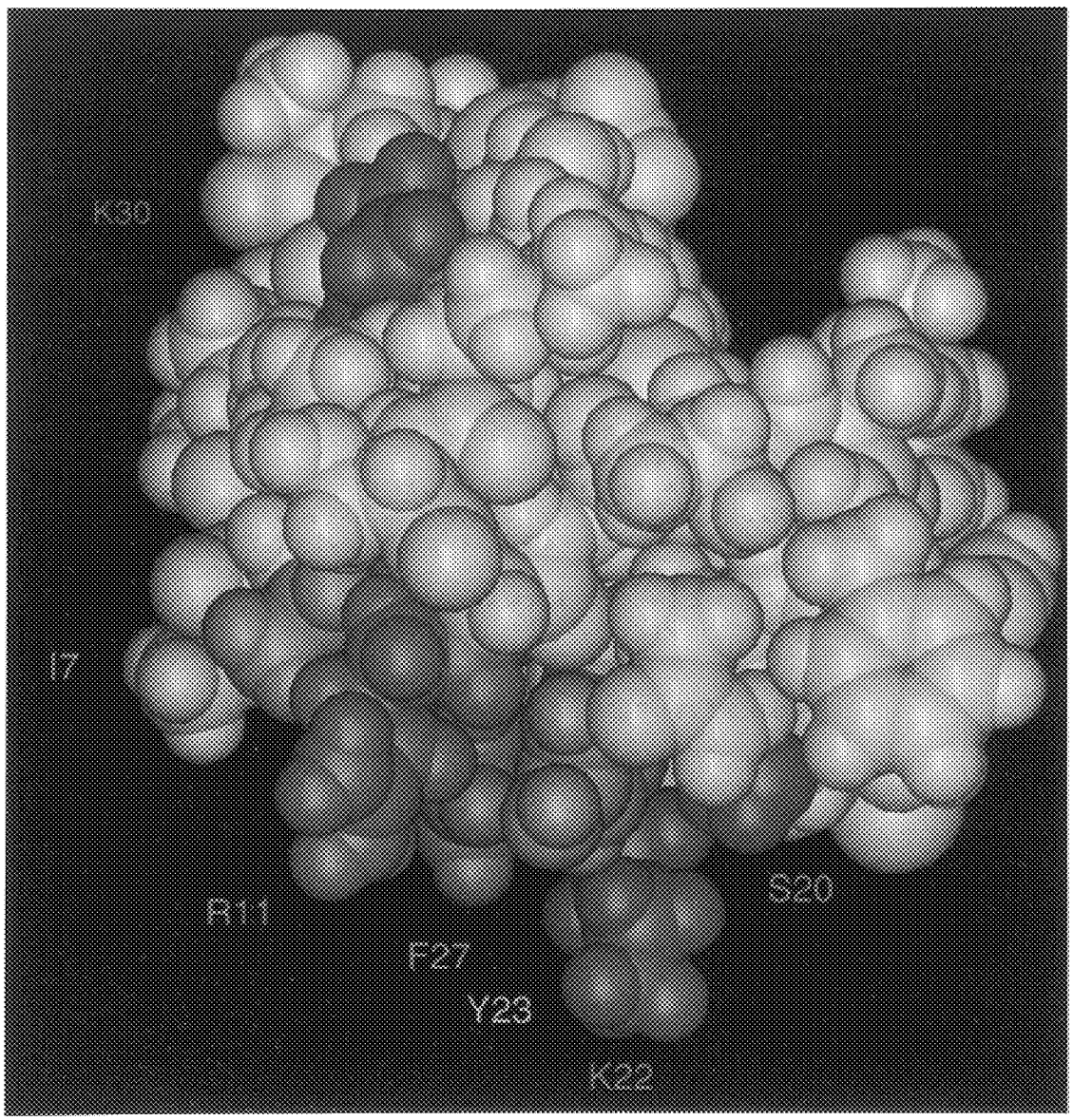

FIG. 19. CPK surface diagram of ShK toxin (10) with the side chains of Ile7 (light green), Arg11 (cyan), Ser20 (dark green), Lys22 (blue), Tyr23 (magenta), Phe27 (orange) and Lys30 (blue) highlighted. CPK surface diagram of ShK toxin was generated from the 2 D 1 H NMR spectra as described in Tudor, et al.

FIG. 20. Amino acid sequence and disulfide pairings of ShK toxin peptides.

Figure 21:
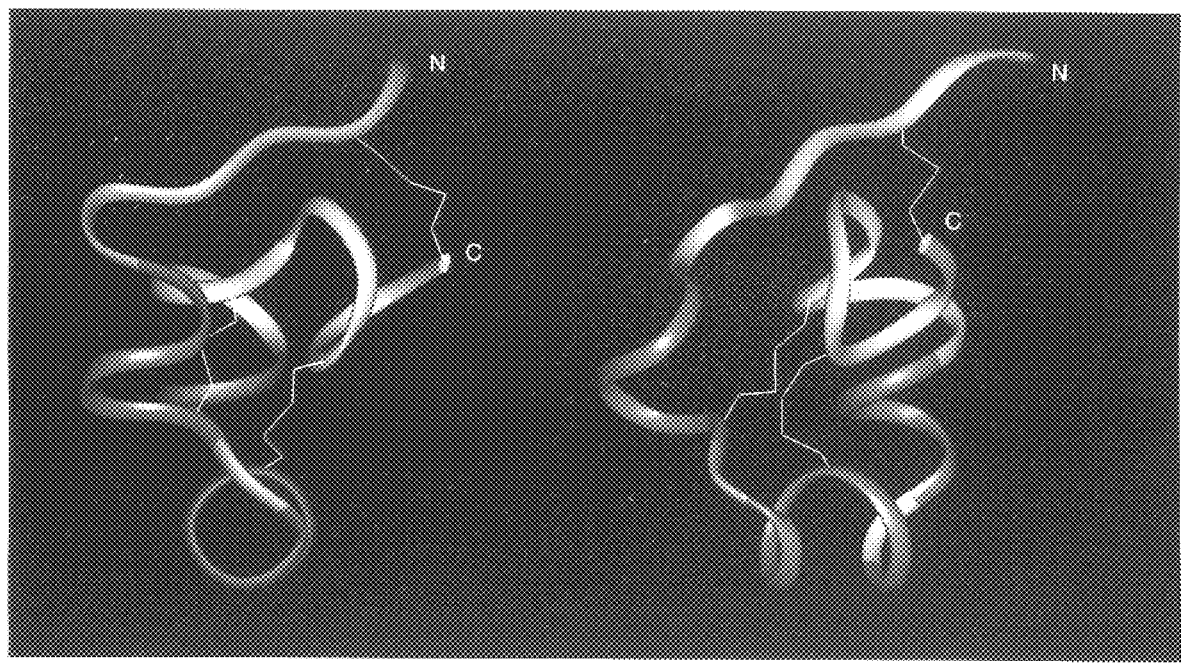

FIG. 21. Ribbon diagram showing backbone structure of ShK toxin (Tudor et al., 1996).

Figure 22:
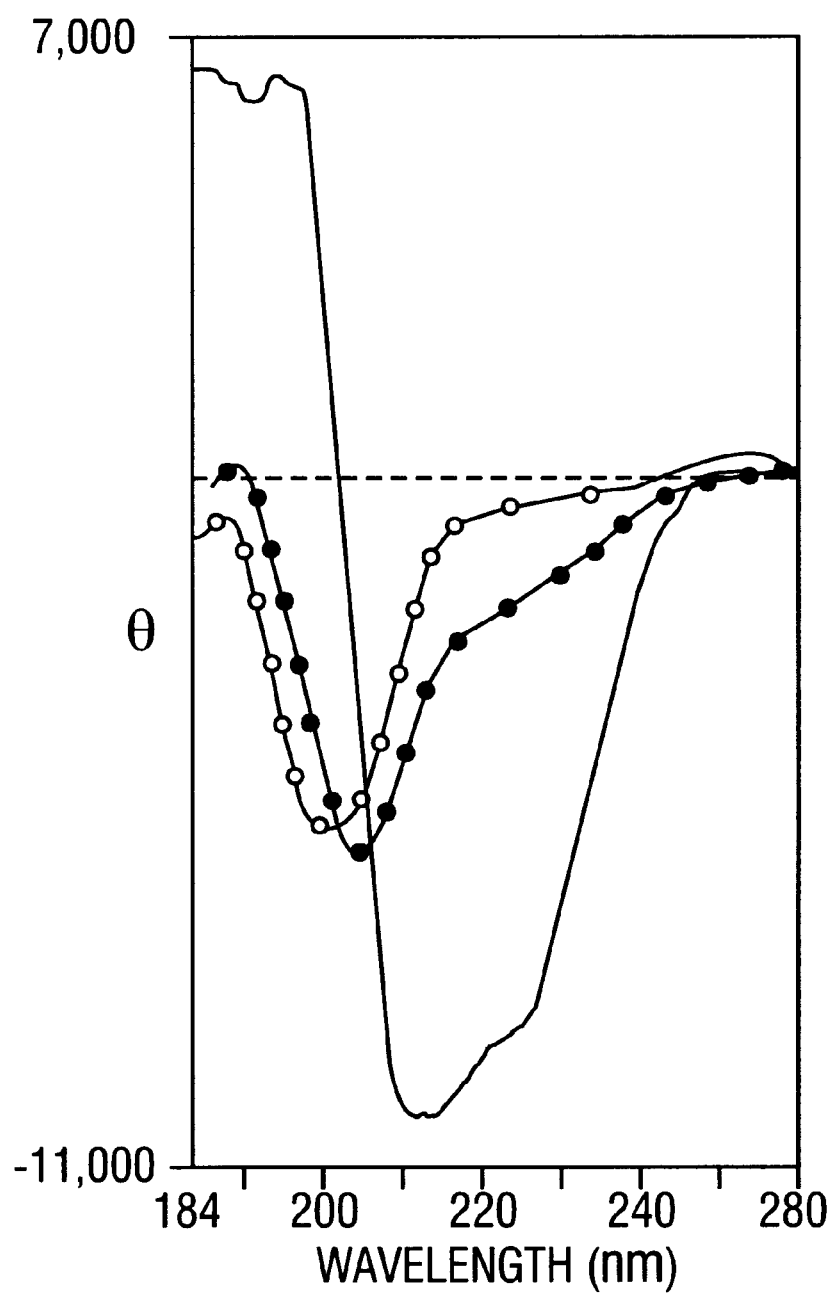
Figure 23A:
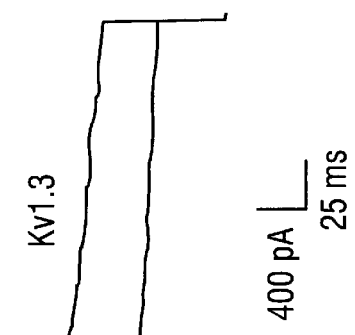
Figure 23B:
Figure 23C:
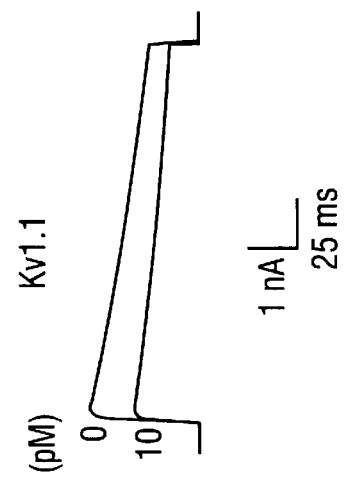
Figure 23D:
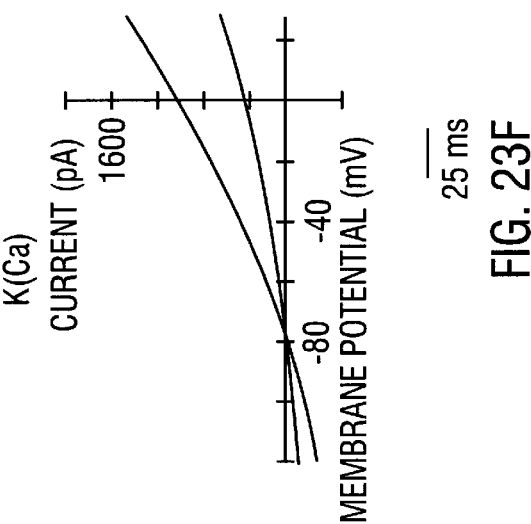
Figure 23E:
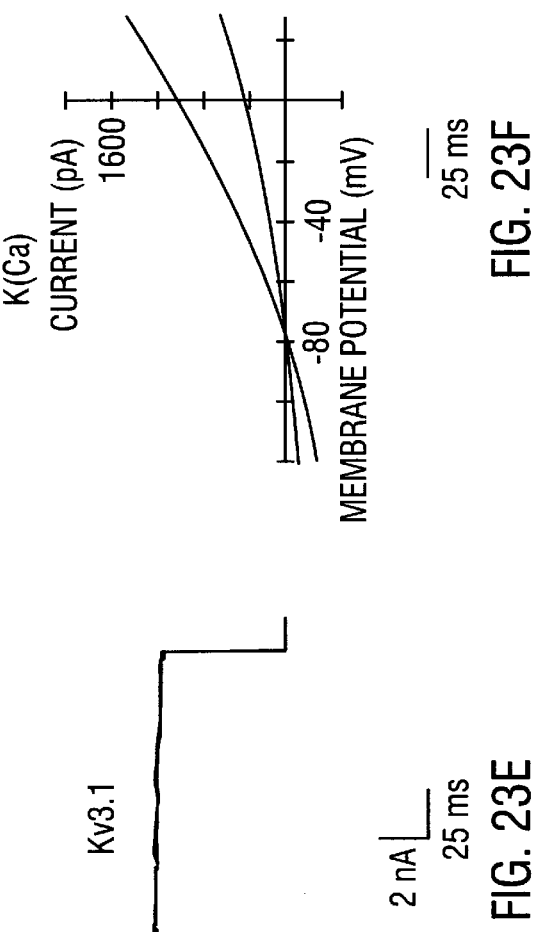
Figure 23F:

FIG. 22. CD spectra of ShK toxin (−), and its monocyclic (o) and the bicyclic analogs (●).

FIG. 23. Binding affinity of ShK toxin for K channels (Kv1.1, Kv1.2, Kv1.3, Kv1.5, Kv3.1) and membrane potential data (K(Ca)).

FIG. 24. Comparative data for ShK and ShK, K22DAP binding affinity for K channel Kv1.3.

FIG. 25. Comparative binding data for ShK toxin and ShK, K22DAP for Kv1.1.

DESCRIPTION OF ILLUSTRATIVE EMBODIMENTS

Definitions

The following words and phrases have the meanings set forth below.

Expression: The combination of intracellular processes, including transcription and translation undergone by a coding DNA molecule such as a structural gene to produce a polypeptide.

Promoter: A recognition site on a DNA sequence or group of DNA sequences that provide an expression control element for a structural gene and to which RNA polymerase specifically binds and initiates RNA synthesis (transcription) of that gene.

Structural gene: A gene that is expressed to produce a polypeptide.

Transformation: A process of introducing an exogenous DNA sequence (e.g., a vector, a recombinant DNA molecule) into a cell or protoplast in which that exogenous DNA is incorporated into a chromosome or is capable of autonomous replication.

Transformed cell: A cell whose DNA has been altered by the introduction of an exogenous DNA molecule into that cell.

Transgenic cell: Any cell derived or regenerated from a transformed cell or derived from a transgenic cell.

Vector: A DNA molecule capable of replication in a host cell and/or to which another DNA segment can be operatively linked so as to bring about replication of the attached segment. A plasmid is an exemplary vector.

Probes and Primers

In another aspect, DNA sequence information provided by the invention allows for the preparation of relatively short DNA (or RNA) sequences having the ability to specifically hybridize to gene sequences of the selected polynucleotides disclosed herein. In these aspects, nucleic acid probes of an appropriate length are prepared based on a consideration of a selected ShK toxin gene sequence, e.g., a sequence such as that shown in SEQ ID NO:1. The ability of such DNAs and nucleic acid probes to specifically hybridize to a ShK toxin-encoding gene sequence lends them particular utility in a variety of embodiments. Most importantly, the probes may be used in a variety of assays for detecting the presence of complementary sequences in a given sample.

In certain embodiments, it is advantageous to use oligonucleotide primers. The sequence of such primers is designed using a polynucleotide of the present invention for use in detecting, amplifying or mutating a defined segment of a ShK toxin gene from *S. helianthus* using PCR™ technology. Segments of related ShK toxin genes from other species may also be amplified by PCR™ using such primers.

To provide certain of the advantages in accordance with the present invention, a preferred nucleic acid sequence employed for hybridization studies or assays includes sequences that are complementary to at least a 14 to 30 or so long nucleotide stretch of a ShK toxin-encoding sequence, such as that shown in SEQ ID NO:1. A size of at least 14 nucleotides in length helps to ensure that the fragment will be of sufficient length to form a duplex molecule that is both stable and selective. Molecules having complementary sequences over stretches greater than 14 bases in length are generally preferred, though, in order to increase stability and selectivity of the hybrid, and thereby improve the quality and degree of specific hybrid molecules obtained. One will generally prefer to design nucleic acid molecules having gene-complementary stretches of 14 to 20 nucleotides, or even longer where desired. Such fragments may be readily prepared by, for example, directly synthesizing the fragment by chemical means, by application of nucleic acid reproduction technology, such as the PCR™ technology of U.S. Pat. Nos. 4,683,195, and 4,683,202, herein incorporated by reference, or by excising selected DNA fragments from recombinant plasmids containing appropriate inserts and suitable restriction sites.

Expression Vectors

The present invention contemplates an expression vector comprising a polynucleotide of the present invention. Thus, in one embodiment an expression vector is an isolated and purified DNA molecule comprising a promoter operatively linked to a coding region that encodes a polypeptide of the present invention, which coding region is operatively linked to a transcription-terminating region, whereby the promoter drives the transcription of the coding region.

As used herein, the term "operatively linked" means that a promoter is connected to a coding region in such a way that the transcription of that coding region is controlled and regulated by that promoter. Means for operatively linking a promoter to a coding region are well known in the art.

In a preferred embodiment, the recombinant expression of DNAs encoding the ShK toxins of the present invention is preferable in a Stichodactyla host cell, such as *S. helianthus*. Promoters that function in bacteria are well-known in the art. An exemplary and preferred promoter for the Stichodactyla ShK toxins include any of the known ShK toxin gene promoters, including the ShK gene promoters. Alternatively, mutagenized or recombinant ShK toxin-encoding gene promoters may be engineered by the hand of man and used to promote expression of the novel gene segments disclosed herein.

In an alternate embodiment, the recombinant expression of DNAs encoding the ShK toxins of the present invention is performed using a transformed Gram-negative bacterium such as an *E. coli* or Pseudomonas spp. host cell. Promoters which function in high-level expression of target polypeptides in *E. coli* and other Gram-negative host cells are also well-known in the art.

The choice of which expression vector and ultimately to which promoter a polypeptide coding region is operatively linked depends directly on the functional properties desired, e.g., the location and timing of protein expression, and the host cell to be transformed. These are well known limitations inherent in the art of constructing recombinant DNA molecules. However, a vector useful in practicing the present invention is capable of directing the expression of the polypeptide coding region to which it is operatively linked.

RNA polymerase transcribes a coding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA).

Means for preparing expression vectors are well known in the art. Expression (transformation vectors) used to transform plants and methods of making those vectors are described in U.S. Pat. Nos. 4,971,908, 4,940,835, 4,769,061 and 4,757,011, the disclosures of which are incorporated herein by reference. Those vectors can be modified to include a coding sequence in accordance with the present invention.

A variety of methods has been developed to operatively link DNA to vectors via complementary cohesive termini or blunt ends. For instance, complementary homopolymer tracts can be added to the DNA segment to be inserted and to the vector DNA. The vector and DNA segment are then joined by hydrogen bonding between the complementary homopolymeric tails to form recombinant DNA molecules.

Immunosuppressants

Immunosuppressants such as cyclosporin and FK506 exhibit severe side effects which limit their therapeutic use. Cyclosporin's side effects are due to the interaction of this drug with the protein cyclophilin which is present in many different tissues. Similarly, FK-506 causes toxicity because its target protein, FK-binding protein, is found in many different tissues. There has therefore been a major effort to identify novel immunosuppressants without serious side-effects, the goal being to identify novel targets expressed principally in T-lymphocytes.

The Kv1.3 potassium channel in T-lymphocytes plays an important role in regulating T-cell activation. Expression of this gene is highly restricted to T-cells, although Kv1.3 mRNAs are also detected faintly in brain, β-lymphocytes, microglia, macrophages, osteoclasts and platelets; only in T-cells does this channel dominate the membrane potential, and therefore, only in T-cells does Kv1.3-blockade have functional consequences. Due to its distinct mechanism and restricted tissue distribution, a Kv1.3 blocker would not likely display the toxic side-effects of cyclosporin and FK-506, and therefore may prove useful for treatment of chronic autoimmune diseases as well as transplantation therapy.

Recent studies by scientists at Merck Sharpe and Dohme have shown that the potent Kv1.3 peptide-antagonist, margatoxin (MgTX), is effective in suppressing the immune response in animal models (pig) and has minimal side-effects. This peptide is however, not specific for Kv1.3, and blocks the closely related Kv1.2 channel with similar potency. Since the Kv1.2 channel is expressed in the heart and brain, its blockade might have serious deleterious effects. The inventors have therefore searched for other novel peptides that might be truly selective for Kv1.3.

The sea-anemone toxin, ShK, is known to potently block the Kv1.3 channel. The inventors assessed the selectivity of this toxin on a panel of cloned Kv channels and found that ShK blocked Kv1.1 with similar potency as Kv1.3; other related channels were >100-fold less sensitive to the ShK toxin (Table 8). Although the native toxin is not specific for the lymphocyte channel, the inventors screened ShK mutants using a panel of cloned channels to identify a Kv1.3-selective antagonist. These results are described in Example 13.

Ion Channel Toxins:3D Structures and Channel-Binding Surfaces

Polypeptide ion channel toxins are proving to be valuable therapeutic leads in the treatment of a range of conditions. Among their advantages are high potency, good target specificity, high solubility and rapid onset of action. As they are often small proteins cross-linked by several disulfides, they generally also have quite stable structures in solution, which are readily determined using $^1$H NMR spectroscopy. Once the solution structure has been solved it is possible to map onto that structure the likely channel binding surface, identified initially by alanine scanning, then characterized further by additional residue substitutions. If a model of the ion channel is also available then possible docking interactions of the toxin can be tested by complementary mutagenesis. This information provides the basis for the design of smaller peptidic analogues of the toxin, and eventually of peptidomimetic analogs.

ShK toxin is a potent blocker of Kv1.3 potassium channels in T-lymphocytes. The solution structure of ShK toxin consists of two helices and a series of turns, making it quite different from scorpion toxins that interact with the same channel (Tudor et al., 1996). Key residues for channel binding have been defined using synthetic analogues. For both toxins the structural effects of disulfide bond removal and truncation have been investigated as a first step towards development of a peptidic analogue.

ShK Methods of Synthesis

Synthesis of a peptide via solid-phase methods includes the use of a solid-phase resin such as but not limited to polystyrene, polyacrylamide, cotton or other stable polymer. Derivatization of the solid-phase resin with a suitable handle such as chlorotrityl chloride, 2-chlorotrityl chloride, hydroxymethylphenyl, Sasrin as a means to produce the C-terminal acid functionality. A C-terminal amide may also be prepared as a means of proteolytic stabilization via a resin linker such as but not limited to 4-(2', 4'-dimethoxyphenyl-Fmoc-aminomethyl)-phenoxymethyl group.

Chain assembly shall include any of the protecting group strategies where the a-amino protecting group is either t-butyloxycarbonyl (Boc) or 9-fluorenylmethyloxycarbonyl. Side chain protecting groups shall include any combination of either no protecting groups or t-butyl, benzyl, trityl, methyltrityl, benzyl-methylbenzyl, tosyl, benzyloxymethyl, t-butyloxycarbonyl, 2-chlorobenzyl, 2-bromobenzyl, methoxybenzyl, formyl, acetamidomethyl, pentamethylchroman sulfonyl, pentamethyldihydrobenzofuran-sulfonyl, nitro for sidechain amines, guandines, phenols, alcohols, acids, imidazoles, thiols, and indoles. This includes side chain protecting groups which could be invented which accomplish the same goal of eliminating side chain reactions during primary chain assembly.

Synthesis of the amide bond may be accomplished by using any of the acid activation methods including but not limited to symmetrical anhydrides (carbodiimide), HOBT esters, acyl fluorides, uronium activators such as but not limited to TBTU, HATU or HBTU, phosphonium activators such as but not limited to BOP, PyBOP, PyBrOP. These are all methods of activation of the carboxyl group which those practicing the art of peptide synthesis would be expected to know.

Synthesis of analog structures which include substitution of unnatural amino acids into the sequence of ShK may also be useful for certain embodiments of the invention. Synthesis of ShK via convergent methods whereby fragments of the peptide are assembled in a fashion whereby the ultimate product is ShK or a related toxin analog. Final cleavage and deprotection and folding of the toxin may be but not limited to either HF or TFA depending on the strategy employed for synthesis. Disulfide bond formation includes any orthagonal approach where differential Cys protection could be used to position the disulfide bonds in the correct C3–C35, C12–C28 and C17–C32 linkage. Also included would be any oxidative folding procedure wherein the same disulfide array is realized via air oxidation or glutathione mediated shuffling reaction.

In order to produce a peptide with a higher half life in vivo, analog structures of ShK whereby key proteolytic digestion sites may be substituted to reduce protease susceptibility. This may include replacement or substitution of nonessential residues with conservative isosteric replacements (e.g., Lys to Lys(acetyl) or Gln) and or neutral replacements (Ala). Also, acetylation of the N-terminus or amidation of the C-terminus may provide stability from exopeptidases. Also, endopeptidase sites may have an Na-methylated substitution to reduce proteolytic degradation.

Internal or external truncations may also be prepared from ary of the disclosed peptides. These may include removing one or more residues from either the C-terminus or N-terminus or removal of one or more internal non-essential residues or sequence.

Low Molecular Weight Analogues of ShK Toxin

The three-dimensional structure of ShK toxin in aqueous solution (Tudor et al., 1996) consists of two short α-helices (residues 14–19 and 21–24) and a number of reverse turns. A number of the residues essential for ShK binding to the T-lymphocyte (Kv1.3) and rat brain $K^+$ channels have been identified using analogues made by peptide synthesis (Pennington et al., 1996a, Pennington et al., 1996b; Pennington et al., 1997). It appears that Lys22 and Tyr23, which are part of the second helix, are important for binding to both types of K$^+$ channel, while Arg11 is one of the key residues responsible for preferential binding to Kv1.3. These residues are on the same face of ShK toxin, making it practical to design and synthesize mimetics that present these residues in the bioactive conformation.

Two methods may be used to development of low molecular weight analogues of ShK toxin. The first is polypeptide minimization, where the size of a polypeptide is reduced in such a way that the amino acid residues important for activity are maintained in character and conformation even though much of the molecule may be deleted. This has the advantage that it can provide useful new analogues directly, possibly with improved pharmocokinetics and bioavailability. Moreover, it simplifies the task of identifying non-peptidic scaffolds for the development of peptidomimetics.

Minimization is achieved by compensating for the deleted intramolecular interactions of the native molecule (including disulfide bonds) by stabilizing the remaining structure. This may be done by stabilizing the local conformations of the two helices in ShK toxin (residues 14–19 and 21–24) then incorporating covalent links between them to maintain the bioactive spatial orientation found in the native toxin.

There are several proven ways of stabilizing helices. One is to incorporate lactam bridges between carboxyl-bearing residues (aspartate and glutamate) and lysine residues separated by three intervening residues in the amino acid sequence (Houston et al., 1995). This has been achieved for analogues of human growth hormone releasing factor (Felix et al., 1988) and the C-terminal helix of neuropeptide Y (Rist et al., 1996; Kirby et al., 1997). Other examples are found in Kemp et al. (1991), Chorev et al. (1993) and Kanmera et al. (1995). Further helix stabilization is afforded by incorporation of overlapping i to i+4 lactam bridges in the helix (Bracken et al., 1994), although it may be more difficult to incorporate two such bridges in ShK analogues without affecting the K-channel binding surface.

Another means of stabilizing helices involves positioning stereoisomers of Cys to enable formation of an i to i+4 disulfide bridge between the L-Cys and D-Cys residues (Krstenansky et al., 1988).

Having stabilised the two short helices of ShK toxin, the next step is to lock them into a conformation similar to that found in the native toxin structure. Several methods are possible to achieve this, including non-native disulfide bridges, linkage via 4-(aminomethyl)phenylacetic acid (AMPA) (Yu and Taylor, 1996) between amino- and carboxyl-bearing residues, or linkage via an alkanediyl chain between the side-chain nitrogen atoms of glutamine residues (Phelan et al., 1997).

The remaining requirement is to initiate the first helix while at the same time making provision for inclusion of a functional group equivalent to Arg11 of the native toxin. Helical initiators derived from aspartic acid and glutamic acid are known (Meara et al., 1995). Another way to achieve helix initiation is to retain the reverse turn involving residues 9–12 in the native toxin or to incorporate a mimetic for this turn (Zhang et al., 1996; Kieber-Emmons et al., 1997). The turn mimetic could then be suitably functionalised to include a side-chain guanidino group to mimic Arg 11.

A bioactive, minimized peptidic analogue of ShK toxin may be further modified by inclusion of selected D-amino acids or by synthesis of a retro-inverso analogue, where all residues are D-handed and the amino acid sequence is reversed (Jameson et al., 1994; Juvvadi et al., 1996). Such modifications are expected to further increase its stability in vivo.

The second major approach to the development of low molecular weight analogues of ShK toxin is to generate non-peptidic (peptidomimetic) analogues. In these studies, analogs of ShK toxin are designed and synthesized based on non-peptidic scaffolds which contain key functional groups from the potassium channel binding surface of the parent polypeptide. Conformationally-directed database searches are undertaken to identify potential lead compounds from existing chemical libraries. Potential candidates are identified, including some which present the key functional groups in the appropriate conformation and some of which require synthetic modification. Using these methods, one may prepare novel ShK toxin analogs that are largely or entirely non-peptidic in nature and which display selectivity for particular target tissues.

There are many examples where naturally occurring low molecular weight, non-peptidic compounds have been shown to mimic or antagonise polypeptide or protein ligands. Similarly, peptidomimetic compounds have been designed and synthesized for a number of therapeutically relevant polypeptides. For example, a loop present on the CD4 receptor which binds to HIV gp120 protein (Chen et al., 1992). This compound effectively blocked gp120 binding to CD4 receptor at low micromolar concentrations and effectively reduces syncytium formation 50% at 250 $\mu$/ml. Another example is FTI-276, a mimetic of the C-terminal region of the Ras protein that is a potent blocker of oncogenic Ras signaling (Lemer et al., 1995).

Compounds showing a degree of similarity to the ShK pharmacophore are tested for K-channel binding, and those having binding affinity constitute valuable new leads, which may be further modified with the aim of improving binding affinity and channel sub-type specificity.

Animal Models of Autoimmune Diseases and Transplant Rejection

Over the years, several animal models of autoimmune diseases have been developed. It is important that animal models mimic as closely as possible the human disease and that they respond to treatment in similar ways as the human disease. Small animal models, such as rodents, are preferred because they are inexpensive, can be used in relatively high numbers, and have well characterized genetics. Although small animal models are often adequate models, large animals, particularly primates, are more suitable for some types of diseases. Small animals are less related to humans, but in many cases will react to treatment in the same way as humans do. While primates may be better models for some human diseases, they tend to be expensive, and handling can be difficult.

Psoriasiform Skin Disease

CD-18 deficient mice backcrossed onto a PL/J strain background have been used as an animal model for psoriasiform skin disease. Homozygotes for a null mutation in CD18 within the 129/Sv background are characterized by a mild leukocytosis, an impaired response to chemically-induced peritonitis, and delays in transplantation rejection (Wilson et al., 1993). Bullard et al. (1996) report that when the CD18 homozygote null mice are crossed to the PL/J strain of mice, the backcrossed mice develop an inflammatory skin disorder. The skin disease shows several histological and clinical similarities to human hyperproliferative inflammatory skin disorders, such as psoriasis (Camisa et al., 1994). These include epidermal hyperplasia, hyperkeratosis, parakeratosis, subcorneal microabscesses, lymphocyte exocytosis, and dilation of dermal capillaries.

Adult CD18 homozygous mice developed a progressive dermatitis characterized by erythema, alopecia, and scale and crust formation (Bullard et al., 1996). Visible signs of the disease first appeared as red, scaly skin on the ears, paws, tail, and facial area. Similar to the human disease, the CD18 null mice responded to administration of corticosteroids. Response to corticosteroids was assessed by daily subcutaneous injections of 20 µg of dexamethasone. Improvement was seen in all affected mice; dramatic improvement with disappearance of scales, crust, and erythema occurred after 2 weeks and was accompanied by regrowth of hair (Bullard et al., 1996). Acute withdrawal of the dexamethasone dose or reduction of the dose to 10 µg/day resulted in a severe exacerbation of the dermatitis (Bullard et al., 1996).

The gross morphology, anatomical distribution, disease course, and response to anti-inflammatory drug, such as dexamethasone, treatment are all features with similarity to human psoriasis and other inflammatory skin disorders. The Inflammatory skin disorder of the CD18 null PL/J mice has generally been accepted as a model of dermatitis because of its similarities to human psoriasis and autoimmune skin disease.

Inflammatory Bowel Disease

An animal model for inflammatory bowel disease is described by Leach et al.(1996). In this study, chronic inflammation develops spontaneously in the large intestine of C.B-17 scid mice restored with the $CD45RB^{high}$ subset of CD4+T cells obtained from normal BALB/c mice. The changes in the large intestine of these mice are similar to those seen in patients with idiopathic inflammatory bowel disease (Crohn's disease and ulcerative colitis). This murine model appears to be useful for studying mucosal immunoregulation as it relates to the pathogenesis and treatment of chronic inflammatory bowel diseases in the large intestine of human patients (Leach et al., 1996).

CB-17 scid mice injected with $CD45RB^{high}$ CD4+T cells from BALB/c mice consistently develop chronic inflammatory and epithelial lesions that extended profusely from the cecum to the rectum (Leach et al., 1996). Morphological features in the large intestine of these mice are similar to those seen in the colon of human patients with Crohn's Disease or ulcerative colitis (Leach et al, 1996). Similarly, these mice seem to have immunopathological findings similar to those found in patients with CD or UC. Therefore, this model provides an excellent system to test the efficacy of anti-immune or anti-inflammatory compositions, such as the polypeptides of the present invention, for treating Crohn's disease or ulcerative colitis.

Experimental Autoimmune Encephalomyelitis (Multiple Sclerosis)

Experimental autoimmune encephalomyelitis (EAE) describes a group of inflammatory diseases of the central nervous system (CNS) that are induced in susceptible animals by immunization with myelin antigens or by adoptive transfer of sensitized T-cells to syngeneic recipients (Alvord et al., 1984; Pettinelli et al., 1985). In inbred rodents, chronic and relapsing remitting forms of EAE that have been described resemble human multiple sclerosis (MS) (Zamvil et al., 1985; McFarlin et al., 1974; Raine et al., 1984). EAE has served in the testing of scores of therapies for MS, yet applicacy has often not been a predictor of benefit in humans. Autogenetic differences between inbred rodents and outbred humans, have limited the usefulness of EAE as an MS model. EAE has been described in macaques, yet acute CNS lesions in these species are hyperacute, hemorrhagic and destructive, unlike those in MS (Alvord et al., 1979). Additionally, the outbred nature of non-human primates has limited their value as disease models, since adoptive transfer of genetically compatible T-cells between animals is valuable for illucidating the role of specific T-cell populations in EAE.

Massacesi et al. (1995, incorporated herein by reference) describe the induction and the characteristics of EAE in the common marmoset *Callithrix jachus*, a new world monkey. Actively induced EAE in *C. jachus* is characterized clinically by mild neurological signs and a relapsing-remitting course, and pathologically by mononuclear cell infiltration primary, primary demyelination, and reactive gliosis. A further advantage of the use of the marmosets as the model for EAE is that they are born as naturally occurring bone marrow chimeras (Picus et al., 1985). While individual animals from multiple births arrive from separate ova that are fertilized independently, the placenta of the developing animals fuse, resulting in a cross-circulation of bone marrow-derived elements between the developing fetuses. Thus, while animals are genetically distinct, they share and are tolerant of each other's bone marrow-derived cell populations.

In this model, one is capable of adoptively transferring EAE by T-cell transfer between members of a chimeric set of twins. Acute and chronic EAE, created in a species whose immune and nervous system genes are phylogenetically close to those of humans, represents a unique disease model and may be useful in elucidating immune mechanisms of CNS demyelination. Furthermore, it provides an excellent system for testing the efficacy of compostions, such as the polypeptides of the present invention, at treating such disorders.

Transplantation Rejection

Transplantation of organs into a new host causes an immune response against the new organ, similar to autoimmune diseases. Thus, transplantation model systems in animals also are very useful in testing the efficacy of anti-inflammatory or autoimmune compounds, such as the polypeptides of the present invention. Animal transplantation models include a lung transplantation model in swine (Schmidt et al., 1997), a kidney transplantation model in swine (Granger et al., 1995), a kidney transplantation model in canines (Tanabe et al., 1994), and an intrasplenic hepatocyte transplantation model in canines (Benedetti et al., 1997).

Immunoassays

As noted, it is proposed that native and synthetically-derived peptides and peptide epitopes of the invention will find utility as immunogens, e.g., in connection with vaccine development, or as antigens in immunoassays for the detection of reactive antibodies. Turning first to immunoassays, in their most simple and direct sense, preferred immunoassays of the invention include the various types of enzyme linked immunosorbent assays (ELISAs), as are known to those of skill in the art. However, it will be readily appreciated that the utility of SHK-derived proteins and peptides is not limited to such assays, and that other useful embodiments include RIAs and other non-enzyme linked antibody binding assays and procedures.

In preferred ELISA assays, proteins or peptides incorporating ShK, rShK, or ShK-derived protein antigen sequences are immobilized onto a selected surface, preferably a surface exhibiting a protein affinity, such as the wells of a polystyrene microtiter plate. After washing to remove incompletely adsorbed material, one would then generally desire to bind or coat a nonspecific protein that is known to be antigenically neutral with regard to the test antisera, such as bovine serum albumin (BSA) or casein, onto the well. This allows for blocking of nonspecific adsorption sites on the immobilizing surface and thus reduces the background caused by nonspecific binding of antisera onto the surface.

After binding of antigenic material to the well, coating with a non-reactive material to reduce background, and washing to remove unbound material, the immobilizing surface is contacted with the antisera or clinical or biological extract to be tested in a manner conducive to immune complex (antigen/antibody) formation. Such conditions preferably include diluting the antisera with diluents such as BSA, bovine gamma globulin (BGG) and phosphate buffered saline (PBS)/Tween®). These added agents also tend to assist in the reduction of nonspecific background. The layered antisera is then allowed to incubate for, e.g., from 2 to 4 hours, at temperatures preferably on the order of about 25° to about 27° C. Following incubation, the antisera-contacted surface is washed so as to remove non-immunocomplexed material. A preferred washing procedure includes washing with a solution such as PBS/Tween®, or borate buffer.

Following formation of specific immunocomplexes between the test sample and the bound antigen, and subsequent washing, the occurrence and the amount of immunocomplex formation may be determined by subjecting the complex to a second antibody having specificity for the first. Of course, in that the test sample will typically be of human origin, the second antibody will preferably be an antibody having specificity for human antibodies. To provide a detecting means, the second antibody will preferably have an associated detectable label, such as an enzyme label, that will generate a signal, such as color development upon incubating with an appropriate chromogenic substrate. Thus, for example, one will desire to contact and incubate the antisera-bound surface with a urease or peroxidase-conjugatedanti-human IgG for a period of time and under conditions that favor the development of immunocomplex formation (e.g., incubation for 2 hours at room temperature in a PBS-containing solution such as PBS-Tween®).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonicacid (ABTS) and $H_2O_2$, in the case of peroxidase as the enzyme label. Quantitation is then achieved by measuring the degree of color generation, e.g., using a visible spectrum spectrophotometer.

ELISAs may be used in conjunction with the invention. In one such ELISA assay, proteins or peptides incorporating antigenic sequences of the present invention are immobilized onto a selected surface, preferably a surface exhibiting a protein affinity such as the wells of a polystyrene microtiter plate. After washing to remove incompletely adsorbed material, it is desirable to bind or coat the assay plate wells with a nonspecific protein that is known to be antigenically neutral with regard to the test antisera such as bovine serum albumin (BSA), casein or solutions of powdered milk. This allows for blocking of nonspecific adsorption sites on the immobilizing surface and thus reduces the background caused by nonspecific binding of antisera onto the surface.

Pharameceutical Compositions

The pharmaceutical compositions disclosed herein may be orally administered, for example, with an inert diluent or with an assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-releasepreparation and formulations.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral prophylaxis the polypeptide may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

The composition can be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Liposomes and Nanocapsules

In certain embodiments, the inventors contemplate the use of liposomes and/or nanocapsules for the introduction of particular peptides or nucleic acid segments into host cells. Such formulations may be preferred for the introduction of pharmaceutically-acceptable formulations of the nucleic acids, peptides, and/or antibodies disclosed herein. The formation and use of liposomes is generally known to those of skill in the art (see for example, Couvreur et al., 1977 which describes the use of liposomes and nanocapsules in the targeted antibiotic therapy of intracellular bacterial infections and diseases). Recently, liposomes were developed with improved serum stability and circulation half-times (Gabizon and Papahadjopoulos, 1988; Allen and Choun, 1987).

Nanocapsules can generally entrap compounds in a stable and reproducible way (Henry-Michelland et al., 1987). To avoid side effects due to intracellular polymeric overloading, such ultrafine particles (sized around 0.1 µm) should be designed using polymers able to be degraded in vivo. Biodegradable polyalkyl-cyanoacrylatenanoparticles that meet these requirements are contemplated for use in the present invention, and such particles may be are easily made, as described (Couvreur et al., 1977; 1988).

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500 Å, containing an aqueous solution in the core.

In addition to the teachings of Couvreur et al. (1988), the following information may be utilized in generating liposomal formulations. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. It often is difficult t o determine which mechanism is operative and more than one may operate at the same time.

Affinity Chromatography

Affinity chromatography is generally based on t he recognition of a protein by a substance such as a ligand or an antibody. The column material may be synthesized by covalently coupling a binding molecule, such as an activated dye, for example to an insoluble matrix. The column material is then allowed to adsorb the desired substance from solution. Next, the conditions are changed to those under which binding does not occur and the substrate is eluted. The requirements for successful affinity chromatography are:

1) that thematrix must specifically-adsorb the molecules of interest;

2) that other contaminants remain unadsorbed;

3) that the ligand must be coupled without altering its binding activity;

4) that the ligand must bind sufficiently tight to the matrix; and 5) that it must be possible to elute the molecules of interest without destroying them.

Therapeutic Kits Comprising ShK Compositions

A therapeutic kit comprising, in suitable container means, one or more ShK composition(s) of the present invention in a pharmaceutically acceptable formulation represent another aspect of the invention. The ShK composition(s) may comprise:

1) one or more ShK polypeptide;

2) one or more truncated ShK polypeptides;

3) one or more site-specifically or randomly mutated ShK polypeptides;

4) one or more ShK-encoded peptide epitopes, domains or motifs;

5) one or more antibodies which bind to native, truncated, site-specifically or randomly mutated ShKs, or ShK-encoded peptide epitopes, domains or motifs;

6) one or more nucleic acid segments encoding all or a portion of one or more ShK genes, These nucleic acid segments may encode native ShKs, truncated ShKs, site-specifically or randomly mutated ShKs, or ShK-derived peptide epitopes, domains or motifs, and may be either native, recombinant, or mutagenized DNA or RNA segments; or, alternatively, 7) a combination of one or more of the compositions 1) through 6).

The kit may comprise a single container means that contains the ShK composition(s). The container means may, if desired, contain a pharmaceutically acceptable sterile excipient, having associated with it, the ShK composition(s) and, optionally, a detectable label or imaging agent. The formulation may be in the form of a gelatinous composition (e.g., a collagenous composition), a powder, solution, matrix, lyophilized reagent, or any other such suitable means. In certain cases, the container means may itself be a syringe, pipette, or other such like apparatus, from which the ShK composition(s) may be applied to a tissue site, skin lesion, or wound area. However, the single container means may contain a dry, or lyophilized, mixture of one or more ShK composition(s), which may or may not require pre-wetting before use.

Alternatively, the kits of the invention may comprise distinct container means for each component. In such cases, one or more containers would contain each of the ShK composition(s), either as sterile solutions, powders, lyophilized forms. etc., and the other container(s) would include a matrix, solution, or other suitable delivery device for applying the ShK composition to the body, bloodstream, or to a tissue site, skin lesion, wound area, or other sites. Such delivery device may or may not itself contain a sterile solution, diluent, gelatinous matrix, carrier or other pharmaceutically-acceptable components.

The kits may also comprise a second or third container means for containing a sterile, pharmaceutically acceptable buffer, diluent or solvent. Such a solution may be required to formulate the SHK component into a more suitable form for application to the body, e.g., as a topical preparation, or alternatively, in oral, parenteral, or intravenous forms. It should be noted, however, that all components of a kit could be supplied in a dry form (lyophilized), which would allow for "wetting" upon contact with body fluids. Thus, the presence of any type of pharmaceutically acceptable buffer or solvent is not a requirement for the kits of the invention. The kits may also comprise a second or third container means for containing a pharmaceutically acceptable detectable imaging agent or composition.

The container means will generally be a container such as a vial, test tube, flask, bottle, syringe or other container means, into which the components of the kit may placed. The matrix and gene components may also be aliquoted into smaller containers, should this be desired. The kits of the present invention may also include a means for containing the individual containers in close confinement for commercial sale, such as, e.g., injection or blow-molded plastic containers into which the desired vials or syringes are retained.

Irrespective of the number of containers, the kits of the invention may also comprise, or be packaged with, an instrument for assisting with the placement of the ultimate matrix-gene composition within the body of an animal. Such an instrument may be a syringe, pipette, forceps, or any such medically approved delivery vehicle.

Methods for Generating an Immune Response

Also disclosed in a method of generating an immune response in an animal. The method generally involves administering to an animal a pharmaceutical composition comprising an immunologically effective amount of a peptide composition disclosed herein. Preferred peptide compositions include the ShK polypeptides disclosed in any of SEQ ID NO:2 to SEQ ID NO:61.

The invention also encompasses ShK and ShK-derived peptide antigen compositions together with pharmaceutically-acceptable excipients, carriers, diluents, adjuvants, and other components, as may be employed in the formulation of particular therapeutics.

The identification or design of suitable ShK epitopes, and/or their functional equivalents, suitable for use in immunoformulations, vaccines, or simply as antigens (e.g., for use in detection protocols), is a relatively straightforward matter. For example, one may employ the methods of Hopp, as enabled in U.S. Pat. No. 4,554,101, incorporated herein by reference, that teaches the identification and preparation of epitopes from amino acid sequences on the basis of hydrophilicity. The methods described in several other papers, and software programs based thereon, can also be used to identify epitopic core sequences. For example, Chou and Fasman (1974a,b; 1978a,b; 1979); Jameson and Wolf (1988); Wolf et al. (1988); and Kyte and Doolittle (1982) all address this subject. The amino acid sequence of these "epitopic core sequences" may then be readily incorporated into peptides, either through the application of peptide synthesis or recombinant technology.

It is proposed that the use of shorter antigenic peptides, e.g., about 15 to about 35, or even about 20 to 25 amino acids in length, that incorporate epitopes of one or more ShKs will provide advantages in certain circumstances, for example, in the preparation of vaccines or in immunologic detection assays. Exemplary advantages include the ease of preparation and purification, the relatively low cost and improved reproducibility of production, and advantageous biodistribution.

In general, the preferred immunodetection methods will include first obtaining a sample suspected of containing a ShK-reactive antibody, such as a biological sample from a patient, and contacting the sample with a first ShK or peptide under conditions effective to allow the formation of an immunocomplex (primary immune complex). One then detects the presence of any primary immunocomplexes that are formed.

Contacting the chosen sample with the ShK or peptide under conditions effective to allow the formation of (primary) immune complexes is generally a matter of simply adding the protein or peptide composition to the sample. One then incubates the mixture for a period of time sufficient to allow the added antigens to form immune complexes with, i.e., to bind to, any antibodies present within the sample. After this time, the sample composition, such as a tissue section, ELISA plate, dot blot or western blot, will generally be washed to remove any non-specifically bound antigen species, allowing only those specifically bound species within the immune complexes to be detected.

The detection of immunocomplex formation is well known in ihe art and may be achieved through the application of numerous approaches known to the skilled artisan and described in various publications, such as, e.g., Nakamuraet al. (1987), incorporated herein by reference. Detection of primary immune complexes is generally based upon the detection of a label or marker, such as a radioactive, fluorescent, biological or enzymatic label, with enzyme tags such as alkaline phosphatase, urease, horseradish peroxidase and glucose oxidase being suitable. The particular antigen employed may itself be linked to a detectable label, wherein one would then simply detect this label, thereby allowing the amount of bound antigen present in the composition to be determined.

Alternatively, the primary immune complexes may be detected by means of a second binding ligand that is linked to a detectable label and that has binding affinity for the first protein or peptide. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labelled secondary antibodies and the remaining bound label is then detected.

In related embodiments, the present invention contemplates the preparation of kits that may be employed to detect the presence of ShK-specific antibodies in a sample. Generally speaking, kits in accordance with the present invention will include a suitable protein or peptide together with an immunodetection reagent, and a means for containing the protein or peptide and reagent.

The immunodetection reagent will typically comprise a label associated with a ShK or peptide, or associated with a secondary binding ligand. Exemplary ligands might include a secondary antibody directed against the first ShK or peptide or antibody, or a biotin or avidin (or streptavidin) ligand having an associated label. Detectable labels linked to antibodies that have binding affinity for a human antibody are also contemplated, e.g., for protocols where the first reagent is a ShK peptide that is used to bind to a reactive antibody from a human sample. Of course, as noted above, a number of exemplary labels are known in the art and all such labels may be employed in connection with the present invention. The kits may contain antigen or antibody-label conjugates either in fully conjugated form, in the form of intermediates, or as separate moieties to be conjugated by the user of the kit.

The container means will generally include at least one vial, test tube, flask, bottle, syringe or other container means, into which the antigen may be placed, and preferably suitably allocated. Where a second binding ligand is provided, the kit will also generally contain a second vial or other container into which this ligand or antibody may be placed. The kits of the present invention will also typically include a means for containing the vials in close confinement for commercial sale, such as, e.g., injection or blow-molded plastic containers into which the desired vials are retained.

Polypeptide Compositions

An ShK composition of the present invention is understood to comprise one or more polypeptides that are capable of eliciting antibodies that are immunologically reactive with one or more ShK polypeptides as described in any of SEQ ID NO:2 to SEQ ID NO:61.

A ShK composition of the present invention is also understood to comprise one or more polypeptides that elicit an immune response in an animal. Likewise, an ShK composition is also understood to comprise the polypeptide of SEQ ID NO:1 substituted in one or more amino acids with one or more distinct natural or non-natural amino acids. The inventors contemplate any such modified ShK polypeptides to be useful in the practice of the disclosed methods so long as the polypeptide has Kv ion channel inhibiting activity, and in particular, selective Kv1.3 channel inhibiting activity.

As used herein, an active fragment of a ShK includes a whole or a portion of a ShK which is modified by conventional techniques, e.g, mutagenesis, or by addition, deletion, or substitution, but which active fragment exhibits substantially the same structure and function as a native ShK as described herein.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Solution Structure of ShK Toxin

Potassium channels are found in all cells, where they contribute to the regulation of membrane potential. Individual cells may express several potassium channel types, which can open in response to changes in voltage, intracellular calcium levels or specific ligands, although voltage-gated channels are the most common (Miller, 1991a; 1991b; Catterall, 1995). Potassium channel function can be modulated by a variety of toxins from the venom of bees, scorpions and snakes (Harvey, 1993). One class of channel blocker that has been studied in considerable detail is the polypeptide toxins from scorpion venom, typified by charybdotoxin. The three-dimensional structures of several have been determined (Bontems et al., 1992; Johnson and Sugg, 1992; Johnson et al., 1994; Fernandez et al., 1994; Aiyar et al., 1995; Krezel et al., 1995), their channel binding surfaces have been mapped (Aiyar et al., 1995; Park and Miller, 1992; Stampe et al., 1994; Goldstein et al., 1994), and they have been used to probe the external vestibule of the K+ pore (Stocker and Miller, 1994; Hidalgo and MacKinnon, 1995). Recently, two novel potassium channel toxins have been isolated from sea anemones, BgK, from *Bunodosoma granulifera* (Aneiros et al., 1993) and ShK, from *Stichodactyla helianthus* (Castaneda et al., 1995). Both toxins compete with dendrotoxin-I in binding to rat brain synaptosomes (Aneiros et al., 1993; Castaneda et al., 1995) but ShK toxin is also a potent blocker of the Kv1.3 potassium channel in Jurkat T-lymphocytes (Pennington et al., 1995). As the Kv1.3 channel has been implicated in T lymphocyle proliferation and lymphokine production, blockers of this channel are of interest as potential immunosuppressants (Leonard et al., 1992; Lin et al., 1993).

Although BgK and ShK toxins are identical at 13 positions (including the six half-cystines), they show little sequence similarity to other potassium channel blockers. Moreover, the half-cystines are paired in a 1–6/2–4/3–5 pattern (Pohl et al., 1995), in contrast to the 1–4/2–5/3–6 pattern of the scorpion toxins. It may be anticipated, therefore, that their three-dimensional structures are also different. The ShK toxin structure presented confirms that this is the case and provides the basis for mapping the potassium channel binding surfaces of this polypeptide, which represents a valuable new structural probe for voltage-gated potassium channels.

Two-dimensional $^1$H NMR spectra were recorded on a 5 mM solution of synthetic toxin (Pennington et al., 1995) in water at pH 4.8 and 293 K. Structural constraints were used as input to distance geometry and restrained simulated annealing calculations, following which the structures were subjected to restrained energy minimization. FIG. 1 shows that the family of structures is well defined except at the N and C termini, which showed few medium- or long-range NOE constraints. Well-defined backbone dihedral angles (S>0.8) (Hyberts et al., 1992) were found for residues 3–33. Mean pairwise r.m.s. differences calculated over the backbone heavy atoms (N, Cα, C) and all heavy atoms, respectively, of the whole molecule were 1.25±0.40 and 1.91±0.37 Å, whereas for residues 3–33 they were 0.56±0.20 and 1.25±0.19 Å. The final structures were in good agreement with the experimental restraints and had good stereochemistry (Table 2).

TABLE 2

STRUCTURAL STATISTICS FOR THE 20 STRUCTURES OF SHK TOXIN FROM X-PLOR[1]

| | |
|---|---|
| R.m.s. deviations form experimental distance restraints (Å) (344)[2] | 0.032 ± 0.001 |
| R.m.s. deviations from experimental dihedral restraints (°) (31)[2] | 0.35 ± 0.2 |

TABLE 2-continued

STRUCTURAL STATISTICS FOR THE 20 STRUCTURES OF SHK TOXIN FROM X-PLOR[1]

| | |
|---|---|
| R.m.s. deviations from idealized geometry | |
| bonds (Å) | 0.012 ± 0.0013 |
| angles (°) | 2.99 ± 0.05 |
| impropers (°) | 0.41 ± 0.03 |
| Energies (kcal mol$^{-1}$)[3] | |
| $E_{NOE}$ | 20.7 ± 1.2 |
| $E_{cdih}$ | 0.31 ± 0.25 |
| $E_{L-J}$ | −132 ± 5 |
| $E_{bond} + E_{angle} + E_{improper}$ | 150 ± 4 |
| $E_{elec}$ | −487 ± 15 |

[1]The best 20 structures after energy minimization in the distance geometry force field of X-PLOR were subsequently energy minimized in the CHARMm force field, using a distance-dependent dielectric and neutralized side chains. Values are mean ± standard deviation.
[2]The numbers of restraints are shown in parentheses.
[3]Force constants for calculation of the square-well potentials for the NOE and dihedral angle restraints were 50 kcal mol$^{-1}$ Å$^{-1}$ and 200 kcal mol$^{-1}$ rad$^{-2}$, respectively. The Lennard-Jones-van der Waals energy was calculated with the CHARMm empirical energy function. The bond, angle and improper terms serve to maintain the covalent geometry. The electrostatic contribution to the overall energy was calculated with a distance-dependent dielectric and charges neutralized (as per the templates of the GROMOS force field).

The main secondary structure elements are short α-helices encompassing residues 14–19 and 21–24 (FIG. 1C), the first of which is stabilized by a capping box involving Thr 13 and Gln 16 as well as the flanking half-cystine residues 12 and 17 (Seale et al., 1994). The N terminus adopts an extended conformation up to residue 8, where a pair of interlocking turns commences; this could be regarded as a short stretch of 3$_{10}$-helix centered on residues 9–10 (with 11→8 and 12→9 hydrogen bonds) or a pair of turns in which the first is a non-classical turn and the second is of type I (12→9 hydrogen bond). Toward the C terminus there are several chain reversals, including a type I β-turn at residues 28–31. Backbone hydrogen bonds associated with these secondary structure elements account for many of the slowly exchanging backbone amide protons observed by NMR following dissolution of ShK toxin in $^2$H$_2$O. Several other backbone amide protons found to be slowly exchanging were involved in side-chain hydrogen bonds and/or were shielded from solvent.

The 12–28 and 17–32 disulfide bonds are well defined (FIG 1B) and adopt a right-handed conformation (positive $\chi_{ss}$; the 17–32 bond is partially buried and the 12–28 bond almost fully buried in the core of the molecule. The 3–35 bond is on the surface and highly exposed, and as a consequence is not well defined in the inventors' structures.

The structure of ShK toxin bears no resemblance to those of the scorpion-derived potassium channel toxins (FIG. 2A), consistent with the lack of sequence similarity and the different disulfide pairings. Compared with charybdotoxin and agitoxin 2 the inventors' ShK toxin structure has r.m.s. differences of 6–7 Å over the backbone heavy atoms. A search of the Protein Data Bank (Bernstein et al., 1977) using the program DALI (Holm and Sander, 1993) found no similar structural folds to ShK toxin.

Despite the structural differences from the scorpion toxins, ShK toxin binds to the same site on the lymphocyte potassium channel (Pennington et al., 1995) and exerts the same effect. Given that it functions as a channel blocker, at least some of the positively charged side chains may be expected to be essential for activity (Park and Miller, 1992;

Stampe et al., 1994; Goldstein et al., 1994; Stocker and Miller, 1994; Hidalgo and MacKinnon, 1995). All of the positively charged groups are on the surface of the molecule, with Arg I and Arg II being the most exposed of the four arginines and Lys 9 and Lys 18 the most exposed lysines. The ε-ammonium group of Lys 30 is close to the carboxylate of Asp 5 (FIG. 2B), and a salt bridge between them may explain why synthetic peptide analogues with either of these residues altered do not fold readily (Pennington et al., 1996).

Lys 18 and Arg 18 of ShK are not important for binding to the Kv1.3 or Kv1.2 channels and are oriented away from the surface encompassing residues 11 and 22. The fact that Lys 22 and Arg 11 are important for binding to Kv1.3 but riot Kv1.2 suggests that it should be possible to design peptidic or peptide mimetic analogues with selectivity for the lymphocyte channel. By analogy with charybdotoxin, the inventors may expect between five and eight residues to play key roles in potassium channel binding, depending on which channel type is involved (Park and Miller, 1992; Stampe et al., 1994; Goldstein et al., 1994; Stocker and Miller, 1994). In the N-type calcium channel blocker ω-conotoxin GIVA, only two side chains were found to be critical for binding to chick brain channels (Kim et al., 1994). So far, only the cationic side chains which contribute to the binding surfaces of ShK toxin have been probed in detail. Now that the structure is available, it will be possible to design additional analogues to define the full extent of the binding surface and to undertake complementary mutagenesis on the Kv1.3 channel to define the interacting residues on the channel.

Methods

Structures were determined from 2 D $^1$H NMR spectra recorded on a Bruker AMX-600 spectrometer, usually at 293 K, although spectra were also recorded at 283 and 298 K. Methods for recording and analyzing spectra, deriving distance and angle restraints, and calculating structures in DIANA and X-PLOR were as described previously (Pallaghy et al., 1995; Monks et al., 1995). The final NMR restraint set (from which values redundant with the covalent geometry had been eliminated by DIANA) consisted of 94 intra-residue, 118 sequential, 72 medium-range (i–j$\geq$5), and 60 long-range (i–J$\geq$5) upper bound restraints, 45 lower bound restraints (Pallaghy et al., 1995), and 22 backbone and nine side-chain dihedral angle restraints. Stereospecific assignments were made for nine β-methylene pairs and for the δ-methyls of Leu 25 on the basis of the DIANA structures (in which the NOEs to the Leu 25 β-methylene and γ-methine protons constrained the side chain orientation in such a way that the δ-methyl resonances could be stereospecifically assigned). The side-chain amide protons of Gln 16 were stereospecifically assigned based on the intensities of NOESY cross peaks from the side-chain amide protons to their CγH protons. None of the structures had distance violations >0.3 Å or dihedral angle violations >3°. The final structures used for analysis were selected from the 50 CHARMm-minimized structures based on their stereochemical energies (that is, the sum of all contributions to the calculated energy except the electrostatic term) and NOE energies. Hydrogen bonds were identified using INSIGHT (version 2.3.0, Biosym Technologies, San Diego, Calif.), which was also used for visualization of structures and generation of diagrams, except as noted. These 20 structures and the NMR restraints used in their determination have been deposited with the Brookhaven Protein Data Bank (Bernstein et al., 1977).

Example 2—Methods for the Chemical Synthesis of ShK Toxin

The ShK toxin was synthesized using an Fmoc strategy and successfully folded to the biologically-active form containing three intramolecular disulfide bonds. The ability of synthetic ShK toxin to inhibit specific [$^{125}$I]-dendrotoxin I binding to rat brain membranes slightly exceeded (was more potent than) that of the natural ShK toxin sample, but was comparable with the data for native ShK toxin. The peptide toxin inhibited [$^{125}$I]-charybodotoxin binding to Jurkat T lymphocytes with an IC$_{50}$ value of 32 pM. In addition, Jurkat T lymphocytes Kv1.3 potassium channels were inhibited with an IC$_{50}$ value of 133 pM. Owing to their unique structure and high affinity for at least some potassium channels, ShK toxin and related sea anemone potassium channel toxins may be useful molecular probes for investigating potassium channels.

Certain naturally-occurring toxins from snake and scorpion venom have become useful molecular probes for investigating potassium (K) channels (Moczydlowski et al., 1988; Strong, 1990; Garcia et al., 1991). Many of these toxins are selective for particular K channel sub-types (Galvez et al., 1990; Crest et al., 1992; Garcia-Calvo et al., 1993; Garcia et al., 1994; Auguste et al., 1990). This has allowed the physiological role of specific, toxin-sensitive K channels to be investigated in cells and tissues of interest (Leonard et al., 1992).

Recently, a K channel toxin was isolated from the sea anemone *Bunodosoma granulifera* (BgK toxin) and chemically characterized (Aneiros et al., 1993) (FIG. 3). Although this toxin possesses the same number (37) of amino-acid residues as charybodotoxin (ChTX), it displays no homology to this scorpion toxin, and the positions of the half-cystines also are different. BgK toxin displaces dendrotoxin I binding to rat brain membranes with an apparent K$_i$ of 0.7 nM, and suppresses K currents in rat dorsal ganglion neurons in culture (Aneiros et al., 1993). The same scientific team recently reported the amino acid sequence for a related peptide from the sea anemone *Stichodactyla helianthus* (ShK toxin). The apparent K$_i$-value for inhibition of dendrotoxin I (DTX) binding by this toxin was similar to that of BgK toxin (Karlsson et al, 1992).

The inventors are interested in delineating the K channel interactive surface of ShK toxin. This report describes the first chemical synthesis by a solid-phase strategy and the pharmacological characterization of ShK toxin blocks Kv1.3 type K channels in Jurkat T lymphocytes at very low concentrations (<1 nM).

Experimental Procedures

Natural ShK and *Dendroaspis polylepsi* I (DTX) were provided by Dr. E. Karlsson (Biomedical Center, University of Uppsala, Uppsala, Sweden). All other reagents were the finest grade commercially available.

Synthesis of ShK Toxin

Fmoc-amino acids (Bachem Feinchemikalien, CH-4416 Bubendorf, Switzerland) included Arg(Pmc), Asp(OtBu), Cys(Trt), Gln(Trt), His(Trt), Lys(Boc), Ser(tBu) and Thr (tBu). Stepwise assembly was carried out on an Applied Biosystems 431A peptide synthesizer at the 0.25 mmol scale starting with Fmoc—Cys(Trt)—R. Residues 34–22 were single-coupled. At this point, half of the resin was removed to effect better mixing. The remainder of the peptide sequence was double coupled to the remaining resin aliquot. All couplings were mediated by dicyclohexyl-carbodiimide in the presence of 2 equiv. of 1-hydroxy-benzotriazole. Following final removal of the Fmoc-group, the peptide resin (2.42 g) was cleaved from the resin and simultaneously deprotected using reagent K (King et al., 1990) for 2 h at room temperature. Following cleavage, the peptide was filtered to remove the spent resin beads and precipitated with ice-cold diethyl ether. The peptide was collected on a fine filter funnel, washed with ice-cold ether and finally extracted with 20% AcOH in $H_2O$. The peptide extract was subsequently diluted into 2 L of $H_2O$, the pH adjusted to 8.0 with $NH_4OH$, and allowed to oxidize in air at room temperature for 36 h. Following oxidation of the disulfide bonds, the peptide solution was acidified to pH 2.5 and pumped onto a Rainin Dynamax $C_{18}$ column (5.0×30 cm). The sample was eluted with a linear gradient from 5 to 30% acetonitrile into $H_2O$ containing 0.1% TFA. The resulting fractions were analyzed using two analytical RP-HPLC systems, TFA and TEAP (Rivier and McClintock, 1983). Pure fractions were pooled and lyophilized. Upon lyophilization, 120 mg of ShK toxin was obtained, representing a yield of 24% of theory (from the starting resin).

Amino Acid Analysis

Synthetic peptide samples were hydrolyzed in 6 N HCl at 110° C. for 22 h in vacuo. Amino-acid analysis was performed on a Beckman 126AA System Gold amino-acid analyzer. The masses of the natural and synthetic ShK toxin samples used in the [$^{125}I$]DTX binding comparison were determined by Dr. Jan Pohl (Emory Microchemical Facility, Atlanta, Ga.).

FAB-MS Analysis

FAB-MS analysis was performed by M-Scan (West Chester, Pa.) on a ZAB 2-SE high-field mass spectrometer.

Ligand Binding Assay with DTX

Iodination of DTX was performed by the chloramine T method (Hunter and Greenwood, 1962). After removal of the unreacted $^{125}I$ by gel chromatography, the specific radioactivity of [$^{125}I$]DTX was 34 Ci/mmol. Male Sprague-Dawley rats (Harlan, 175–250 g) were decapitated, and whole brains were removed and homogenized at 0° C. in 10 vol. of saline (0.15 M NaCl, 0.03 M Tris HCl, pH 7.0) (wt./vol.) using a Teflon pestle. The homogenate was centrifuged (10 min, 17000×g, 4° C.), and the resulting pellet was resuspended in the saline and again homogenized. Centrifugation and homogenization were repeated once more before the membranes were used for ihe DTX binding displacement assay. Binding of ShK toxin to rat brain membranes was indirectly investigated by competition with 1 nM [$^{125}I$]DTX. Membranes (0.5 mg protein) were incubated with test compounds and [$^{125}I$]DTX in a Tris-buffered saline (0.15 M NaCi, 0.03 M Tris HCl, BSA 2 mg/ml, pH 7.0) at room temperature in a fir al volume of 0.25 ml. After 1 h incubation, membrane suspensions were diluted with two 0.7 ml portions of saline (0.15 M NaCl, 0.03 M Tris HCl, pH 7.0), and membranes with bound radioligand were separated by filtration under vacuum through glass filters (Whatman GF/C) at room temperature and washed twice with 3.5 ml of the same buffer. Filters were presoaked for 10 min in 0.5% (vol./vol.) polyethylenimine before filtration. Nonspecific binding was measured in the presence of 0.5 $\mu$M cold DTX. Membrane protein concentration was determined by the Coomassie Blue method (Bradford, 1976).

[$^{125}I$]ChTX Binding to Kv1.3 T-Lymphocyte Potassium Channels

Jurkat T lymphocytes (ATCC) were suspended in a saline solution (NaCl 5 mM, KCl 5 mM, sucrose 320 mM, HEPES 10 mM, glucose 6 mM, pH adjusted to 8.4 with Tris base). Cells (2×10$^6$/tube) were incubated in polypropylene 1 ml deep wells in the presence of 30 pM [$^{125}I$]ChTX±test agents for 20 min at 22° C. Nonspecific binding was determined in the presence of 10 nM ChTX. Binding reactions were terminated by filtration through GF/C glass filters that had been presoaked in 0.6% polyethylenimine. Samples were washed with twice with 1 ml of ice-cold wash saline (NaCl 200 mM, HEPES 20 mM, adjusted to pH 8.0 with Tris base).

Radioactivity bound to filters was measured in a Betaplate liquid scintillation to counter (Wallace Gaithersburg, Md.).

Measurement of Potassium Current in Jurkat T Lymphocytes

All recordings were made on cells bathed with saline of the following composition (in mM): NaCl 160, KCl 4.5, $MgCl_2$ 2, $CaCl_2$ 1, HEPES 10, pH 7.4. Patch pipettes (see below) were filled with (in mM): KF 154, EGTA 11, $CaCl_2$ 1.1, $MgCl_2$ 2, HEPES 10, pH 7.3 with KOH.

For electrophysiological and binding studies, cells were allowed to settle to the bottom of the chamber and adhere for approximately 5 min prior to flow being initiated. Studies were performed at room temperature (21–24° C.) with constant flow perfusion rates of 4–5 ml/min. Voltage-clamp recording utilized an Axopatch IC or 200 A amplifier (Axon Instruments, Foster City, Calif.), and data were digitized with a LabMaster 125 kHz DMA board and a Compaq Deskpro 386 computer or ALR 486 computer. All data acquisition analyses were performed with the pCLAMP software package (Axon Instruments). Current records were digitized at 2 kHz and filtered at 0.5 kHz. Series resistance compensation was employed in all studies. The membrane potential was held at −80 mV and the Kv1.3 channel current was measured by giving 150 ins voltage steps to +30 mV once every minute. Pharmacological inhibition was assessed by obtaining outward current values during the voltage step described above before and after a 6 min exposure to ShK toxin (with no applied pulses) and plotting percentage current block versus toxin concentration. A single drug concentration was tested on each cell.

Results and Discussion

Figure 4A:
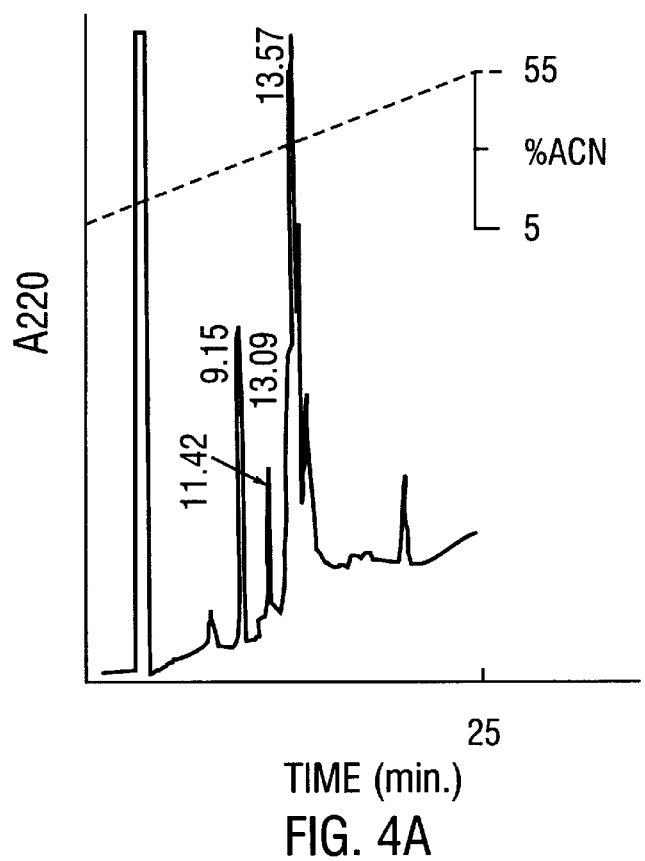
Figure 4B:
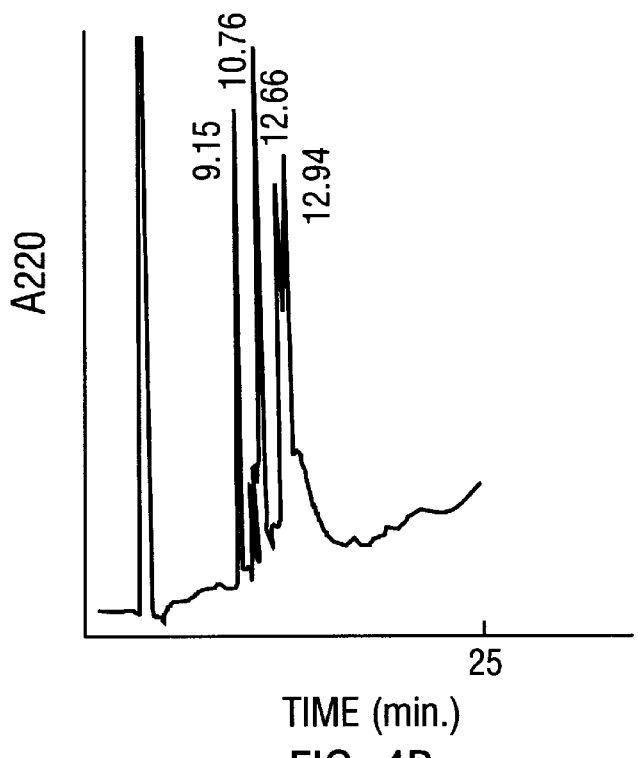
Figure 4C:
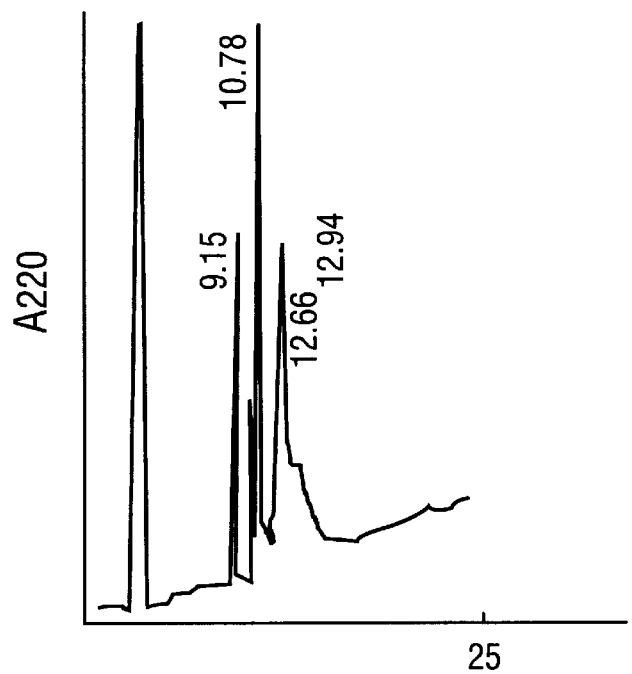

ShK toxin consists of 35 residues with a C-terminal acid (FIG. 3) (Karlsson et al., 1992). Synthesis of ShK toxin was initiated on Fmoc—Cys(Trt)—Wang resin using an automated protocol in which the first 12 residues were single coupled and the remaining 22 residues were double-coupled to maximize the coupling efficiency to insure fidelity of synthesis. The biologically active form of ShK toxin requires proper folding of three disulfide bonds. Therefore, following cleavage and deprotection, 36 h was allowed for peptide folding and disulfide bond formation under alkaline conditions in the presence of air. This oxidation time was determined to be sufficient by analysis of aliquots taken throughout an oxidation time up to 36 h. Following 36 h, there was no further change in the HPLC profile (FIG. 4).

Figure 5A:
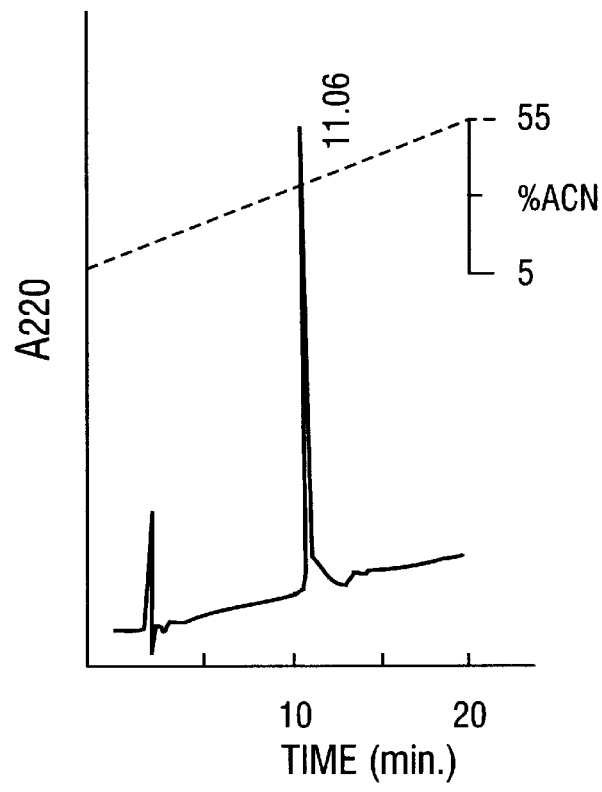
Figure 5B:
Figure 5C:
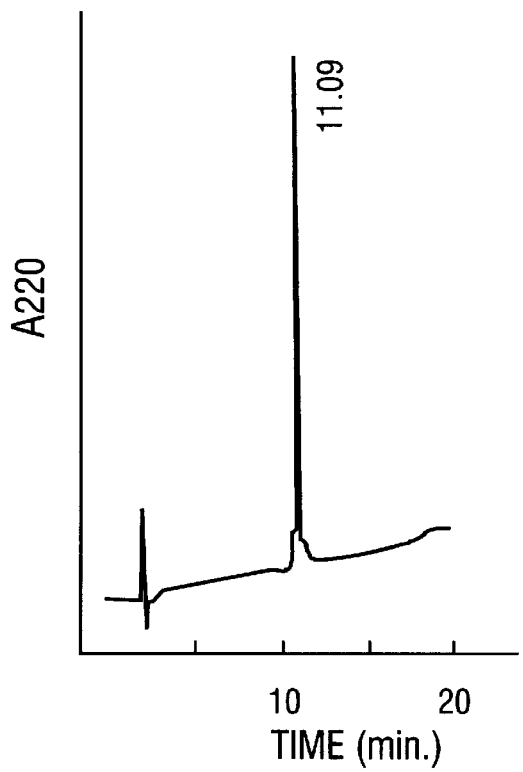

The purified synthetic product was determined to be homogeneous by analytical RP-HPLC in two different solvent systems (TFA and TEAP). The elution diagram for the TFA system is shown in FIG. 5A. Furthermore, the synthetic ShK was determined to coelute (FIG. 5C) with a sample of the natural material (FIG. 5B). Amino acid analysis of the purified ShK toxin showed the following average amino acid ralios: Asx (1) 0.99, Thr (4) 3.89, Ser (4) 4.04, Glx (1) 1.04, Pro (1) 0.89, Gly (1) 1.08, Ala (1) 1.00, Met (1) 0.88, Ile (2) 1.78, Leu (1) 1.07, Tyr (1) 0.99, Phe (2) 2.08, Lys (4) 3.94., His (1) 0.94, Arg (4) 3.85, and Cys (6) 5.46. FAB-MS analysis of the purified synthetic ShK toxin determined an (M+H) of 4055, which was consistent with the theoretical value with formation of three disulfide bonds.

In a separate report, the disulfide parings of synthetic ShK toxin were determined. It was found that $Cys^3$ was paired with $Cys^{35}$, $Cys^{12}$ with $Cys^{28}$ and $Cys^{17}$ with $Cys^{32}$ (Pohl et al., 1995).

Figure 6:
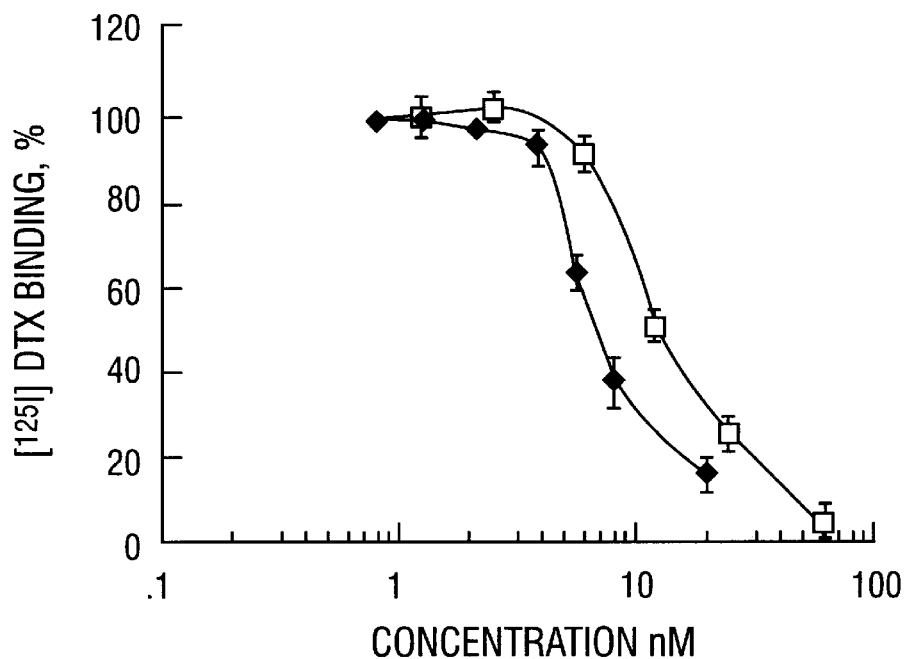

The synthetic and natural ShK toxins displaced the specific binding of DTX to rat brain membranes at concentrations which were previously reported to displace DTX binding (Karlsson et al., 1992). The reason for the lower $IC_{50}$ (more potent) of the synthetic toxin is not known (FIG. 6). However, amino acid analysis of the natural toxin sample revealed only about 40% of the expected methionine, compared to 110% for the synthetic toxin. It is possible that the observed difference in affinity for the brain K channel receptors may be due to an influence of methionine side-chain oxidation state upon binding to brain K channels.

Figure 7:
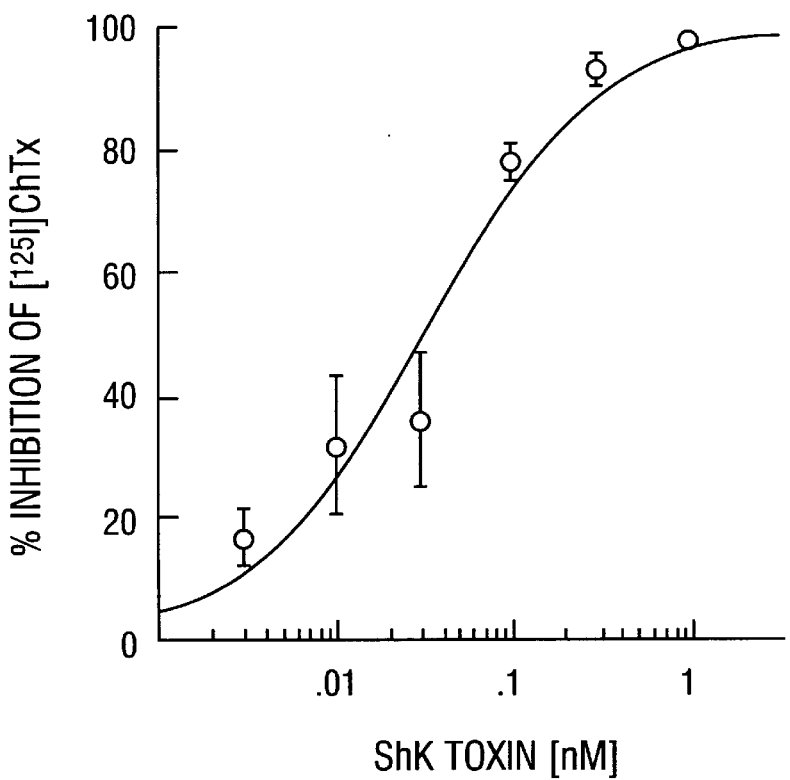
Figure 8:
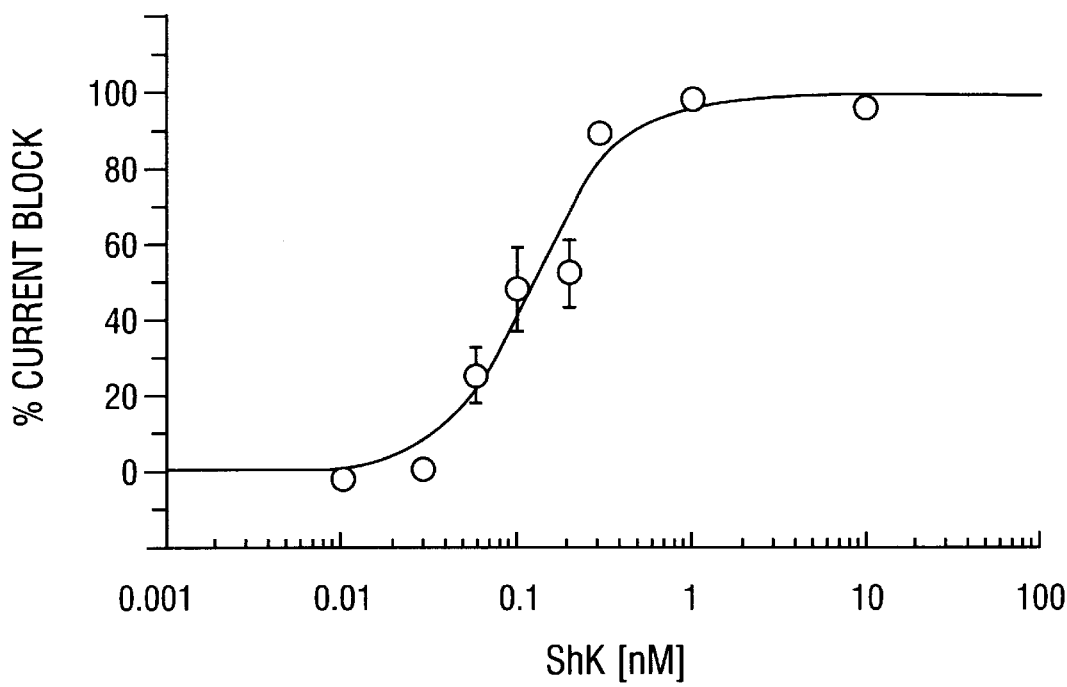

Synthetic ShK toxin inhibited [$^{125}$I]-ChTX binding to Kv1.3 channels in Jurkat T lymphocytes in a concentration-dependent manner (FIG. 7). Complete inhibition was observed at 300 pM, and the concentration response curve was well described by an $IC_{50}$-value of 32±3 pM and a Hill coefficient of 0.89±0.17 (mean±SEM,n=4).

To determine whether the ShK toxin will block potassium currents as suggested by the biochemical profile, the inventors measured Kv1.3 current amplitudes before and after exposure to the toxin (FIG. 8). ShK toxin blocks these currents in a concentration dependent manner with an $IC_{50}$ value of 133 pM and a Hill coefficient of 1.7 ShK toxin acts as a closed channel blocker, since inhibition was independent of channel opening. This profile is similar to that of ChTX, which is approximately 20 times less potent than ShK toxin.

DTX is known to bind to most voltage-gated K channels (Strong, 1990); since the ShK toxin is able to compete with all of the DTX binding sites, it can be inferred that ShK toxin also has a broad spectrum for binding to brain K channels. The present results with the Kv1.3 type K channels are the first to demonstrate that ShK toxin is able to block this particular subtype of K channel. Further studies are warranted to determine the mechanism of ShK toxin blockade of K channels.

Example 3—Assignment of the Three Disulfide Bonds in ShK Toxin

The small size of ShK toxin makes it an ideal molecule for studying structure-function relationships. The toxin contains six cysteine residues, located at positions 3, 12, 17, 28, 32 and 35, which form three intramolecular disulfide bonds (Karlsson et al., 1992). This example describes the determination of the disulfide bonding pattern of ShK toxin using Edman degradation and MALDI-TOF mass spectrometry on the RP-HPLC purified, proteolytically derived peptide fragments.

Materials and Methods

Synthetic ShK toxin was prepared as described in Example 3. Sequencing-grade and HPLC-grade solvents and reagents were obtained from Applied Biosystems (Foster City, Calif.), Achromobacter lysyl endoproteinase from Wako Bioproducts (Richmond, Va.) and thermolysin TLCK-α-chymotrypsin and TPCK-trypsin from Boehringer-Mannheim (Indianapolis, Ind.). All other reagents were of the highest grade commercially available.

Proteolytic Cleavages (1) ShK toxin (60 μg) was dissolved in 0.1 M Tris—HCI, pH 8.5, containing 2 M urea (60 μl) and was digested with lysyl endoproteinase (E:S=1:50 wt./wt., 30° C.). Aliquots (1.5 μl) of the reaction mixture were withdrawn at time intervals from 20 min to 29 h, acidified in 0.1% aqueous TFA (50 μl) and the ShK fragments were purified by RP-HPLC and characterized as described below.

(2) ShK toxin (15 μg) was dissolved in 0.05 M HEPES, pH 6.5, containing 10 mM $CaCl_2$ (30 μl) and was digested with thermolysin (E:S=1:20, wt./wt., 25° C., 3.5 h), or with a mixture of trypsin and chymotrypsin (E:S=1:1:50, wt./wt., 30° C., 6 h). The digestion was terminated by acidification with 10% aqueous TFA (3 μl), and the solution was centrifuged (13000 g, 5 min). The supernatant was directly fractionated by RP-HPLC. Selected HPLC-purified tryptic-chymotryptic peptides of ShK toxin were reconstituted in 0.05 M HEPES, pH 6.5, and 10 mM $CaCl_2$ and were subdigested with thermolysin (E:S=1:150, 25° C., 2 h) before fractionation by RP-HPLC.

RP-HPLC

The peptides were fractionated using a microbore RP-HPLC system consisting of Applied Biosystems 140 A pumps and a 1000 S diode-array detector (2.3 μl flow cell, 0.0025 inch i.d. tubing). Fractionation of the thermolytic and tryptic-chymotryptic peptides was performed on a Zorbax-SB $c_{18}$ column (1×150 mm, $d_p$~5 μm, Microtech Scientific, Saratoga, Calif.) equilibrated in 0.1% aqueous TFA, and eluted at a flow rate of 80 μl/min using a linear gradient of acetonitrile/water/TFA (80:20:0.1). The column effluent was monitored at 215 nm. The thermolytic peptides, generated by subdigestion of the tryptic-chymotryptic peptides, were reconstituted in 0.1% heptafluorobutyric acid (HFBA) and further purified on the same column, equilibrated of acetonitrile/water/HFBA (80:20:0.1). The column eluent was manually collected and stored at −20° C. until analysis.

Sequence Analysis

Automated Edman degradation of the peptides was performed on Applied Biosystems pulsed-liquid 477 A/120 A, gas phase 470 A/120 A, and 491 A/140 S Procise sequencing systems, as described previously (Pohl, 1994). Reagent 3 (TFA) and reagent 4 (25% aqueous TFA) contained 0.002% dithiothreitol. HPLC separation of the PTH amino acids was performed on-line. The solvent system for PTH separation (Pohl, 1994) was modified by replacing sodium acetate, pH ~3.95 in solvent A (3.5%, vol./vol., aqueous tetrahydrofuran) with the Premix buffer (13.5 ml/l). On all three sequencer systems, diPTH—Cys was recovered and identified as the peak coeluting with PTH—Tyr (Haniu et al., 1994; Crankshaw and Grant, 1993). PTH—Tyr coelutiol with diPTH—Cys was not problematic, since none of the disulfide-linked peptides contained tyrosine. In addition to diPTH—Cys, PTH—Ser (PTH-dehydroalanine adduct with DTT) and PTH—Ser (formed by rehydration of PTH-dehydroalanine) were also present as side products in the cycles containing cystine (see Pohl, 1994).

MALDI-TOF Mass Spectrometry

The peptides were analyzed by matrix-assisted laser desorption/ionization mass spectrometry (MALDI) using a Kratos KOMPACT MALDI III mass spectrometer (Manchester). Each fraction (0.3 μl) was spotted on a target site of a 20-sample slide, followed by addition of 0.3 μl matrix (saturated α-cyano-4-hydroxycinnamic acid; Aldrich, Milwaukee, Wis.) dissolved in 1:1 ethanol/water. The sample matrix was allowed to dry at room temperature for 5 min. Each sample was desorbed With 50 laser shots, each giving a spectrum. The shots were averaged to give the final spectrum. The instrument was calibrated using external standard peptides.

FAB Mass Spectrometry Analysis

FAB-MS analysis of synthetic ShK toxin was performed by M-can (West Chester, Pa.) on a ZAB 2-SE high-field mass spectrometer. The sample was dissolved in 5% AcOH and a matrix of m-nitrobenzyl alcohol was used. A cesium ion gun was used to generate ions for the spectra, which were recorded using a PDP 11-250J data system. Mass calibration was performed using CsI.

Results

Due to the limited amount of natural material available, the disulfide bonds of the synthetic ShK toxin were determined. The chemical identity and biological activity of the synthetic toxin were found to be identical to those of the natural material (Pennington et al., 1995).

FAB mass spectral analysis of synthetic ShK toxin determined an average mass of 4055±1. The calculated mass for ShK toxin is 4061, a difference of six mass units indicating that all six cysteine residues formed disulfide bonds. The absence of free sulfhydryls was confirmed using Ellman's reagent (Ellman, 1959). It was determined that less than 0.1% free sulfhydryls are titratable in ShK toxin dissolved in 0.1 M sodium phosphate, pH 7.6, or in the same buffer containing 4 M urea.

The six cysteine residues in the ShK toxin amino acid sequence can form three intramolecular disulfide bridges in 15 different ways. Therefore, the ShK polypeptide was cleaved into fragments using different proteases and the disulfide-linked peptides were purified and identified by sequencing and mass spectrometry.

In the initial studies, ShK was cleaved at the carboxyl side of its four lysine residues using lysyl endoproteinase. HPLC analysis of the time course of the cleavage revealed rapid formation ($\tau$<20 min) of a single predominant species. Sequence analysis of this material identified the presence of four ShK fragments, [1–9], [10–18], [23–30] and [31–35], in approximately equimolar initial sequencing yields; mass analysis identified a species of mass 3624.9. It was concluded that this is the disulfide-linked cleaved ShK that is missing the HSMK tetrapeptide [19–22] (expected mass= 3625.26). On prolonged incubation ($\tau$=2 h to 24 h, pH 8.5, 25° C.), this peptide cluster gradually disappeared from the chromatograms and was replaced by multiple peptides which were mostly less retained on the reversed-phase column. These fragments were later identified as being either pure [1–9], [10–18], [23–30] and [31–35], or their disulfide-linked combinations. Therefore, it could be concluded that, at an alkaline pH of 8.5, extensive disulfide interchange occurred (see, e.g. Schrohenloher and Bennett, 1994); lysyl endoproteinase was not used in subsequent studies.

In order to minimize disulfide rearrangement, the following studies were conducted at pH <7. ShK toxin was completely resistant to proteolysis (3.5 h, 30° C.) by porcine pepsin A (E:S=1:300, pH 3.0), pancreatic elastase (E:S= 1:20, pH 6.5) and subtilisin (E:S=1:20, pH 6.5) as determined by HPLC and sequence (pepsin A digest) analysis. However the toxin was readily cleaved at pH 6.5 with a mixture of trypsin-chymotrypsin (FIG. 9), or with thermolysin alone. The $Cys^{12}$–$Cys^{28}$ disulfide was identified through isolation of CTAF—CR(K) [12–15]/[28–29(30)] from the combined tryptic-chymotryptic digest (FIG. 9) (peaks at 23.29 and 28.12 min). For unknown reasons, peptide fragments with the same sequence were observed with different retention times by RP-HPLC. This phenomenon has been observed in many different protease digest studies with other proteins (Table 2). In addition, the disulfide cluster [1–9]/[16–18]/[30–35] and its truncated versions were also purified and identified by sequencing. In the combined tryptic-chymotryptic digest, the ShK sequence was identified with the exception of the polar tryptic dipeptide [10–11], Ser—Arg, which likely eluted early in the gradient. In order to identify the remaining two disulfides, the [1–9]/[16–18]/[30–35] cluster was subdigested with thermolysin and the peptides were purified (FIG. 10). Owing to the facile cleavage of the ~$Gly^{33}$–$Thr^{34}$~ peptide bond by thermolysin, the closely spaced $Cys^{32}$ and $Cys^{35}$ residues were separated, and the $Cys^{17}$–$Cys^{32}$ disulfide could be identified in seven pure peptides (FIG. 10, Table 3). Sequencing of the material eluting between 7 and 9 min indicated the presence of disulfide-linked peptide(s); however, the inventors failed to obtain any mass information on this mixture. In a subsequent study, substantially stronger retention of these peptides was induced, and their complete resolution was in turn accomplished by chromatography of the mixture in solvents containing HFBA as the counterion (FIG. 11, Table 3). The third disulfide, $Cys^3$–$Cys^{35}$, could be identified and unambiguously assigned.

TABLE 3

IDENTIFICATION OF PEAKS GENERATED BY CHYMOTRYPTIC-TRYPTIC AND THERMOLYTIC DIGESTION OF SYNTHETIC SHK TOXIN

| Disulfide Bridge | ShK Position | Sequence Found by Edman Degradation | MH+ Observed[a] | MH+ MW |
|---|---|---|---|---|
| $C^1$–$C^6$ | ($C^3$–$C^{35}$) | RSC | 585.2 | 584.69 |
| | | TC | | |
| $C^2$–$C^4$ | ($C^{12}$–$C^{28}$) | IDTIPKSRC | 1585 | 1582.93[b] |
| | | FCRK | | |
| | | CTAF | 715.9 | 715.87 |
| | | CR | | |
| $C^3$–$C^5$ | ($C^{17}$–$C^{32}$) | KTC | 727.0 | 725.90 |
| | | QCK | | |
| | | FQCKH | 944.0 | 939.11[b] |
| | | TCG | | |
| | | KTCG | 783.7 | 782.95 |
| | | QCK | | |
| | | TCG | 652.2 | 654.80 |
| | | QCK | | |
| $C^3$–$C^1$ | $\{\frac{C^{17}-C^3}{C^{32}-C^{35}}\}$ | QCKH RSC | 1360.9 | 1358.52[b] |
| | | TCGTC | | |

[a]MN+ = protonated molecular ion = (mass/charge) + H+. In all sequences the charge was one.
[b]Peptide derived from thermolysin digest of ShK toxin.

In a separate study, ShK toxin was cleaved with thermolysin alone at pH 6.5, and the peptides were separated and identified (Table 3). The $Cys^{12}$–$Cys^{28}$ and $Cys^{17}$–$Cys^{32}$ disulfides were identified as pure entities. The $Cys^3$–$Cys^{35}$ disulfide-linked peptide [1–3]/[34–35] was identified by sequencing.

Discussion and Conclusions

FIG. 12 shows the arrangement of disulfide bonds in ShK toxin. This is the first sea anemone potassium channel toxin in which the disulfide bonds have been assigned. A common structural element found in peptide toxins and protease inhibitors is a disulfide pairing arrangement which creates a knotted-type structure. In many cases, molecules with totally different biological properties have the same disulfide pairing array and tertiary structural elements (Pallaghy et al., 1994). In fact, some toxins, such as α-dendrotoxin, have nearly identical crystal structures as some protease inhibitors, such as bovine pancreatic trypsin inhibitor (Skarzynski, 1992). The disulfide bonds are essential in creating this type of structural identity. The knotted arrangement creates a very compact structure, orienting the disulfide bonds to the internal hydrophobic domain of the folded molecule. The disulfide pairings of ShK toxin do not fit into the cystine knot triple-strand β-sheet structural motif described by Pallaghy et al., (1994). The arrangement present in ShK still appears to create a 'knotted' type of configuration about the $Cys^{12}$–$Cys^{28}$ and $Cys^{17}$–$Cys^{32}$ pairings. Additionally, the other disulfide bond creates one large loop ($Cys^3$ to $Cys^{35}$), giving ShK toxin a cyclic structure as well.

Interestingly, if the cysteine residues are numbered consecutively relative to their occurrence in the peptide sequence, the same disulfide bonding pattern of $C^1$–$C^6$, $C^2$–$C^4$ and $C^3$–$C^5$ found in ShK toxin is present in the dendrotoxins, peptide potassium channel blockers derived from snake venom (Harvey and Anderson, 1991), as well as in the antibiotic peptide defensins (Selsted and Harwig, 1989). It will be interesting to compare the solution structures of these molecules to observe whether any common structural motif arises for this pairing arrangement.

Example 4—Identification of 3 Separate Binding Sites on ShK Toxin

Eighteen synthetic analogs of ShK toxin were prepared in order to identify functionally important residues. CD spectra of sixteen of the analogs were virtually identical with the spectrum of wild-type toxin, indicating that the conformations were not affected by the substitutions. A conserved residue, Lys22, is essential or ShK binding to rat brain K channels which are primarily of the Kv1.2 type. However, a cationic side chain at position 22 is not essential for binding to the human Jurkat T-lymphocyte K channels. In contrast to the rat brain channels, ShK binding to Kv1.3 was sensitive to substitution at Lys9 and Arg11.

Using a solid-phase synthetic approach, the inventors have begun to map the K channel interactive surface of ShK toxin which is essential for K channel binding. This example describes the synthesis of a variety of monosubstituted ShK toxin analogs at eleven of the non-cysteine positions and evaluation of substitution effects with rat brain membranes enriched in Kv1.2 channels and Jurkat T-lymphocytes containing Kv1.3 channels.

EXPERIMENTAL PROCEDURES

Natural Toxins

Dendrotoxin I (DTX) isolated from *Dendroaspis polylepis* was obtained from by Dr. E. Karlsson, Biomedical Center, University of Uppsala, Sweden. Wild-type ShK toxin and radioiodinated dendrotoxin I (DTX) were prepared according to previously described methods (Pennington et al., 1995). All other reagents were the finest grade commercially available.

Synthesis of ShK Toxin Analogs

Fmoc-amino acids (Bachem Feinchemikalien, Bubendorf, Swilzerland) included: Ala, Arg(Pmc), Asn(Trt), Asp(OtBu), Cys(Trt), Gln(Trt), Gly, His(Trt), Homocitrulline, Ile, Leu, Lys(Boc), Met, Nle, Orn(Boc), Phe, p-aminoPhe(Boc), ρ-nitroPhe, Pro, Ser(tBu), Thr(tBu), and Trp. Stepwise assembly was carried out starting with 10 g of Fmoc—Cys(Trt)-resin (0.65 mmol/g) on a Labortec SP640 peptide synthesizer through 10 synthetic cycles (residues 34 through 25). At this point, resin aliquots were removed and placed on an Applied Biosystems 431 A peptide synthesizer at the 0.25 mmol scale and the remaining amino acid sequence incorporating the substitution was assembled as described above. K30A analog was synthesized entirely on an ABI 431 A according to the procedure used to prepare wild-type ShK toxin described above except for the substitution of Ala for Lys30. Following final removal of the Fmoc-group, each of the peptides was cleaved from the resin and simultaneously deprotected using reagent K (King et al., 1990) for 2 h at room temperature. After cleavage, the peptide was filtered to remove the spent resin beads and precipitated with ice cold diethyl ether. The peptide was collected on a fine filter funnel, washed with ice cold ether and finally extracted with 20% AcOH in $H_2O$. Oxidative folding of the disulfide bonds and subsequent purification were as previously described in Example 3. Pure fractions were pooled and lyophilized. Structures and the purity of all the analogs were confirmed by HPLC, circular dichroism spectroscopy, amino acid and FAB-MS analysis.

Binding Assays and Electrophysiological Characterization

The procedures for measuring displacement of $^{125}$I-DTX to rat brain membranes and for blockade of voltage-activated Kv1.3 channels in Jurkat T lymphocytes were described previously (Pennington et al., 1995).

Results and Discussion

Air oxidation of the crude, linear precursors of most of the ShK toxin analogs afforded peptides having proper disulfide pairings as the major products, which were purified by preparative RP-HPLC. Most of the analogs were obtained in very good yields (12–25% from starting resin). Wild-type ShK toxin has a characteristic CD spectrum indicative of a peptide containing about 30% α helix. CD spectra for 16 of the 18 analogs were almost identical to that of the native toxin, possessing similar mean residue ellipticity amplitudes and 208 ellipticity: 222 ellipticity ratios of about 1.05–1.10.

Oxidative folding of Asp5 to Asn (D5N) and the Lys30 to Ala (K30A) failed to yield a major product after 36 to 72 h. A normal folding study for ShK toxin results in a major product (10.76 min peak; usually 40% of total peak integrated area). Incorrectly folded and polymeric species (12.74 min region) usually elute as a heterogeneous broad peak by HPLC. The profiles obtained from HPLC analysis of an aliquot taken from each of the crude products after 72 h of oxidative folding are shown in FIG. 14B (for ShK D5N) and FIG. 14C for ShK K30A. A profile of this type obtained after folding a synthetic peptide with multiple disulfide bonds indicates the presence of multiple peptide conformers. As ShK contains three disulfide bonds, fifteen monomeric isomers are possible. Resolution of these conformers was extremely difficult and therefore not pursued.

To investigate the type of block induced by ShK peptides, an experimental protocol was used where the Jurkat cell was initially exposed to toxin for 6 minutes without stimulation (e.g., holding potential of −80 mV). Using this protocol, the K channels remain in a resting, non-conducting configuration and if blockade by toxin occurs one can assume that it is interacting with a closed state of the channel. Agents which block open channels (Hill et al., 1995) would not cause significant changes in peak current in the second test pulse, but would accelerate the rate of inactivation during the pulse. Current amplitudes during subsequent test pulses would also be significantly reduced. FIG. 15 shows that ShK toxin behaved like a closed channel blocker. Block occurred in the absence of activation (compare A and B) and there was little change in the inactivation kinetics. A subsequent test pulse did not produce substantially more block (compare C to B), which also supports a lack of specific toxin interaction with open channels. All analogs of ShK which were examined block Kv1.3 currents in a similar manner, regardless of potency.

The binding of ShK and its analogs to rat brain membrane Kv1.2 channels (Scottetal., 1994) was measured by inhibition of $^{125}$I-DTX. The analog to wild-type $IC_{50}$ ratios determined for all the correctly-folded synthetic analogs are listed in the second column of Table 4. The replacement of Lys22 with hydrophobic (Ala and Nle), hydrophilic (homocitrulline) and basic (Arg) side chains resulted in the largest reductions in channel affinity, with respective increases in $IC_{50}$ ratio of >250, >500 and >500 times. While substitution of Lys22 with Orn (K22Orn) had little effect, substitution with the bulky guanidinium group (Arg) reduced potency >500-fold. The Arg sidechain is nearly ~1 Å longer than that of Lys. Additionally, it imparts a bulky planar configuration to the positive charge which occupies a space of ~4.2 Å compared with the pyramidal configuration in the primary amine group which occupies a space of only ~1.7 Å (Aiyar et al., 1995).

TABLE 4

AFFINITY OF SHK TOXIN ANALOGS TO BLOCK JURKAT LYMPHOCYTE Kv1.3 POTASSIUM CHANNELS AND DISPLACE $^{125}$I-DENDROTOXIN BINDING TO RAT BRAIN MEMBRANES

| Toxin analog | Equipotent Molar Ration (Analog $IC_{50}$/ShK $IC_{50}$) | | SEQ ID NO: |
|---|---|---|---|
| | Lymphocyte | Rat brain | |
| ShK | 1.0 | 1.0 | 1 |
| R1S | 0.92 | 1.5 | 13 |
| K9Q | 9.6 | 0.6 | 14 |
| R11Q | 42 | 1.8 | 15 |
| F15A | 0.85 | 0.6 | 16 |
| F15W | 0.80 | 1.0 | 17 |
| K18A | 0.48 | 0.8 | 18 |
| M21Nle | 0.80 | 0.8 | 19 |
| K22A | 2.3 | >250 | 20 |
| K22Nle | >23 | >250 | 21 |
| K22Orn | 1.2 | 1.7 | 22 |
| K22Homocit | — | >500 | 23 |
| K22R | 225 | >500 | 24 |
| Y23F | 1.3 | 0.8 | 25 |
| Y23Nph* | — | 1.0 | 26 |
| Y23Apa | — | 0.8 | 27 |
| R24A | 2.4 | 1.3 | 28 |

Nph, p-nitrophenylalanine; Apa, p-aminophenylalanine.

Electrophysiological assessment of Kv1.3 was carried out with Jurkat T lymphocytes, using a patch clamp assay (Table 4, column 1). It is apparent that Arg11 is an important residue. The R11Q analog affinity was 42-fold less than for ShK toxin. However, Arg 11 does not appear to be critical for binding to rat brain membrane K channels. Another structural difference between the lymphocyte and rat brain K channel responses, was observed with analog K22A. K22 does not appear to be essential for effective Kv1.3 blockade, as the $IC_{50}$'s for K22A and K22Orn were only slightly reduced (two times) relative to the wild-type toxin. However, analogs K22Nle (containing a significantly larger hydrophobic residue) and K22R (containing a larger, bulkier cationic group) reduced the affinity more than 23- and 225-fold, respectively. Since K9Q displayed an $IC_{50}$ 9.6 times less than that of wild-type ShK, Lys9 seems important for Kv1.3 channel blockade.

The functional importance of ShK toxin Lys22 resembles that of Lys27 in the ChTX (Park et al., 1992). In kaliotoxin (a ChTX homolog), Lys27 is oriented into the lumen of the K channel pore and interacts with Asp4022 in the Kv1.3 channel model (Aiyar et al., 1995; Guy et al., 1994). For kaliotoxin analogs, Aiyar et al., (1995) have shown that both substituent size (bulk) and distance are critical for effective binding to the Kv1.3 channel. Replacement of Lys27 in kaliotoxin with Arg or p-amino-Phe reduced potency by >100-fold, whereas replacement with Orn did not alter peptide block. The results for ShK toxin Lys22 replacements are consistent with the scorpion toxin data.

Substitutions at positions ArgI (R1S), Phe15 (F15A, F15W), Lys18 (K18A), Met21 (M21N1e), Tyr23 (Y23Nph, Y23F, Y23Apa) and Arg24 (R24A) caused no significant affect on binding to either K channel subtype. Each of the $IC_{50}$ ratios for these analogs differed by no more than two-fold from the wild-type toxin (Table 4).

Synthetic analogs D5N and K30A failed to fold to a unique major product. In both cases, the inventors observed HPLC profiles characteristic of multiple (probably disulfide) conformers. These two residues are absolutely conserved in the three anemone toxins whose sequences which have been determined (FIG. 13). Also, Asp5 is the only anionic residue in the entire molecule besides the C-terminal Cys carboxyl group. In similar analog studies on ω-conotoxin GVIA, disruption of a critical hydrogen bond resulted in the failure of the peptide to fold to a unique major product. The NMR solution structure of this ω-conotoxin analog suggests that the analog failed to fold because a critical hydrogen bond had been eliminated. In ShK toxin, the disulfide pairings place the N- and C-termini in close proximity. The inventors propose that the analogs containing either Asp5 or Lys30 replacements are unable to form a salt bridge between the two ionized side chains which is required for proper folding of the toxin. The solution structure provides further evidence for the existence of a salt bridge between Asp5 and Lys30.

The NMR-derived structure of ShK places Lys22 within a small stretch of α-helix. This contrasts with the ChTX homologs, where the essential Lys27 residue occurs within a small stretch of β-sheet (Aiyar et al., 1995; Bontems et al., 1992). The inventors have recently shown that ShK and ChTX bind competitively to brain K-channels. The location of ShK toxin Lys22 within a helical structure represents a unique difference between the interactive surfaces of the sea anemone and scorpion toxins. Furthermore, the different effects on the two Kv subtypes by the ShK toxin analogs containing substitution at positions 9, 11 and 22 indicates that ShK toxin will become a useful model for designing selective inhibitors of delayed rectifier type K channels which may be of therapeutic interest.

Additional binding data from ShK and other analogs is provided in Tables 4 through 10 (Table 4, Table 5, Table 6, Table 7, Table 8, Table 9 and Table 10).

TABLE 5

"ALA SCAN" OF SHK TOXIN

| AA Residue | $IC_{50}$ Ratio | Difference of Free Energy of Binding (kcal/mol)[1] | SEQ ID NO: |
|---|---|---|---|
| R1A | 1.5 | 0.23 | 29 |
| S2A | 0.5 | −0.41 | 30 |
| I4A | 0.7 | −0.20 | 31 |
| D5A | N.D.[2] | N.D.[2] | 32 |
| T6A | 0.8 | −0.13 | 33 |
| I7A | 5.2 | 0.96 | 34 |
| P8A | 1.9 | 0.38 | 35 |
| K9A | 1.3 | 0.15 | 36 |
| S10A | 1.6 | −0.30 | 37 |

TABLE 5-continued

"ALA SCAN" OF SHK TOXIN

| AA Residue | IC$_{50}$ Ratio | Difference of Free Energy of Binding (kcal/mol)[1] | SEQ ID NO: |
|---|---|---|---|
| R11A | 2.0 | 0.41 | 38 |
| T13A | 1.7 | 0.31 | 39 |
| F15A | 0.6 | −0.30 | 40 |
| Q16A | 1.0 | 0.0 | 41 |
| K18A | 0.8 | −0.13 | 42 |
| H19A | N.D.[2] | N.D.[2] | 43 |
| S20A | 5.9 | 1.04 | 44 |
| M21A | 0.6 | −0.30 | 45 |
| K22A | >250 | >3.23 | 46 |
| Y23A | 108 | 2.74 | 47 |
| R24A | 2.4 | 0.51 | 48 |
| L25A | 1.4 | 0.20 | 49 |
| S26A | 1.9 | −0.06 | 50 |
| F27A | 15.3 | 1.59 | 51 |
| R29A | 0.8 | −0.13 | 52 |
| K30A | 5.3 | 0.98 | 53 |
| T31A | 0.6 | −0.30 | 54 |
| T34A | 1.0 | 0.0 | 55 |

[1]Difference of Free Energy of Binding calculated from ΔG = RT ln (IC$_{50}$ Analog/IC$_{50}$ WT Toxin)
[2]N.D. is not determined due to failure to fold. Highlighted residues constitute binding surface.

From the data presented in Table 6, the binding surface of ShK centers around a cluster of residues from Ser20 to Lys30. A CPK diagram of ShK toxin, shown in FIG. 19, illustrates the relative position of the side chains which constitute the ShK binding surface. Most of these residues are clustered together in the solution structure. The two critical residues Lys22 and Tyr23 reside within a small α-helical segment in the peptide. Lys22 in ShK toxin functions similarly to the critical Lys27 in charybdotoxin.

TABLE 6

POSITION 22: SAR ON BRAIN DELAYED RECTIFIER K CHANNELS, PRIMARILY Kv1.2

| Substitution | IC$_{50}$ Ratio | ΔF (kcal/mol) | SEQ ID NO: |
|---|---|---|---|
| WT-(Lys22) | 1.0 | 0.0 | 1 |
| Orn | 1.2 | 0.11 | 22 |
| Arg | >500 | >3.65 | 24 |
| Homocit | >500 | >3.65 | 23 |
| Ala | >250 | >3.23 | 20 |
| Nle | >250 | >3.23 | 21 |
| Glu | 726 | 3.86 | 7 |
| DAP | 44.2 | 2.23 | 63 |

TABLE 7

POSITION 23: SAR ON BRAIN DELAYED RECTIFIER K CHANNELS

| Substitution | IC$_{50}$ Ratio | ΔF (kcal/mol) | SEQ ID NO: |
|---|---|---|---|
| WT-(Tyr) | 1.0 | 0.0 | 1 |
| Ala | 108.0 | 2.74 | 47 |
| Phe | 1.1 | 0.09 | 25 |
| Cha | 8.8 | 1.27 | 8 |
| Bpa (p-Benzoyl-Phe) | 3.76 | 0.78 | 57 |
| Nph (p-Nitro-Phe) | 1.0 | 0.0 | 26 |
| Apa (p-Amino-Phe) | 0.8 | −0.13 | 27 |

TABLE 8

POSITION 11: SAR ON BRAIN DELAYED RECTIFIER K CHANNELS

| Substitution | IC$_{50}$ Ratio | ΔF (kcal/mol) | SEQ ID NO: |
|---|---|---|---|
| WT-(Arg) | 1.0 | 0.0 | 1 |
| Ala | 2.0 | 0.41 | 8 |
| Gln | 0.8 | −0.13 | 15 |
| Glu | 30.8 | 2.01 | 4 |

TABLE 9

POSITIONAL SAR ON BRAIN DELAYED RECTIFIER K CHANNELS

| Substitution | IC$_{50}$ Ratio | ΔF (kcal/mol) | SEQ ID NO: |
|---|---|---|---|
| N$^\alpha$-AC | 1.0 | 0.0 | 2 |
| des-R$_1$-S$_2$ | 2.54 | 0.54 | 3 |
| F15A | 0.85 | −0.09 | 16 |
| F15W | 0.80 | −0.13 | 17 |
| F15p-azido-Phe | 1.4 | 0.2 | 59 |
| H19K | 2.6 | 0.56 | 6 |
| F27Cha | 0.7 | −0.21 | 9 |

TABLE 10

Kv1.3-SHK DOCKING MODEL: MULTI-ALA SUBSTITUTIONAL VERIFICATION

| Substitution | IC$_{50}$ Ratio | ΔF (kcal/mol) | SEQ ID NO: |
|---|---|---|---|
| WT-(I4,F15,L25) | 1.0 | 0.0 | 1 |
| A4 + A15 | 0.5 | −0.41 | 10 |
| A15 + A25 | 2.1 | 0.43 | 11 |
| A4 + A15 + A25 | 0.2 | −0.94 | 12 |

TABLE 11

DISPLACEMENT OF $^{125}$I-DTX WITH NEW SHK ANALOGS

| Analog Code | Analog Type | Analog IC$_{50}$/ShK IC$_{50}$ |
|---|---|---|
| 101 | Triple mutant Nle21, Dat22, A23 | >280 |
| 102 | R$_{24}$E | 2.65 |
| 103 | K$_{18}$E | 4.64 |
| 104 | K$_9$E | 3.57 |
| 105 | Dicyclic(C$_{12}$–C$_{28}$/C$_{17}$–C$_{32}$) | 417.0 |
| 106 | Lactam Bridge (K$_{14}$–D$_{18}$) | 1.63 |
| 107 | Biotin (photoaffin, label) | 29.43 |

Example 5—Analysis of ShK Toxin Analogs

Experimental Procedures

Natural Toxins

Natural toxins were isolated and prepared as described in Section 5.4.1.1.

Synthesis of ShK Toxin Analogs

Sythesis of ShK toxin analogs was performed as described in 5.4.1.2.

Binding Assays

The procedures for measuring displacement of $^{125}$I-DTX binding to rat brain membranes were previously described (Pennington et al., 1995). In brief, ShK toxin and its analogs were incubated with rat brain membranes (0.2 mg of protein) and 1 nM [$^{125}$I]-DTX (60 Ci/mmol) for 1 hr at room temperature. The incubation was carried out in a buffer containing 150 mM NaCl, 30 mM Tris—HCl and 1 mg/ml BSA, pH 7.0, in a total volume of 0.25 ml. Nonspecific binding was measured with 1 μM cold DTX. The measurements were performed in triplicate. The standard error of mean measurement was less than 6%.

Results and Discussion

Air oxidation of the linear precursors afforded peptides having proper disulfide pairings as the major product. In the case of K30A, the analog required the addition of glutathione to afford a major product (FIG. 16A and FIG. 16B). This residue was shown to be critical for normal toxin folding. The solution structure of the toxin places the ε-amino group of Lys30 in close proximity to the Asp5 carboxyl. Tudor and Norton have found that certain Lys30 and Asp5 protons titrate together, which is ilso consistent with Lys30 being involved in an ionic interaction which may affect toxin folding. Attempts at folding Asp5 analogs D5A and D5E (FIG. 16C and FIG. 16D) also failed. The failure of D5E to fold properly suggests that the distance separating the two ionizable groups is also quite critical.

The inventors' "Ala scan" data also implicates His19 as important for folding. Repeated folding attempts with H19A, including addition of glutathione, failed to yield a major product (FIG. 16E). However, a correctly folded H19K analog was isolated by HPLC (FIG. 16F). The His residue occurs at the end of the first helical segment in ShK toxin; a polar/basic residue at position 19 may be essential for ShK folding, perhaps by stabilizing the helical dipole.

The single Pro residue occurring at position 8 in ShK toxin resides between an extended peptide bond conformation and a possible $3_{10}$ helix. Alanine substitution at this position did not affect folding (as studied by HPLC and CD analysis) and only slightly affected K channel binding. The other homologous sea anemone potassium channel toxins lack Pro.

The CD spectra of all the folded analogs were virtually identical to that of ShK toxin, providing evidence that the conformation of each analog was similar to that of native ShK. Wild-type ShK toxin has a characteristic CD spectrum indicative of a protein containing approximately 30% α-helix.

The binding affinities of ShK toxin and its analogs for rat brain K channels, which are predominantly Kv1.2 channels, were determined by inhibition of specific $^{125}$I-dendrotoxin binding to rat brain membranes. Differences between the free energies of binding of the "Ala scan" analogs relative to ShK toxin are plotted in FIG. 17. (A positive ΔF value means toxin affinity was less than that of the wild-type toxin sequence.) Replacement of Tyr23 with Ala (Y23A) resulted in the largest reduction of affinity (FIG. 18), and more than a 2.8 kcal/mol increase in the relative free enerrgy of binding (FIG. 17). Replacement of Phe27 with Ala also lowered the affinity by nearly 1.6 kcal/mol. Three monosubstituted analogs, I7A, S20A and K30A, displayed :moderately reduced affinity amounting to an increase of approximately 1 kcal/mol. Most other substitutions resulted in free energy differences which were very small (<0.5 kcal/mol), indicating binding similar to the wild type toxin.

Several analogs actually showed increased binding affinity relative to wild-type ShK toxin. As shown in FIG. 17, F15A, K18A, M21A, S26A, R29A and T31A displayed increased affinities, reflected in a negative value for the relative free energy of binding values. Reducing steric bulk at these sites allows easier access of the toxin to the K channel vestibule.

Additional monosubstituted analogs were prepared to evaluate the inventors' hypothesis that Lys22 is crucial for rat brain Kv1.2 binding. The inventors speculated that Lys22 might interact with an anionic residue, like Asp402 in the Kv1.3 model (Guy and Durell, 1994; Aiyar et al., 1995). Replacement of its basic side chain with an anionic side chain was expected to inhibit insertion of this portion of the toxin into the lumen of the K channel pore. As shown in Table 12 and FIG. 18, K22E displayed a greatly reduced affinity for the rat brain K channel. The R11E analog also displayed a 30-fold decrease in affinity, which implicates this side chain as part of the Kv1.2 pharmacophore. Data indicate that the Lys22 side chain is the most critical basic residue in the toxin for interaction with rat brain Kv1.2 channels.

TABLE 12

AFFINITY OF SHK TOXIN ANALOGS FOR DISPLACING $^{125}$I-DENDROTOXIN FROM RAT BRAIN MEMBRANES

| Toxin Analog | Equipotent Molar Ratio (Analog IC$_{50}$/ShK IC$_{50}$) | Free Energy Differ. of Binding ΔF (kcal/mol) | SEQ ID NO: |
|---|---|---|---|
| N$^\alpha$Ac | 1.0 | 0.0 | 2 |
| desR1-S2[1] | 2.5 | 0.54 | 3 |
| R11E | 30.8 | 2.01 | 4 |
| Q16E | 2.8 | 0.60 | 5 |
| H19K | 2.6 | 0.56 | 6 |
| K22E | 726.0 | 3.86 | 7 |
| Y23Cha | 8.8 | 1.27 | 8 |
| F27Cha | 0.7 | −0.21 | 9 |
| A4 + A15[2] | 0.5 | −0.41 | 10 |
| A15 + !25[2] | 2.1 | 0.43 | 11 |
| A4 + A15 + A25[2] | 0.2 | −0.94 | 12 |

[1]Analog where N-terminal Arg and Ser were deleted.
[2]Multiply substituted analog where each relative substitution site is referred to by number in the ShK sequence.

The importance of the final two basic groups in ShK, the α-amino group and the His19 imidazole ring were respectively tested by preparing the N$^\alpha$—Ac: derivative and the H19K analog. The inventors also prepared the truncated desR1–S2 peptide in an attempt to shrink the size of the molecule in a manner similar to a recent report on atrial natriuretic factor (Li et al., 1995). As shown in Table 12, neither acetylation nor truncation of the amino terminus significantly affected ShK toxin binding. The H19K analog displayed a slightly reduced IC$_{50}$ ratio, which supports the inventors' hypothesis of a structural role for this residue.

The potential importance of the planar aromatic side chains at position 23 and 27 was also assessed with several analog 7 ShK toxin. Saturation of the aromatic ring results in a nonplanar hydrophobic cyclohexylalanine (Cha) side chain. Substitution of Cha for Tyr23 (Y23Cha) resulted in more than an eight fold reduction in potency (Table 12 and FIG. 18). For future photoaffinity labeling studies, Y23Bpa (ρ-benzoyl-Phe) was prepared. Increasing the bulkiness of the side chain in Y23Bpa only slightly decreased the binding affinity. Thus, analogs at position 23 show that a planar aromatic side chain is important. In contrast, replacement of Phe27 with Cha slightly increased toxin affinity; the inventors conclude that hydrophobicity is important here, but a planar aromatic side chain is not necessary.

Lastly, Table 12 lists several additional analogs in which 2–3 hydrophobic residues were simultaneously substituted with Ala. A model which docks the ShK toxin into a model of the lumen of the Kv1.3 channel, reducing the bulk of these side chains should decrease the dimensions of the channel-binding surface of the toxin and thereby facilitate insertion of the toxin into the channel vestibule. As shown in Table 11, each of the multiply substituted analogs, A4+A15+A25 and A4+A15, are more potent than the wild-type toxin. This data suggests orienting the Lys22 amino group into the K channel pore lumen.

The data provides strong evidence that the Tyr23 residue present in all three sea anemone K channel toxins isolated to date is an important residue for binding to at least one of the Shaker type K channels. The phenolic hydroxyl was not essential, as Y23F binding affinity was essentially identical with that of the wild-type toxin. Nevertheless, an aromatic moiety is clearly important at this position, since the Y23A and Y23Cha analogs respectively displayed >100-fold and >8-fold lower affinities for rat brain channels relative to ShK toxin (FIG. 18).

The binding surface of ShK toxin appears to involve the side chains of at least six amino acid residues. Most of these residues are located in the region from 20–30 of the toxin sequence. As shown in FIG. 19, most of these residues are clustered together on the surface of the solution structure of ShK toxin. The two critical residues (Lys22 and Tyr23) are proximal to each other with the lysine side chain most exposed. Most of the other residues (Ile7, Argl11, Ser20, and Phe27) which also appear to influence ShK toxin binding are clustered around these two residues. Only Lys30 is not found within this binding surface. This residue appears to be involved in a salt bridge with Asp5, and thus an Ala substitution may slightly alter the binding properties due some minor conformational change. It is also possible that this site may interact with one of the walls of the K channel outer vestibule similar to the perimeter basic residues in the charybdotoxin homologs (Aiyar et al., 1995).

Thus, as with charybdotoxin (Park and Miller, 1992; Stampe et al., 1994), ShK toxin binding to the delayed rectifier Kv1 type K channels apparently is dependent upon only a few side chains on the toxin surface. In charybdotoxin, Lys27 is most important and apparently penetrates into the pore of the channel. Lys27 occurs at a β turn in charybdotoxin (Bontems et al., 1992). In the recently reported solution structure of ShK toxin, the critical Lys22 and Tyr23 side chains reside in an α-helical segment of the toxin. Thus, ShK toxin appears to use a totally novel scaffold to orient a very similar binding surface or pharmacophore into the outer vestibule of the K channel.

Example 6—Truncated ShK Toxins

Several studies have provided evidence for the importance of the C-terminal third of the scorpion DR toxins for binding to the DR channels. Truncation or deletion of the last five or so residues greatly reduces affinity and blocking activity (Vita et al., 1993; Bednarek et al., 1994). Romi et al., (1993) also found the C-terminal peptide fragments of kaliotoxin were capable of inhibiting the binding of kaliotoxin to rat brain K channels. Two truncated ShK toxins have been synthesized, both lacking the last five residues. These were initially made for the purpose of identifying the disulfide pairings, and actually contain disulfides that are now known to not occur in ShK toxin:

Dicyclic:

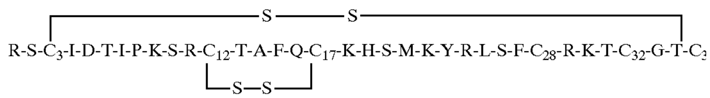

Monocyclic:

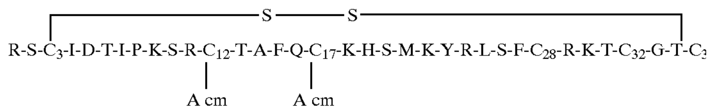

The dicyclic sequence shown above is SEQ ID NO:60 and the monocyclic sequence shown above is SEQ ID NO:61.

Both toxins, despite being chemically rather different from the natural toxin, displaced radioinodinated dendrotoxin from rat brain membranes with $IC_{50}$s of about 1 μM (100× greater than for ShK toxin). These results suggest that the C terminal five residues are not essential for activity, as they are in the scorpion toxins.

5.6.1 Architecture Of The Kv1.3 Outer Pore (Vestibule)

Architecture of the external entryway to the Kv1.3 pore has been partially mapped with scorpion toxins. The architecture of the entryway to the K+ channel pore was determined using four structurally-related, high-affinity scorpion toxin-blockers as molecular calipers. Paired mutagenesis of toxin and channel, combined with electrostatic compliance and thermodynamic mutant cycle analyses, identified five specific pairs of toxin:channel interactions. The spatial arrangement of these amino acids in the pore-forming region of Kv1.3 was deduced from the disposition of the corresponding residues in the NMR-determined structures of the toxins. The external vestibule, limited by the positions of these channel residues, is ~4–8 Angstroms (Å) deep, ~30–34 Å wide at its outer margin and ~28–34 Å at its base. The entrance to the ion conduction pathway is 9–14 Å across, and this narrows to <4.2 Å wide) at a distance of ~5–7 Å from the vestibule. This structural information aids in developing topological models of the pore-forming regions of related potassium, sodium and calcium channels. Additional mapping with these and other toxins may more precisely define the structure of the K+ channel pore.

ShK toxin blocks Kv1.3 at picomolar concentrations ($K_d$=~100 pM). Mutations in the P-region dramatically alter ShK blocking affinities, consistent with the toxin's interaction with residues in the external vestibule. Since ShK's structure appears to be unrelated to that of the scorpion toxins, it must dock in the Kv1.3 vestibule with a different geometry, thus potentially allowing the identification of new contact points between toxin and channel.

5.6.2 Estimated Dimensions Of The Vestibule

Evidence has been provided for the close proximity of several pairs of residues in Kv1.3 and KTX (D386-R24, H404-F25, G380-R31/L15) and ChTX (H404-R25, G380-W14/K31). Knowing the spatial relationships between these residues in KTX (R24, F25, L15, R31 and K27) and ChTX (W14 and K31) based on their NMR structures, it should now be possible to estimate the dimensions of the toxin-receptor.

A computer model of the toxin-binding site of Kv1.3 is being used to conceptualize toxin docking to the vestibule. Assuming that Kv1.3 forms a homotetramer with four-fold symmetry, and that K27 protrudes into the center of the pore, the dimensions of the toxin-binding site are as follows: D386 is ~14–17 Å from the center of the pore, based on the distance from the Ca of K27 and the farthest-reaching position of R24 in KTX; this would place D386 residues of opposing subunits 28–34 Å apart. H404 is 9–14 Å from the H404 on the opposing subunit (or 4.5–7 Å from the central axis of the pore) based on the $C^\alpha$ to $C^\alpha$ distance between K27 and either R25 in ChTX (~7 Å) or F25 in KTX (~7 Å), or on the size of TEA or a hydrated potassium ion (8–9 Å; Ohnishi et al., 1993; Kavanaugh et al., 1992). D386 is ~11 Å from H404, based on the sum of the measured distance between R24 and H404 (7–8 Å), and R24 and D386 (3.5 Å).

The outer mouth of the vestibule in the homotetramer is delineated by the positions of the G380 residues. The distance between opposing G380 residues is estimated to be 28–33 Å (or 14–18 Å from the central axis of the vestibule) based on the distance between residues 14/15 and 31 in ChTX and KTX, corrected for the additional space of two Gln side chains (~4 Å per side chain difference between Q and G; based on data showing that substituting Q for G380 converts a channel that is sensitive to KTX and ChTX to one that is resistant). The vertical depth of the vestibule is estimated to be ~4–8 Å, based on the distance between the Ca position of K31 in ChTX and a plane formed by the more distal carbon atoms of the side chains in R25 and M29, and the oxygen of Y36; this dimension is markedly smaller than the 10–15 Å suggested for the vertical depth of the shaker vestibule (Goldstein et al., 1994).

5.6.3 Model Of The Kv1.3 Vestibule:Docking Toxins

Using the estimated dimensions of the vestibule as constraints, a model of the Kv1.3 pore was constructed, and docked KTX and ChTX into the vestibule to identify new toxin-channel interactions. KTX docking: M29 is near H404 and N30 close to the opposite D386. Docking of KTX was achieved by guiding K27 into the center of the channel pore, then rotating the toxin about the central axis of the pore until R24 was aligned with D386. Interestingly, this configuration places F25 near 404, in support of experimental data. The three remaining H404s in the tetramer are close to G10, M29 and T36. This docking configuration places N30 close to D386 opposite to that interacting with R24. The proposed D386:N30 interaction is compatible with evidence showing that an aspartate at ChTX position 30 (N30D) completely abrogates the toxin's ability to block Kv1.3, possibly via electrostatic repulsion of D386); similar results have been obtained with N30D, N30E ChTX mutants on the Shaker channel (Goldstein et al., 1994).

These new interactions identified by the docking experiment permit further studies for mapping the vestibule. Recent studies have shown that a kaliotoxin analogue, agitoxin II (AgTX II), is an extremely potent blocker of Kv1.3 (Garcia et al., 1994). KTX and AgTX differ by only 4 residues (positions 3, 7, 9, 15), and surprisingly these are located in the N-terminus which is not thought to form part of the channel-interacting surface. Additional studies may help determine the channel residues that interact with these four critical AgTX-II residues, and contribute to the increased potency of the toxin. Docking ChTX:T8 is near G380. ChTX was docked into the channel by guiding K27 into the center of the pore, and then rotating the toxin about the central axis until W 14 and K31 projected towards G380 residues in opposing subunits. This configuration places T8 adjacent to a third G380 in the homotetramer. Consistent with this picture, Goldstein et al., (1994) reported that T8 in ChTX is close to the Shaker residue homologous to G380, namely F425.

5.7 EXAMPLE 7—Radioligand Binding Analysis Of Shk Toxins

The binding of ShK toxins was originally investigated indirectly by determining its ability to interfere with the binding of iodinated dendrotoxin to rat brain membranes (predominantly Kv1.2) and iodinated charybdotoxin binding to Jurkat lymphocytes. The IC50's were respectively 8 and 0.04 nM. Direct binding measurements are now possible, using mono-iodinated ShK toxins. The $^{125}$-ShK toxins specific binding displays a $K_D$ only slightly greater (37%) than unlabelled ShK toxins. Although specific as well as non-specific binding is ionic strength dependent, ShK toxin's binding is not inhibited as much by increasing ionic strength compared with ChTx. It is now possible to investigate the dependence of ShK toxins binding upon pH and K concentration. Scatchard analysis of the effect of ChTx upon 125I-ShK toxins binding indicates that the two toxins compete for a common site in rat brain membranes. The association rate of ShK toxin binding was also determined.

5.8 EXAMPLE 8—Structure-Activity Studies With Shk Toxin Analogs

The analogs and their ability to displace ChTx from lymphocytes or dendrotoxin from rat brain membranes are shown in Table 13. A CD spectrum quickly indicated whether the peptide had folded similar to the natural ShK toxins sequence. Two regions on the ShK toxins sequence have been found to influence the toxin's ability to interact with these two K channel preparations. The most impressive changes occur at Lys22, when substituted with Ala (no cationic group, smaller sidechain), Citrulline (no cationic group, but a planar guanidine-like sidechain), or Arg (bulky cationic group). Replacement with Ornithine (slightly shorter sidechain) reduced apparent affinity by about 120% (rat brain results). Using electrophysiological recording from cultured cells and Xenopus oocytes, that KV1.22A affinity for Kv1.3 is only slightly affected; however, the toxin is now much more easily washed from the receptor relative to the wild-type toxin which binds almost irreversibly (No washout after 20 min). Conservative substitutions of adjacent Met21 and Tyr23 residues do not significantly affect ShK toxins binding to rat brain K channels. These results indicate that Lys22 may be acting like Lys27 in ChTx, which interacts with Asp402. Lys22 is part of the second helix.

Another region which seems to interact with the Kv1.3 channel is near Lys9, Arg11, and Phe15. Although the rat brain K channels displayed almost no change in affinity for these analogs, the Jurkat cells displayed a 10-fold lower affinity for these analogs. The vestibule of Kv1.2 may be larger in this region, or the channel residues may not interact as readily with this region of the toxin. This region of the toxin may include a B-turn and a portion of the first helix, which begins at position 14.

Studies with monosubstituted analogs show that there are at least two regions which seem involved in binding to these K channels, which respond quite differently.

TABLE 13

ABILITY OF SHK TOXIN ANALOGS TO DISPLACE BINDING OF CHARYBDOTOXIN TO JURKAT LYMPHOCYTES AND DENDROTOXIN TO RAT BRAIN MEMBRANES 1          10          20          30
RSCIDTIPKSRCTAFQCKHSMKYRLSFCRKTCGTC (SEQ ID NO: 1)

| | | $IC_{50}$ (nM) | |
|---|---|---|---|
| Toxin Analog | Secondary Structure | Lymphocyte $^{125}$I-CTX | Rat Brain $^{125}$I-CTX |
| ShK | NORMAL | 0.04 | 8 |
| R1S | NORMAL | 0.05 | 16 |

TABLE 13-continued

ABILITY OF SHK TOXIN ANALOGS TO DISPLACE BINDING OF CHARYBDOTOXIN TO JURKAT LYMPHOCYTES AND DENDROTOXIN TO RAT BRAIN MEMBRANES

```
1        10        20        30
RSCIDTIPKSRCTAFQCKHSMKYRLSFCRKTCGTC (SEQ ID NO: 1)
```

|  |  | $IC_{50}$ (nM) | |
| --- | --- | --- | --- |
| Toxin Analog | Secondary Structure | Lymphocyte $^{125}$I-CTX | Rat Brain $^{125}$I-CTX |
| K9Q | NORMAL | 0.31 | 11 |
| R11Q | NORMAL | 0.64 | 18 |
| F15A | NORMAL | 0.54 | 6 |
| F15W | NORMAL | 0.65 | 6 |
| KV1.18A |  |  | 10 |
| M211le |  |  | 9 |
| KV1.22Orn |  |  | 20 |
| KV1.22R |  |  | 2000 |
| KV1.22A | NORMAL | >5 | 300 |
| KV1.22Cltr |  |  | 2000 |
| Y23F |  |  | 9 |
| Y23S | UNORDERED | >5 | >5000 |
| R24A | NORMAL | 0.04 | 10 |

TABLE 14

SHK TOXIN ON Kv1.3,3 MUTANTS

| Channel | Kd (nM) |
| --- | --- |
| H404 and ShK |  |
| Kv1.3.3 WT (pH 7.6) | 0.60 ± 0.6 (10) |
| Kv1.3.3 WT (pH 6.0) | 0.30 ± 0.08 (7) |
| H404Y | 4.0 ± 1.5 (6) |
| H404T | 0.30 ± 0.2 (6) |
| H404L | 3.2 ± 1.4 (4) |
| H404R | >100 |
| D386 and ShK |  |
| D386N | 0.40 ± 0.3 (r) |
| D386K | 1.8 ± 0.6 (5) |
| G380 and ShK |  |
| G30 | 0.60 ± 0.2 (2) |
| G380E | 0.60 ± 0.6 (6) |
| G380H | >100 |

TABLE 15

SHK TOXIN MUTANTS ON Kv1.3,3

| Toxin | Kd (nM) |
| --- | --- |
| WT | 0.70 ± 0.50 (4) |
| Y23F | 0.22 ± 0.05 (3) |
| Y23-p-nitro-F | 0.20 ± 0.08 (6) |
| Y23-p-amino-F | 0.12 ± 0.00 (2) |
| Y23S | 150 |
| KV1.22Orn | 2.0 ± 1.0 (3) |
| KV1.22R | 6.6 ± 0.8 (2) |
| KV1.22Homocit | >100 |
| KV1.22A | 0.33 ± 0.20 (9) |

5.9 EXAMPLE 9—High-Level Expression Of Kv1.3 Channels For Shk Binding Studies

Integral membrane proteins including receptors, transporters, and ion channels are critical for the transfer of both signals and substrates between the external and internal environments of cells. Although the genes for many of these mammalian proteins have been isolated, and site-specific mutagenesis studies have mapped functional domains, not a single mammalian integral membrane protein has had its 3-dimensional structure solved. Such information would clearly define how protein structure relates to function, and could guide pharmaceutical efforts to develop novel therapeutic agents. The primary impediment to structural analysis is the lack of a method for large scale expression and purification of intact protein. The disadvantages of existing heterologous non-mammalian expression systems for purifying mammalian proteins includes inappropriate posttranslational modification and protein accumulation in inclusion bodies. A vaccinia virus based heterologous expression system has been developed for over-expression and rapid purification of appropriately folded and modified Kv1.3 at adequate amounts for direct structural analyses.

The gene for Kv1.3 was cloned into a vaccinia transfer vector (pTM1) in-frame with an 111 bp sequence encoding a polyhistidine repeat, a segment from gene 10 of bacteriophage T7, and an enterokinase cleavage site. Expression of this fusion protein in African Green monkey kidney cells, CV-1, produced 1–5×10⁵ functional K+ channels which are biophysically identical to native Kv1.3. The heterologously expressed channel was glycosylated like its native counterpart in lymphocytes. These Kv1.3 expressing cells have been used for radiolabeled ChTX binding studies, and are adaptable to ShK binding.

Gel filtration and sucrose density gradient sedimentation analyses suggested that purified Kv1.3 protein retained its native tetrameric structure. As few is $10^7$ cells yielded 50 mg of homogeneous Kv1.3 protein, making it easily possible to upscale this method to produce adequate quantities for structural studies such as 2-dimensional crystallography, electron microscopy and spin-label topology mapping. The purified protein when reconstituted into lipid bilayers produces functional channels which are blocked by ShK and by MgTX. The protein also binds radiolabeled MgTX. The method described here has wide implications for the purification and direct structural analyses of any integral membrane protein.

5.9.1 Analysis Of Shk Toxin Analog Radioligand Binding To Kv1.2 And 1.3K Channels By measuring the equilibrium dissociation constant KD for interaction of the ShK toxin analog with the two K channel preparations, it is possible to obtain a measure of the Gibbs free energy of binding, F=–RT ln KD. Subtraction of this from the corresponding value for the natural ShK toxin sequence provides an estimate of the Δ (ΔF) associated with the change in the sidechain, or portion of the toxin that is either removed or substituted:

$$\Delta F - \Delta FA = RT \ln K_{D(A)} - RT \ln K_D$$

If the contributions to binding of each sidechain were completely (1) independent, (2) additive, and (3) known, one could in principle predict the $K_D$ for any toxin sequence. This example relates to the determination of the relative importance of the various sidechains present in the pharmacophore region of ShK toxin, the so-called "hot-spots" which are dominating the interaction with Kv1.3 channels. Knowledge of these residues is essential for the rational design of simpler peptidomimetic molecules that will bind to the same region of the Kv1.3 channel.

$K_D$ measurements are performed as reported above. All incubations and washings of membranes or cells are done at room temperature, unless the rates of dissociation of some of the analogs are so fast that they must be slowed by washing the filters at ice-cold temperature. Natural ShK toxin dissociates quite slowly from the Jurkat cells and rat brain membranes. Steady state displacement curves and Scatchard plots are constructed with a minimum of 12 points.

Radioligand binding experiments permits not only measurement of the equilibrium dissociation constant for interaction of each ShK toxin analog with these two K channels in naturally expressing cells, but also separate estimation of the association and dissociation rate constants for the interaction. This, in turn, facilitates the assessment of whether a substitution is affecting the formation of the initial encounter complex (EC) or its subsequent binding to the channel, as described by Escobar et al., (1993):

$$T + C \underset{k_{-1}}{\overset{k_1}{\rightleftarrows}} EC \underset{k_{-2}}{\overset{k_2}{\rightleftarrows}} B$$

where $k_1$ and $k_{-1}$ transitions represent diffusion up to and away from an encounter complex (EC). The $k_2$ and $k_{-2}$ transitions involve rearrangements permitting tight binding with the receptor. Assuming that a steady-state concentration of the EC occurs, the association (a) and dissociation (B) rate constants are respectively $$\text{If } k_{-1} >> k_2, \text{ then } \begin{matrix} a = k_1 k_2 / k_{-1} + k_2 \\ a = k_1 k_2 / k_{-1} \end{matrix} \text{ and } \begin{matrix} B = k_{-1} k_{-2} / k_{-1} + k_2) \\ B = k_{-2} \end{matrix}$$

this predicts that the association rate constant will be more dependent upon long range forces like electrostatic potentials on the toxin and the K channel vestibule (Escobar et al., 1993). Obviously sidechain substitutions which do not affect the charge at that position would be less likely to affect the association rate constant in i manner dependent upon ionic strength of pH.

The association rate constant a is determined from the following plot:

$$a = k_{obs} \left( [LR]_e / ([L][LR]_{max}) \right)$$

where [L] is the $^{123}$I-ShK free concentration, $[LR]_e$ is the concentration of the radioligand-receptor complex at equilibrium, $[LR]_{max}$ is the maximum concentration of receptors present, and $k_{obs}$ is the slope of the pseudo-first order plot $\ln([LR]_e/([LR]_e - [LR]_t))$ versus time (Weiland and Molinkoff, 1981).

The dissociation rate constant is determined by plotting the relation $$\ln(LR)_t/(LR)_e = -k_{-1} X_t$$

Radiolabeled toxin disassociation may generally be initiated by diluting the membrane suspension 50-fold, and removing aliquots at different times for radioactivity measurements.

It is possible to determine whether the rate of association of ShK toxin is fast enough to be diffusion-limited, or like ChTx, even faster. Disregarding the possible ionization of the His residue, ShK toxin has 9 + charges and 2 – charges. Thus it is even more basic than ChTx. The inventors thus predict that its rate of association with DR K channels will also be relatively fast. The Kv1.3 channel displays about a 50-fold higher affinity for ShK toxin relative to rat brain K channels, which are mostly Kv1.2; it is not yet known if this big difference in $K_D$S is due to differences in rates of association or dissociation.

The rates of binding and unbinding of the various ShK toxin analogs may be determined using the radioiodinated toxin analog prepared under standard conditions to optimize mono-iodination. Analogs in which the Tyr 21 is substituted may be iodinated at the N-terminus with the Bolton-Hunter reagent at pH 7.5.

5.10 EXAMPLE 10—Complementary Mutagenesis:Interaction Of Shk Toxin Analogs With Kv1.3 Mutants 5.10.1 Generating Mutants Channel mutants were generated using a two-step PCR™ method using sense and anti-sense mutant primers (Ho et al., 1989); mutations were confirmed by dideoxy sequencing. cRNA was transcribed in vitro using an mCAP Kit (Stratagene, La Jolla, Calif.) and injected into oocytes (*Xenopus laevis* purchased from NASCO, Wisconsin) as previously described (Grissmer et al., 1990; Soreq and Seidman, 1992). All experiments were done at room temperature (20–26° C.). K+ currents were measured using the two-electrode voltage-clamp technique (Soreq and Seidman, 1992) and data analyzed using pClamp software (version 5.5.1, Axon Instruments, Burlingame, Calif.). Whole oocytes were held at −100 mV and depolarized to +40 mV over 500 ms. Time between pulses was 30 sec. Capacitative and leak currents were subtracted prior to analysis using the P/4 procedure. After recording baseline Kv1.3 currents from oocytes, the ND96 bathing solution was replaced with the toxin solution; the perfusion rate was adjusted to facilitate complete exchange in ~30 sec.

The dissociation constants (Kd) were calculated using the formula: Kd=concentration of toxin/[(1/fraction of unblocked current)−1], assuming a 1:1 binding of toxin to a channel as described previously (Grissmer et al., 1994). The ND96 solution used in these experiments contained (in mM): 96 NaCl/2 KCl/1.8 $CaCl_2$/1 $MgCl_2$/5 HEPES/5 Na pyruvate at pH 7.6. Oocytes expressing Kv1.3 wild-type and H404T channels were perfused with ND96 containing 0.1% BSA at the indicated pH to record control currents, followed by perfusion of the toxin at the same pH. Kv1.3 mutants (G380T, G380E, G380Q) were obtained from Richard Swanson (Merck Sharpe and Dohme, West Point, Pa.).

5.10.2 Electrostatic Compliance Measurement Of Distance Between D386 And R24

Electrostatic compliance is a measure of the strength of the charge-charge interaction between two specific residues, one on a toxin and one on the channel to which it is bound (Stocker and Miller, 1994). Electrostatic compliance values were calculated from the slopes of the two curves for a given set of toxin: channel mutants at 100 mM and 25 mM salt. The theoretical form of the electrostatic compliance is given by:

$$\sigma(i, j) = \frac{\partial(\ln K_d)}{\partial qchan \partial qtox} = \frac{e^2 \exp(-rij/\lambda D)}{kT4\pi\varepsilon_o D\gamma rij} \qquad \text{Equation 1}$$

where $r_{i,j}$ is the separation between the toxin charge and the channel charge, e is the electronic charge, k is the Boltzmann constant, $\epsilon_o$ the permitivity of free space, D is the dielectric constant (taken as 80), and q is a geometric factor which takes into account the electrostatics of the dielectric interface between water and protein (taken as 0.8). Separation between interacting charges was estimated by solving equation 1 for $r_{i,j}$ graphically using the experimentally determined values of the electrostatic compliance.

Selecting an appropriate value for the dielectric constant in this equation is not trivial. Stocker and Miller (1994) justified the use of a dielectric constant of 80 by limiting their analysis to residues near the aqueous interface. Data on globular proteins indicates that this is likely to be a good approximation (Honig et al., 1984; and Gilson et al., 1985), but the situation is not so straightforward for residues deeper in the vestibule. The inventors have used a value of 80 for the dielectric constant for two reasons. First, bulk water parameters were used by Hidalgo and MacKinnon (1995) to estimate distance between D431 in the Shaker channel, a residue deep in the pore, and R24 in agitoxin. Second, the vestibule has four-fold symmetry and the toxin has no rotational symmetry. The volume of the toxin must therefore be considerably less than that of the vestibule, leaving room for water between the toxin and the channel. Thus the relevant dielectric constant may be close to that of bulk water, even deep in the vestibule.

5.10.3 Electrostatic Compliance Measurement Of Distance Between H404:Chtx-R25 And Ktx-R24:

The inventors generalized the electrostatic compliance method to include charge changes induced by titration. To obtain an experimental value of electrostatic compliance (defined in Equation 1), the inventors calculated the change of LnKd for a given change in channel charge, for both ChTX and ChTX-R25D. The inventors assume that the partial charge on the channel is described by the equation:

$$q_{his} = K_d[H^+]/(1+K_d[H^+])$$ Equation 2 where Kd is the dissociation constant, and [H+] is the proton concentration. the derivative of pH with respect to charge, $1/[q_{his} \ln(10)]$, was multiplied by the least square slopes (obtained from the experimental data), to give the term $d(1\text{nKd})/dq_{his}$, where $q_{his}$ is the partial charge on the histidine (in units of electronic charge) and varied from 0 to +1. The electrostatic compliance value was then determined by subtracting the slope of WT toxin from that of its mutant (ChTX-R25D or KTX-R25D), and dividing the value by 2 (the absolute change in charge on the toxin). For these calculations the inventors assumed the dielectric constant to be 80, and a pK for the histidine of 6.2 (also see Creighton, 1984). The value of $dpH/dq_{his}$ at pH 6.4, the midpoint of the experimental curve, was calculated.

5.10.4 Thermodynamic Mutant Cycle Analysis

Hidalgo and MacKinnon (1995) defined X as:

$$\Omega = \frac{Kd[\text{WT toxin:WT Kv1.3}] \times Kd[\text{mut toxin:mut Kv1.3}]}{Kd[\text{mut Kv1.3:WT toxin}] \times Kd[\text{WT Kv1.3:mut toxin}]}$$ Equation 3

$\Omega$ is a measure of the interaction between toxin and channel residues, a value of 1 representing no coupling, and values progressively different from 1 indicating progressively stronger interactions. The difference in free energy of an interaction between specific residues in wild-type/wild-type versus mutant/mutant interactions is given by:

$$RT\ln\Omega = RT\ln(Kd_{ww}/Kd_{mm})$$ Equation 4

The equation, $E=RT\ln\Omega$, converts $\Omega$ values into coupling energies. Assuming bulk water parameters and using Debye-Huckle theory, the inventors used coupling energies to estimate charge-pair separations by solving the following equation for r:

$$f(r, q1, q2, \lambda D) = \frac{q1q2\varepsilon^2 \exp(-r/\lambda\omega)}{4\pi\varepsilon_o D\gamma r}$$ Equation 5 where q1 is the change in charge on the channel between mutant and WT, D is the dielectric constant, $\epsilon_o$ is the permitivity of free space, $\gamma$ is a distance-dependent geometrical factor described above, which has been taken as 0.8, and $\gamma D$ is Debye length.

5.10.5 Modeling Structures

Modeling the Kv1.3 pore. The Shaker and Kv1.3 channels are remarkably similar in the pore region, differing at only six positions in the region spanning Shaker residues F425 and G455 (Chandy and Gutman, 1995). To create a good model of the Kv1.3 channel pore, F425, K427, T449, G452, F453, and W454 in the model of the Shaker channel (Guy and Durell, 1994) were mutated to G380, N382, H404, T407, I408 and G409, respectively. assuming perfect 4-fold symmetry, the distances estimated for residues G380, D386, and H404 were included as constraints during minimization of the channel with SYBYL. Further refinements of this model will be made based on the data obtained from mapping the ShK structure onto the Kv1.3 vestibule.

5.10.6 A Recombinant Vaccinia Virus Expressing KV1.3 For High-Affinity Binding Studies Studies by Moss and collaborators have demonstrated the utility of the vaccinia virus system for heterologous expression of proteins in mammalian cells. A vaccinia transfer vector, pTM1 was developed for this purpose. the key features of this construct are as follows:

i) It contains an upstream non-coding region from EMC virus and an initiator methionine codon (AUG) which provide, a very efficient translation initiation site.

ii) The transcription initiation and termination sites for the T7 polymerase facilitate efficient transcription of full-length mRNA by this polymerase, which is provided by a separate vector.

iii) The two halves of the thymidine kinase gene can be used to transfer the cloned sequence into an infectious vaccinia virus construct by homologous recombination.

iv) Two origins of replication allow for production of either double-stranded or single-stranded DNA in E. coli, and an ampicillin-resistance gene permits drug selection.

This vector was modified for protein purification (pTH1), as follows. The initiator methionine codon (AUG) in pTM1 was fused in-frame to six tandem histidines. This histidine motif allows for binding and elution from a $Ni^{2+}$-bearing column as the first step in protein purification. This is followed by a gene-10 sequence derived from bacteriophage T7 that can be targeted by a commercially available monoclonal antibody, permitting the detection of protein by Western blotting and its isolation by immunoprecipitation. Third, an enterokinase site and a multiple cloning site links the epitope sequence to the inserted gene; it can be used, if desired, to remove the superfluous sequence.

The pTM1 and pTH1 constructs can be used for transient expression in mammalian cells in either of two ways: by transfection/infection, or by double infection. In the first case, transfection of target cells with a construct containing the sequence of interest (VV:Kv1.3), is followed by infection with T7 polymerase-encoding vaccinia virus (VV:T7), resulting in T7-dependent transcription and subsequent translation of protein. Alternatively, VV:Kv1.3 can be recombined into a virus and used to infect target cells simultaneously with the VV:T7, with similar results. The advantage of the latter method is that infection is more efficient than transfection in introducing DNA into target cells; on the other hand, while the plasmid required for transfection can be made easily, the process of producing recombinant viruses for the dual infection takes considerably more time.

To find an appropriate cell type for VV-mediated expression of channels, the inventors have tested Kv1.3 expression in several cell lines (CV-1, HeLa, Jurkat T cells, Rat Basophilic Leukemic cells, U937, NIH-3T3-fibroblasts); CV-1 cells provide the highest yield of the protein. CV-1 cells do not express endogenous voltage-gated or inwardly rectifying $K^+$ channels, and therefore provide an electrically silent background for electrophysiological analysis of $K^+$ channels. Another advantage is that these cells express biophysically "normal" Kv1.3 channels even after block of glycosylation by tunicamycin, suggesting that immature forms of protein are functional. Additionally, CV-1 cells can be adapted to spinner cultures. Each of these cell lines will be examined for their sustain high-level expression of functional Kv1.3 channels.

5.11 EXAMPLE 11—Photoaffinity Analogs Of Shk Toxin

Although the primary sequence of the K-channel receptor has been deduced from corresponding cDNA channels, the extracellular residues contributing directly to the formation of the ShK toxin binding pocket are entirely unknown. On the other hand, residues on ShK which contact the receptor may be identified during the course of these analog studies. At this time, Lys9, Arg11, Lys22 and Tyr23 appear to interact with receptors on the Kv1.2 and Kv1.3 channels. To map site-site interactions between ShK toxin and the K-channel receptor, the inventors will prepare photoactivatable ShK toxin analogs. Photoactivatable amino acid derivatives are easily incorporated into standard solid-phase peptide synthesizers. The receptor (primarily Kv1.3, but also rat brain K channels) radioligand binding characteristics of toxin analogs containing a photoreactive group may be studied prior to performing photolabeling experiments. The photoreactive amino acid derivatives include p-azido-phenylalanine and p-benzoyl-phenylalanine (Bpa). p-azido-phenylalanine has been successfully employed to affinity label the human thrombin receptor with a synthetic analog which incorporated a p-azido-Phe residue in place of Leu (Bischoff et al., 1994). This amino acid residue is stable to synthesis conditions. Furthermore, it is a suitable replacement for aliphatic residues such as Ile, Leu and Val as well as the aromatic residues Phe, Tyr and Trp.

An alternative photolabel is p-benzoyl-Phe (Bpa). This amino acid derivative is also very stable to the solid-phase synthesis conditions and has a high efficiency for forming cross-links (Kauer et al., 1986). Furthermore, Bpa has the added feature of incorporating a benzophenone moiety which undergoes a $n\_\pi^*$ transition to give a triplet biradical that has a high reactivity for C—H bonds which likely line the surface of the ShK toxin receptor. This amino acid derivative has been incorporated successfully into a calmodulin-binding peptide (Kauer et al., 1986) substance P (Boyd et al., 1991) and into several semisynthetic insulin analogs (Shoelson et al., 1992). Positioning of this derivative within the ligand chain has been shown to affect the ability to form covalent cross-links with the receptor (Shoelson et al., 1992). This data has been interpreted as suggesting that these residues are probably not buried within the receptor-ligand complex. This derivative is more sterically encumbering and may be useful in cases where poor low-efficiency cross-linking with the p-azido-Phe derivative is encountered.

In order to identify where the ShK-toxin affinity probe has inserted into the K-channel receptor, radiolabeling or biotinylating of ShK affinity label is required. radiolabeling may be accomplished either by radioiodination or derivatization with label containing [$^3$H] or [$^{14}$C] such as N-terminal capping with acetic anhydride in the last synthetic step. The N-terminal Arg1 has been replaced with Ser without any change of biological activity. This suggests that the N-terminus is not essential for binding and acetylation of the N-terminal a-amino group should be tolerated. If iodination is utilized, incorporation of iodine at either the His or Tyr residue will be limited to His if the photolabel Bpa or p-azido-Phe for Tyr23 is used. If radiolabeling is a problem or not desired, the N-terminal amino group may be selectively biotinylated (Lobl et al., 1989; Pennington, 1994) allowing the covalently attached ShK toxin-K-channel receptor to be identified using a biotin-avidin type interaction.

Lastly, amino groups may be conveniently modified on the solid-phase with p-benzoyl-benzoic acid (BBA) provided that selective orthogonal protection amino groups are utilized (Gorka et al., 1989; Pennington, 1994). By employing a Lys or Orn derivative with an Alloc or Methyltrityl protecting group, selected positioning of a Lys(BBA) or Orn(BBA) may be achieved. This will allow the inventors to not only look at those residues present in hydrophobic "patches" within the ShK sequence but in the more hydrophilic regions as well. Provided that the substitution is not extremely disruptive for binding, an additional set of contact points on the receptor may be identified. Additionally, this BBA derivative is commercially available in a tritiated form to facilitate analysis of the proteolytically derived receptor peptides containing the BBA insertion.

Irradiation at 366 nm causes the BBA and Bpa containing ShK analogs to photochemically insert into the receptor surface (Kauer et al., 1986; Shoelson et al., 1992). Irradiation at 300 and 350 nm causes the p-azido-Phe containing ShK analogs to photochemically insert as well (Bischoff et al., 1994). The photochemically derivatized toxin-receptor complex may now be digested with proteases such as: thermolysin, chymotrypsin, Glu-C and Asp-C (Pohl et al., 1995). The receptor derived covalently modified peptide or peptides may be purified by microbore RP-HPLC if the radiolabel approach is utilized or by biotin-avidin chromatography of the biotinylation approach is followed. These approaches have been utilized successfully to define the scorpion toxin receptor site and the brevetoxin receptor site on voltage-sensitive Na channels (Tejedor and Catterall, 1988; Trainer et al., 1994). Purification of particular segments of Kv1.3 can be facilitated by immunoprecipitation with an antibody against the gene 10 tag at the N-terminus.

5.12 EXAMPLE 12—Peptidomimetic Analogs Of Shk Toxin

The present example relates to the synthesis of peptidomimetic prosthetic units to replace the three basic building blocks of ShK toxin: (α-helix, β-sheets and reverse turns). Literature reports have focused around the importance of reverse turns in biological recognition events (Ball and Alewood, 1990). Reverse turns are capable of participating in biological recognition events in either an active role, where the precise spatial orientation of pharmacophoric information is critical (Smith and Pease, 1980), or in a more passive manner of properly positioning two peptide chains as they enter and exit the reverse turn (Niwa et al., 1993). The strategy focuses on turn mimetics which will address both of these turn situations simultaneously. Analysis of the tertiary structure of ShK in combination with the contact point refinement studies permits the definition of the pharmacophore surface of ShK toxin.

β-Turns constitute tetrapeptide units which cause a reversal of in direction of the peptide chain. Turns are described as the distance from the $C_a$ of the first residue to the $C_a$ of the fourth residue. If this distance is less than 7 Å and the tetrapeptide sequence is not in an α-helical region it is considered a β-turn. Additionally, three residue reverse turns (γ-turns) are also possible but less common. These procedures are adaptable to either solid-phase or solution phase methods. Synthesis of the reverse turn mimetic involves the coupling of the first modular component piece (1), to the amino terminus of a growing peptide chain (2). Coupling of the second modular component (3), removal of the protecting group P' and subsequent coupling of the third modular component (4) provides the nascent β-turns (5). The critical step in this sequence involves the use of an azetidinone as an activated ester to effect the macrocyclization reaction (Wasserman, 1987). Upon nucleophilic opening of the azetidinone by the X-moiety, a new amino terminus is generated for continuation of synthesis. An important feature of this scheme is the ability to alter the X-group linker, both in regard to length and degree of rigidity/flexibility. The synthesis allows commercially available building blocks of either L or D stereochemistry to be utilized. Furthermore, deleting the second modular component (3) provides access to γ-turn mimetics. By utilizing these types of turn mimetics, none of the pharmacophoric information is lost and a stable reversal of chain direction is achieved.

A peptidomimetic compound was recently prepared in six steps utilizing Scheme 1 which effectively mimics a loop present on the CD4 receptor which binds to HIV gp120 protein (Chen et al., 1992). This compound effectively blocked gp120 binding to CD4 receptor at low micromolar concentrations and effectively reduces syncytium formation 50% at 250 µg/ml.

Relatively few attempts have been made to initiate or stabilize α-helices with small synthetic molecules (Kemp et al., 1991). Most efforts in this area have relied upon positioning Lys and Asp residues on the same face of amphiphilic helical surfaces spaced i+4 residues apart and form an isopeptide bond between the sidechains to stabilize the helix (Chorev et al., 1993; Kanmera et al., 1995). Other attempts at positioning stereoisomers of Cys with the same distance forming an i+4 disulfide bridge between the L-Cys and D-Cys residues has also been reported (Krstenansky et al., 1988). The problem with this approach is that any sidechain interaction at these two positions is effectively lost. Thus, mimetics which enhance the initiation of an α-helix in peptides may offer a better alternative.

Helical initiator compounds 1 and 2 are cyclic compounds derived from aspartic acid and glutamic acid, respectively (Meara et al., 1995). Each of these cyclic helical initiator compounds may be incorporated at the N-terminus of the helical segment of ShK, and the biological activity of this short helical mimetic assessed. Additionally, this helical initiator modular component may be conveniently incorporated into a solid-phase assembly permitting the synthesis of full-length analogs incorporating this compound.

The pharmacophore surface assessment and the analog-based contact point refinement data forms the basis for the design of peptidomimetic compounds. The contact point side-chain refinement data allows the optimization of potential K-channel interaction points by having a better understanding of geometry, distances, charge and hydrophobicity of the reciprocal K-channel interaction site. The analogs studied in modifying the K-channel selectivity of ShK toxin may be utilized in designing peptidomimetic compounds which are specific for a particular K-channel subtype.

Compounds which show a degree of similarity to the ShK pharmacophore will be tested for K-channel binding. Any compounds found to have binding affinity will constitute valuable new leads, which could then be modified with the aim of improving binding affinity and channel sub-type specificity. Even if matching compounds do not display binding initially, they may still serve as useful leads in the development of mimetic compounds in that they could represent useful structural scaffolds for further synthetic manipulation. In either case a close interaction between modelling and conformational analysis by NMR will be maintained in order to guide the synthetic program.

5.13 EXAMPLE 13—Shk-K22DAP: A Potent KV1.3-Specific Immunosuppressive Peptide

This example describes the ShK mutant, ShK-K22DAP, which potently and selectively blocks the T-lymphocyte potassium channel, Kv1.3 (Table 16). The half-blocking dose for Kv1.3 is 28 pM. ShK-K22DAP is 100-fold less potent as a blocker of closely related channels: Kv1.1 (Kd=3.4 nM), Kv1.2 (5 nM); Kv1.5 (Kd>100 nM), Kv3.1 (Kd>100 nM), small conductance calcium-activated potassium channel in T-cells (Kd=10 nM). The mutant is more selective than the native peptide, ShK, which blocks Kv1.1 and Kv1.3 with similar potency (Kd=~10 pM).

Peptide and non-peptide antagonists of Kv1.3 are immunosuppressive in vitro and in vivo. Due to its distinct mechanism and restricted tissue distribution, a specific and potent Kv1.3 blocker like ShK-K22DAP would not likely display the toxic side-effects of currently used immunsuppressants such as cyclosporin and FK-506. Therefore, ShK-K22DAP or related mutants may prove useful for treatment of chronic autoimmune diseases as well as transplantation therapy.

The ShK-K22DAP or its related mutants may also be useful as a structural template for the design of novel organic antagonists of Kv1.3. To confirm this use of ShK-K22DAP, 5 ShK mutants were analyzed. The selection was based on earlier work that defined precise toxin-channel interactions and was made from a bank of over 40 ShK mutants. Attention was focused on lysine 22 of the toxin; this residue interacts with the ion conduction pathway and occludes the pore. The ShK-K22DAP mutant, maintains the positive charge at toxin-position 22, and is able to block the Kv1.3 (channel with almost equal potency as the native toxin, while losing >100-fold potency against Kv1.1 (Table 16). Other closely related channels are >100-fold less sensitive as well. This mutant peptide is therefore a highly selective and potent blocker of Kv1.3. This peptide or related mutants may be useful for transplantation therapy and for the treatment of chronic autoimmune diseases.

TABLE 16

DATA ILLUSTRATING THE SELECTIVITY OF THE SHK-K22DAP MUTANT FOR Kv1.3

| Toxins | Kvl.1 | Kv1.2 | Kv1.3 | Kv1.5 | Kv3.1 | IKCa |
|---|---|---|---|---|---|---|
| ShK | 16 ± 3 pM** | 9 ± 0.3 nM | 12 ± 2 pM** | >100 nM | >100 nM | 28 ± 3.3 nM |
| n = | (3) | (2) | (2) | (3) | (3) | (3) |
| K22DAP | 3 ± 0.2 nM | 39 ± 3.2 nM | 23 ± 3 pM** | >100 nM | >100 nM | >100 nM |
| n = | (2) | (3) | (4) | (3) | (3) | (3) |

5.13.1 Materials And Methods 5.13.1.1 Peptide Synthesis

Fmoc-amino acid derivatives were obtained from Bachem Feinchemikalien (CH-4416 Bubendorf, Switzerland). Solid-phase assembly was initiated with Fmoc-Cys(Trt)-2-chlorotrityl resin in order to minimize potential racemization of the C-terminal Cys residue. Automated stepwise assembly was carried out entirely on an ABI-431A peptide synthesizer (Applied Biosystems, Foster City, Calif.). Fmoc-Dap(Boc) was substituted in place of Lys at position 22 in the assembly of the peptide. Following removal of the final Fmoc protecting group, the Dap22 substituted peptide was cleaved and deprotected with reagent K (King et al., 1990) containing 5% triisopropylsilane. The crude product was precipitated into diethyl ether and subsequently dissolved in 20% AcOH. Oxidative folding of the peptide was initiated by dilution of the solubilzed product into water (2 l) and adjustment of the pH to 8.0 with NH40H. After folding for 2 h, oxidized and reduced glutathione were added to a final concentration of 1 mM, and folding allowed to continue overnight. The ShK Dap22-analog was purified using RP-HPLC as previously described (Pennington et al., 1996). HPLC-pure fractions were pooled and lyophilized. The structure and purity were confirmed by RP-HPLC, circular dichroism spectroscopy, amino acid analysis and ESI-MS analysis. All other ShK analogs were synthesized, purified and characterized as previously reported (Pennington et al., 1996a,b).

5.13.1.2 Proteolytic Digestion Of Shk-K22Dap

Sequencing grade trypsin and chymotrypsin were obtained from Sigma. ShK-Dap22 (200 μg per assay) was treated with trypsin, chymotrypsin or a 1:1 mixture of the two proteases at a substrate to enzyme ratio of 50:1 in 50 mM sodium phosphate pH 6.5. Aliquots from each assay were removed at 15, 30 and 60 min and quenched with 50 μl of 10% TFA in H20. Each sample was analyzed by RP-HPLC using an aqueous acetonitrile gradient to separate the digestion mixture.

5.13.1.3 Reagents

Cell lines stably expressing Kv1.1, Kv1.2, Kv1.3, Kv1.5 and Kv3.1 were maintained in Dulbecco's modified Eagle's medium containing 10% fetal calf serum and G418 (1 mg/ml). IKCa channels were studied in activated human T-cells and all Kv1.3 mutants used have been described (Aiyar 1995, 1996).

5.13.1.4 Abbreviations

AcOH, acetic acid, Fmoc, fluorenylmethyloxycarbonyl, Boc, t-butyloxycarbonyl, Dap, diaminopropionic acid, ESI-MS, electrospray ionization-mass spectroscopy.

5.13.1.5 Activation Of Human T-cells By Anti-CD3 Antibody

For electrophysiological analyses, most studies were carried out in the whole cell configuration of the patch clamp technique. All membrane currents were recorded at room temperature with an EPC-7 amplifier (Heka Electronik, Lainbrecht, Germany). Series resistance compensation was used if the current exceed 2 nA. Capacitative and leak currents were subtracted using the P/8 procedure. The command input of the EPC-7 amplifier was controlled by a PDP 11/73 computer via a digital-to-analog converter. The holding potential in all studies was −80 mV.

5.13.2 Results 5.13.2.1 Shk Is A Potent Blocker Of Kv1.3, Inhibits T-cell Activation The T-lymphocyte channel, Kv1.3, is a well recognized target for novel immunosuppressants. The ShK peptide blocks the T-lymphocyte channel, Kv1.3, ($K_d$=11±1.4 pM; n=4; mean±SEM), inhibits $^{125}$I-ChTX binding to Kv1.3 ($IC_{50}$=pM) and suppresses anti-CD3 stimulated $^3$H-thymidine incorporation by human peripheral blood T-cells with a parallel potency. To determine the selectivity of this peptide for Kv1.3, the inventors tested it against a panel of five related cloned K$^+$ channel targets; Kv1.1, Kv1.2 and Kv1.5 were chosen because they are closely related to Kv1.3, while Kv3.1 and hKCa4 were studied because these channels are expressed in T-cells. ShK peptide blocks Kv1.1 ($K_d$=16±3.5 pM, n=3) with almost the same potency as Kv1.3, while Kv1.2 ($K_d$=9±0.3 nM, n=3) and hKCa4 ($K_d$=28±3.3 nM, n=3) are 100-fold less sensitive. Two other channels, Kv1.5 and Kv3.1, are resistant to block by ShK ($K_d$>1 μM). Collectively, these data indicate that ShK, a potent blocker of the Kv1.3 channel and a powerful immunosuppressant, is non-selective, necessitating a search for a more specific antagonist.

5.13.2.2 Identifying Peptide-Channel Interactions In The External Vestibule

To rationalize the search for a Kv1.3-specific ShK analog, the inventors initiated a study to determine the docking configuration of the peptide in the Kv1.3 external vestibule. The inventors were especially interested in identifying ShK residues that interacted with H404 that lies at the outer entrance to the Kv1.3 pore (Aiyar 1995, 1996; Nguyen 1996). This residue is unique to Kv1.3, the corresponding residues in related channels being: Kv1.1 (Y), Kv1.2 (V), Kv1.4 (K), Kv1.5 (R), Kv3.1(Y), hKCa4 (V). ShK analogs that target H404 might therefore be expected to selectively and potently block Kv1.3 and be less effective on the related channels.

Exploiting double-mutant cycle analysis (Hidalgo and MacKinon, 1995), and guided by the known NMR structure of the peptide and a molecular model of the Kv1.3 channel (Aiyar et al., 1995, 1996), the inventors identified multiple pairs of interacting ShK-Kv1.3 residues. The inventors focused attention on two positively charged ShK residues, R11 and K22, that had been determined by alanine-scanning mutagenesis to be critical for Kv1.3 inhibition; K22, in particular, has been suggested to interact with residues in the channel pore. As a control, the inventors studied another positively charged residue, K9, on the opposite surface of ShK, which is unimportant for binding. Each positively charged residue was individually replaced by neutral (A or Nle) or negative (glutamate) residues. In addition, the inventors substituted positively charged non-natural amino acids, diaminopropionic acid (DAP) and ornithine (Orn) in place of K22; these two mutants (along with K22) were treated as "wild-type" in the mutant cycle analysis and compared against a single mutant peptide containing the neutral residue, Nle22. In all the inventors' studies they have assumed that ShK and its mutants sit in the vestibule with a similar geometry.

5.13.2.3 H404 In Kv1.3 Is Close To The Short Terminal Amines At Position 22 And To R11

Using mutant cycle analysis, the strength of the interaction between H404 and each of the terminal amines at ShK position 22 was estimated. Replacing H404 with the hydrophobic residue valine (H404V) significantly disrupted the interaction of Orn22 with H404, but not that of K22. Based on published criterion, the inventors assume that a coupling energy of $\geq 0.6$ kcal mol$^{-1}$ corresponds to an inter-residue distance of $\leq 5$ Å for a given pair of ShK-Kv1.3 residues. The ΔG values suggest that DAP22 and Orn22 lie within 5 Å of H404, while K22 lies further away.

Similar mutant cycle studies for the peptide-channel pair, Kv1.3 (H404→V)-ShK(R11→A), places R11 within 5 Å of H404. In contrast, K9, the residue on the opposite surface of ShK, does not couple energetically with H404, indicating it is some distance from H404.

5.13.2.4 D402 In KV1.3 Forms An Energetic Contact With Dap22, Orn22 And R11, But Not With K22 Or K9

Aspartate 402 is part of the critical signature sequence (GYGD) present in all Kv channels. Earlier mapping studies with kaliotoxin, places the carboxyl group of D402 in the same horizontal plane as H404, close to the external vestibule (Aiyar et al., 1996). Since mutations at this position result in non-functional channels, the inventors used a dimeric construct containing one wild-type and one mutant (D402N) subunit; the biophysical properties of this dimeric channel have been previously described (Aiyar et al., 1996). The ΔΔG values indicate that the terminal amine of DAP22, Orn22 and R11 are in the vicinity of D402, while K22 and K9 are some distance away.

5.13.2.5 Y400 In Kv1.3 Is Close To Orn22 And K22, But Not To Dap22, R11 Or K9

Tyrosine 400 is highly conserved in all potassium channels and forms part of the ion selectivity filter. This channel residue interacts with the essential K27 in scorpion toxins in a K$^+$ ion dependent manner. In order to determine the coupling energy between the ShK residues and Y400, the inventors used a dimeric construct containing one wild-type subunit and a second Y400V domain (Aiyar et al., 1996). Mutant cycle analysis demonstrate that Y400 couples strongly with the terminal amines in Orn22 and K22 and weakly with R11. The ΔΔG values show that DAP22 and K9 are not in close proximity to Y400.

5.13.2.6 D386 Couples With R11 But Not With K22

The channel residue D386 lies ~7–10 Å from H404 and ~14 Å from the center of the pore (Aiyar et al., 1995, 1996). If D386 is close to a positively charged ShK residue, the introduction of lysine at this position (D386K) should cause a significant reduction in peptide potency via electrostatic repulsion. In keeping with this notion, the D386K mutant was ~60-fold less sensitive to the ShK peptide compared to wild-type Kv1.3 (Table 1). To determine whether R11 or K22 was the positively charged ShK residue in the vicinity of residue 386, the inventors performed mutant cycle analysis: Kv1.3(D386→K)-ShK(R11→A); Kv1.3(D386→K)-ShK(K22→Nle). The ΔΔG values for these cycles suggest that D386 is close to R11 (1.4 kcal.mol$^{-1}$), but not to K22 (0.053 kcal.mol$^{-1}$).

5.13.2.7 Docking Shk In The External Vestibule Of KV1.3

Data suggests that K22 protrudes into the pore and interacts with Y400, like the critical K27 residue in scorpion toxins. Since R11 couples strongly with D386, D402 and H404, but not Y400, the inventors place it in the triangle lying in the base of the vestibule, bounded by the three interacting channel residues (386, 402, 404). Since the α-carbon of R11 is ~11 Å from the α-carbon of K22, the center of this triangle must lie at this distance from the center of the pore. This distance estimate corroborates earlier mapping results obtained with the structurally-defined scorpion toxin, kaliotoxin. K9, the ShK residue on the surface opposite R11 and K22, does not appear to interact with the base of the vestibule.

The placement of R11 and K22 relative to the channel, imposes substantial constraints on possible docking configurations of the toxin in the external vestibule. The inventors have docked ShK in the Kv1.3 vestibule, for heuristic purposes, by guiding K22 into the pore, and rotating the toxin around this axis to bring R11 in the triangle bounded by D386, D402 and H404.

5.13.2.8 Shk-K22Dap: A Selective Kv1.3 Antagonist, Inhibits T-Cell Activation H404 is unique to Kv1.3, and ShK-mutants that selectively target this residue might be specific for Kv1.3. ShK-K22DAP couples strongly with H404, but not with D386 or Y400, and only shows weak interactions with D402. The inventors therefore screened ShK-K22DAP against the panel of K$^+$ channels. As shown in Table 16, ShK-K22DAP is a specific and potent blocker of Kv1.3. It blocks Kv1.3 at low picomolar concentrations, but is 40 fold less potent on Kv1.1, while the other four channels are >100-fold less effective.

5.13.2.9 T-Cell Activation

In order for the ShK-K22DAP to be used as an injectable inimunosuppressant, it has to be stable in-vivo and have a sufficiently long biological half-life. As administration of the peptide would be via an intravenous route, the half-life of the toxin would be expected to be relative to its stability to proteolytic degradation via plasma derived proteases. Many of the proteases present in the plasma are serine proteases with a specificity for basic amino acids. ShK-Dap22 contains nine basic residues (Arg, Dap, His and Lys) and three aromatic residues (Phe and Tyr). To test the stability of ShK Dap22, the inventors elected to use the well characterized serine proteases, trypsin and chymotrypsin, which have a specificity for basic and aromatic residues, respectively. The pH of the digestion studies was kept at 6.5 in order to minimize disulfide shuffling. The K22DAP analog was stable to the treatment with chymotrypsin over the duration of the studies (1 h), however, trypsin, and the combination of trypsin and chymotrypsin, rapidly degraded the peptide with a $t_{1/2}$ of 30 min. These results suggest that additional modifications need to be made to enhance peptide stability in order for it be used clinically.

5.13.2.10 Structure Of Shk-K22Dap

ShK-K22DAP contains a methionine at position 21. Loss of activity in such peptides is sometimes attributed to the oxidation of the Met to the sulfoxide or sulfone by-product. In the case of ShK-Dap22, the inventors observed that the peptide was very susceptible to this oxidation phenomenon, resulting in reduction in potency. As the sole Met residue in ShK toxin lies on the binding face of the toxin (Pennington et al., 1996a), introduction of a more polar substituent at this position appears to be deleterious to toxin activity. In previous reports, substitution of Met with either Nle or Ala was found to slightly increase potency (Pennington et al., 1996 a,b).

5.14 EXAMPLE 14—The Effect of Truncation on Shk Toxin

5.14.1 Materials and Methods

Fmoc-derivatized amino acid derivatives and Fmoc-Cys (Trt)-resin were obtained from Bachera Feinchemikalien (CH-44 I6 Bubendorf, Switzerland). ShK toxin and dendrotoxin from *Dendroaspis polylepis* were prepared as previously described (Pennington et al., 1995; Byrnes et al., 1995).

Peptide Synthesis: Kg-Cys12 (Acm)-Cys(Trt)-Nle21-Cys28(Acm)-Cys32(Trt)-2-chlorotrityl-resin was synthesized using standard Fmoc-methods )n an ABI 431A synthesizer (Atherton and Sheppard, 1989). Each amino acid coupling was mediated by dicyclohexylcarbodiimide in the presence of 2 equivalents of 1-hydroxybenzotriazole. The peptide was cleaved from the resin and simultaneously deprotected using reagent K (King et al., 1990). The disulfide linkage between Cys17 and Cys32 was formed by dissolving the peptide in 0.2 M NH$_4$OAc, pH 8.0 and stirring for 16 h in the presence of air. Following oxidation of the first disulfide bond, the product was purified by preparative RP-HPLC on a Rainin Dynamax ODS column using an aqueous acetonitrile gradient. The pure fractions were pooled together and lyophilized, yielding 310 mg of monocyclic Cys17—Cys32 product. The second disulfide bond was formed by dissolving 200 mg of the monocyclic product in 200 ml of 80% AcOH in H$_2$O and titrating with 30 equivalents 12 for 30 min. The residual I$_2$ was quenched by adding solid ascorbic acid. The sample was diluted with H$_2$O and loaded onto the same RP-HPLC system and purified yielding 105 mg of the bicyclic Cys12—Cys28, Cys17—Cys32 product. ESI-mass analysis was consistent for formation of the monocyclic and bicyclic products.

Biological activity was determined using the $^{125}$-dendrotoxin displacement assay as previously described (Pennington et al., 1995). Circular dichroism spectra were collected as previously described (Kern et al., 1996).

5.14.2 Results And Discussion

The unique structure of ShK links the N and C-terminal regions of the peptide together. This disulfide bond appears to stabilize the structure of the toxin. The region which constitutes the pharmacophore of the toxin occurs primarily in the region of the molecule stabilized by the Cys12—Cys28, Cys17—Cys32 disulfide bonds. By truncating the molecule at the both termini, the Cys3—Cys35 disulfide bond may be eliminated, without deleting any of the residues present in the pharmacophore surface. In the two peptide analogs which the inventors prepared, the inventors have eliminated the N-terminal extended sequence including residues 1–8 and the three C-terminal residues 33–35. The effective length of the toxin has been reduced to a size similar to the endothelin/sarafotoxins. These potent vasoconstrictor peptides are 21 residue bicyclic structures with a stable helical secondary structure (Suadek et al., 1989; Kloog et al., 1988).

Synthesis of peptides with C-terminal Cys residues are hampered by a propensity to racemize at the Cys during resin loading (Atherton et al., 1975) and base catalyzed peptide bond formation (Kaiser et al., 1996). Use of 2-chlorotrityl]-based resins have been shown to help suppress this side reaction (Barlos et al., 1991). Thus, synthesis of the peptides was carried out on a 2-chlorotrityl resin. The oxidation of both monocyclic and bicyclic products went smoothly to the desired product. Yields were excellent, suggesting that the peptides folded very rapidly, like the full length toxin.

The wild type toxin has a CD spectrum indicative of a protein with approximately 30% α-helix (Kem et al., 1996). This result has been confirmed in the solution structure of ShK where the main structural component is a helix-kink-helix from residues 14–24 (Tudor et al., 1996). As shown in FIG. 22, the CD spectrum of the bicyclic analog has a slightly displaced minimum at 205 nm and a small shoulder near 226 nm. The monocyclic analog has a CD spectrum indicative of a peptide with a random coil conformation. The analog CD spectra did not resemble the wild type toxin spectrum.

The biological activity of both peptide analogs was significantly reduced relative to the wild type toxin. The $IC_{50}$ ratio ($IC_{50}$analog/$IC_{50}$ ShK) was 1360 and >3000 for the bicyclic and monocyclic, respectively. The bicyclic analog was slightly more potent than the monocyclic product, possibly as a result of the small amount of helical structure.

In conclusion, it appears that the disulfide bond which links the N and C termini in these toxin analogs is important for locking the toxin into the biologically active form. Although this disulfide bond and adjacent region do not contribute to the pharmacophore, they apparently play a critical role in structure maintenance. It may be possible to remove one of the other internal disulfide bonds. Replacement of a disulfide with two conservative Abu residues as has been recently reported for leiurotoxin (Sabatier et al., 1996). The bicyclic analog with the overlapping disulfide bonds was equipotent to the wild-type leiurotoxin.

5.15 EXAMPLE 15—Additional Shk Mutants

The inventors have also constructed the following mutant forms of ShK: ShK 106 K-14-Asp-Lactam Bridge; ShK 108 Ile-7Cys, C12 Abu; ShK110 Abu 121-Abu28, Ala21; ShK111 Abu17-Abu32, Ala21; ShKI12 Abu3-Abu35, Ala21.

5.16 EXAMPLE 16—Selectivity of ShK-K22 and its Mutants

Cell lines stably expressing Kv1.1–Kv1.3, Kv1.5, Kv3.1 have previously been described (Grissmer et al., 1994). These cell lines were studied electrophysiologically and each cloned channel tested for its sensitivity to ShK. Studies were carried out in the whole-cell configuration of the patch clamp technique. All membrane currents were recorded at room temperature with a LIST EPC-7 patch-clamp amplifier, with 80% series resistance if the current exceeded 2 nA. Capacitative currents were removed by analog subtraction and leak currents were subtracted using P/8 procedure. The command input of the patch-clamp amplifier was controlled by a PDP 11/73 computer via a digital-to-analog converter. The holding potential in all studies was −80 mV. For screening the ShK peptide and its mutants, the voltage was stepped from −80 to 40 mV for 200 ms every 30 sec, before, during and after peptide application.

ShK peptide blocked Kv1.3 channels with a IC50 of 12 pM with a Hill coefficient close to unity. KV1.1, a closely related channel expressed in the brain, heart and skeletal muscle, was equally sensitive to the peptide. Another member of the Kv1-family, Kv1.2, was 100-fold less sensitive to inhibition by ShK, while Kv 1.5 and Kv3.1 were resistant to the peptide.

Obvious concerns regarding ShK toxin's ability to inhibit Kv1.1 with almost the same potency as Kv1.3 necessitated a search for a more selective antagonist of Kv1.3. Several mutants of the ShK toxin were screened in the hope of identifying one that was both a more selective and potent blocker of Kv1.3. The ShK-K22DAP mutant was discovered through this search. This mutant blocks Kv1.3 with an IC50 of ~30 pM, but is 30-fold less potent on Kv1.1, and significantly less potent on the other channels.

5.17 EXAMPLE 17—Immunosuppressive Activity of Shk and Shk-Kssdap

Peripheral blood human lymphocytes were activated by anti-CD3 antibody by routine methods. Briefly, cells were isolated by Ficoll-Hypaque density sedimentation, and placed in media (RPMI-1640 supplemented with 10% fetal calf serum, 1-glutamine and penicillin/streptomycin). The cells were incubated alone, or with anti-CD3 antibody, or with anti-CD3 antibody plus various concentrations of ShK or SHK-KSSDAP. Following 48 hours of incubation at 37° C. in 5% $CO_2$ atmosphere, cells were pulsed with $^3$H-thymidine for 6–16 hours, the cells then harvested, and the thymidine uptake determined.

ShK and ShK K22DAP suppressed T-cell activation with an IC50 of about 1 nM.

5.18 EXAMPLE 18—Treatment of Autoimmune Diseases

The CD18-null PL/J mice provide an excellent system for the study of the efficacy of ShK and ShK derived mutants for the treatment of hyperproliferative skin disorders. A recognized animal model for the assessment of the therapeutic activity of a composition for the treatment of inflammatory skin disease is described by Bullard et al. (1996). The inventors contemplate that this model may be utilized to identify ShK polypeptide compositions useful in the treatment of inflammatory skin diseases. The ShK polypeptide may be administered to CD18-null PL/J mice in a manner similar to the administration of dexamethasone in the Bullard study (Bullard et al., 1996). In preferred embodiments, the ShK polypeptide is administered interperitoneally, intraveneously, of subcutaneously.

CD18-deficient 129/Sv are backcrossed onto the PL/J strain for several generations ($N_4$, $N_7$, and $N_8$). Homozygous mutants are used for analysis. Ten CD18 homozygous mice displaying severe dermatitis and ten non-mutant littermate controls are given daily subcutaneous injections of an effective amount of a compound of the present invention for at least six weeks. A variety of concentrations of the compound may be given to determine the dose effect. The compound then is withdrawn completely or the concentration is lowered over a period of several weeks. Improvement and exacerbation of the dermatitis is clinically assessed on a daily basis. Histological and immunological analyses may be performed as described in Bullard et al. (1996). Improvement during the period of administration of the compound followed by exacerbation upon the withdrawal or reduction of the concentration of administered compound is indicative of an effective compound for the treatment of inflammatory skin disease.

Similar to autoimmune diseases, transplantation of organs into a new host causes an immune response against the new organ. Immunosuppressive compounds are routinely given to patients following organ transplantation to decrease the probability of rejection of the newly transplanted organ. Therefore, transplantation model systems in animals also may be employed to test the efficacy of anti-inflammatory or autoimmune compounds, such as the polypeptides of the present invention.

The inventors contemplate that the polypeptides of the present invention may be used as an in immunosuppressant in transplantation procedures. For example, Granger et al. (1995) describe a the determination of the efficacy of rapamycin monotherapy for immunosuppression following kidney transplantation in swine. The procedures of Granger et al. may be repeated using a polypeptide of the present invention in place of rapamycin.

5.19 EXAMPLE 19—Summary of Shk Toxin Derivatives with Natural Amino-Acid Substitutions

```
RSCIDTIPKSRCTAFQCKHSMKYRLSFCRKTCGTC                (SEQ ID NO:1)

SCIDTIPKSRCTAFQCK(N-acetylhistidine)               (SEQ ID NO:2)
SMKYRLSFCRKTCGTC

CIDTIPKSRCTAFQCKHSMKYRLSFCRKTCGTC                  (SEQ ID NO:3)

RSCIDTIPKSECTAFQCKhisNαAc                          (SEQ ID NO:4)
SMKYRLSFCRKTCGTC

RSCIDTIPKSRCTAFECKHSMKYRLSFCRKTCGTC                (SEQ ID NO:5)

RSCIDTIPKSRCTAFQCKKSMKYRLSFCRKTCGTC                (SEQ ID NO:6)

RSCIDTIPKSRCTAFQCKHSMEYRLSFCRKTCGTC                (SEQ ID NO:7)

RSCIDTIPKSRCTAFQCKHSM(cyclohexylala)               (SEQ ID NO:8)
YRLSFCRKTCGTC

RSCIDTIPKSRCTAFQCKHSMKYRLS(cyclohexylala)          (SEQ ID NO:9)
CRKTCGTC

RSCADTIPKSRCTAAQCKHSMKYRLSFCRKRCGTC                (SEQ ID NO:10)

RSCIDSTIPKSRCTAAQKHSMKYRASFCRKTCGTC                (SEQ ID NO:11)

RSCADTIPKSRCTAAQCKHSMKYRASFCRKTCGTC                (SEQ ID NO:12)

SSCIDTIPKSRCTAFQCKHSMKYRLSFCRKTCGTC                (SEQ ID NO:13)

RSCIDTIPQSRCTAFQCKHSMKYRLSFCRKTCGTC                (SEQ ID NO:14)

RSCIDTIPKSQCTAFQCKHSMKYRLSFCRKTCGTC                (SEQ ID NO:15)

RSCIDTIPKSRCTAAQCKHSMKYRLSFCRKTCGTC                (SEQ ID NO:16)

RSCIDTIPKSRCTAWQCKHSMKYRLSFCRKTCGTC                (SEQ ID NO:17)

RSCIDTIPKSRCTAFQCAHSMKYRLSFCRKTCGTC                (SEQ ID NO:18)

RSCIDTIPKSRCTAFQCKHS(norleu)KYRLSFCRKTCGTC         (SEQ ID NO:19)

RSCIDTOPKSRCTAFQCKHSMAYRLSFCRKTCGTC                (SEQ ID NO:20)

RSCIDTIPKSRCTAFQCKHSM(norleu)YRLSFCRKTCGTC         (SEQ ID NO:21)

RSCIDTIPKSRCTAFQCKHSM(orn)YRLSFCRKTCGTC            (SEQ ID NO:22)

RSCIDTIPKSRCTAFQCKHSM(homocit)                     (SEQ ID NO:23)
YRLSFCRKTCGTC

RSCIDTIPKSRCTAFQCRHSMRYRLSFCRKTCGTC                (SEQ ID NO:24)

RSCIDTIPKSRCTAFQCKHSMKFRLSFCRKTCGTC                (SEQ ID NO:25)

RSCIDTIPKSRCTAFQCKHSMK(nitrophe)                   (SEQ ID NO:26)
RLSFCRKTCGTC

RSCIDTIPKSRCTAFQCKHSMK(aminopheala)                (SEQ ID NO:27)
RLSFCRKTCGTC
```

-continued

| | |
|---|---|
| RSCIDTIPKSRCTAFQCKHSMKYALSFCRKTCGTC | (SEQ ID NO:28) |
| ASCIDTIPKSRCTAFQCKHSMKYRLSFCRKTCGTC | (SEQ ID NO:29) |
| RACIDTIPKSRCTAFQCKHSMKYRLSFCRKTCGTC | (SEQ ID NO:30) |
| RSCADTIOKSRCTAFQCKHSMKYRLSFCRKTCGTC | (SEQ ID NO:31) |
| RSCIATIPKSRCTAFQCKHSMKYRLSFCRKTCGTC | (SEQ ID NO:32) |
| RSCIDAIPKSRCTAFQCKHSMKYRLSFCRKTCGTC | (SEQ ID NO:33) |
| RSCIDTAPKSRCTAFQCKHSMKYRLSFCRKTCGTC | (SEQ ID NO:34) |
| RSCIDTIAKSRCTAFQCKHSMKYRLSFCRKTCGTC | (SEQ ID NO:35) |
| RSCIDTIPASRCTAFQCKHSMKYRLSFCRKTCGTC | (SEQ ID NO:36) |
| RSCIDTIPKARCTAFQCKHSMKYRLSFCRKTCGTC | (SEQ ID NO:37) |
| RSCIDTIPKSACTAFQCKHSMKYRLSFCRKTCGTC | (SEQ ID NO:38) |
| RSCIDTIPKSRCAAFQCKHSMKYRLSFCRKTCGTC | (SEQ ID NO:39) |
| RSCIDTIPKSRCTAAQCKHSMKYRLSFCRKTCGTC | (SEQ ID NO:40) |
| RSCIDTIPKSRCTAFACKHSMKYRLSFCRKTCGTC | (SEQ ID NO:41) |
| RSCIDTIPKSRCTAFQCAHSMKYRLSFCRKTCGTC | (SEQ ID NO:42) |
| RSCIDTIPKSRCTAFQCKASMKYRLSFCRKTCGTC | (SEQ ID NO:43) |
| RSCIDTIPKSRCTAFQCKHAMKYRLSFCRKTCGTC | (SEQ ID NO:44) |
| RSCIDTIPKSRCTAFQCKHSAKYRLSFCRKTCGTC | (SEQ ID NO:45) |
| RSCIDTIPKSRCTAFQCKHSMAYRLSFCRKTCGTC | (SEQ ID NO:46) |
| RSCIDTIPKSRCTAFQCKHSMKARLSFCRKTCGTC | (SEQ ID NO:47) |
| RSCIDTIPKSRCTAFQCKHSMKYALSFCRKTCGTC | (SEQ ID NO:48) |
| RSCIDTIPKSRCTAFQCKHSMKYRASFCRKTCGTC | (SEQ ID NO:49) |
| RSCIDTIPKSRCTAFQCKHSMKYRLAFCRKTCGTC | (SEQ ID NO:50) |
| RSCIDTIPKSRCTAFQCKHSMKYRLSACRKTCGTC | (SEQ ID NO:51) |
| RSCIDTIPKSRCTAFQCKHSMKYRLSFCAKTCGTC | (SEQ ID NO:52) |
| RSCIDTIPKSRCTAPQCKHSMKYRLSFCRATCGTC | (SEQ ID NO:53) |
| RSCIDTIPKSRCTAPQCKHSMKYRLSFCRKACGTC | (SEQ ID NO:54) |
| RSCIDTIPKSRCTAPQCKHSMKYRLSFCRKTCGAC | (SEQ ID NO:55) |
| RSCIDTIPKSRCTAFQCKHSM(diaminopropionic)<br>YRLSFCRKTCGTC | (SEQ ID NO:56) |
| RSCIDTIPKSRCTAFQCKHSMK(benzoylpheala)<br>RLSFCRKTCGTC | (SEQ ID NO:57) |
| (N-acetylarg)SCIDTIPKSRCTAFQC<br>KHSMKYRLSFCRKTCGTC | (SEQ ID NO:58) |
| RSCIDTIPKSRCTA(azidopheala)Q<br>CKHSMKYRLSFCRKTCGTC<br>          S---S | (SEQ ID NO:59) |
| RSCIDTIPKSRCTAFQCKHSMKYRLSFCRKTCGTC<br>   S---S | (SEQ ID NO:60) |
| RSCIDTIPKSRCTAFQCKHSMKYRLSFCRKTCGTC<br>      S---S | (SEQ ID NO:61) |

6.0 References

The following references, to the extent that they provide exemplary procedural or other details supplementary to those set forth herein, are specifically incorporated herein by reference.

U.S. Pat. No. 4,196,265, issued Apr. 1, 1980.
U.S. Pat. No. 4,554,101, issued Nov. 19, 1985.
U.S. Pat. No. 4,683,195, issued Jul. 28, 1987.
U.S. Pat. No. 4,683,202, issued, Jul. 28, 1987.
U.S. Pat. No. 4,757,011, issued Jul. 12, 1988.
U.S. Pat. No. 4,769,061, issued Sep. 6, 1988.
U.S. Pat. No. 4,940,835, issued Jul. 10, 1990.
U.S. Pat. No. 4,965,188, issued Oct. 23, 1990.
U.S. Pat. No. 4,971,908, issued Nov. 20, 1990.
U.S. Pat. No. 5,176,995, issued Jan. 5, 1993.

Aiyar, Withka, Rizzi, Singleton, Andrews, Lin, Boyd, Hanson, Simon, Dethlefs, Lee, Hall, Gutman, Chandy, *Neuron*, 15:1169–1181, 1995.

Allen and Choun, "Large Unilamellar Liposomes with Low Uptake into the Reticuloendothelial System," *FEBS Lett.,* 223:42–46,1987.

Alvord et al., *Ann. Neurol.,* 6:467–473, 1979.

Alvord et al., *Prog. Clin. Biol. Res.,* 146:1–554, 1984.

Aneiros, Garcia, Martinez, Harvey, Anderson, Marshall, Engstrom, Hellman, Karlsson, *Biochim. Biophys. Acta,* 1157:86–92, 1993.

Atherton and Sheppard, In: *Solid Phase Peptide Synthesis,* IRL Press, Oxford University Press, New York, 1989.

Atherton, Clive, Sheppard, *J. Am. Chem Soc.,* 97:6584–6591, 1975.

Auguste et al. "Leiurotoxin I (scyllatoxin), a peptide ligand for Ca2(+)-activated K+ channels. Chemical synthesis, radiolabeling, and receptor characterization," *J. Biol. Chem.,* 265(8):4753–4759, 1990.

Aumelas, Chiche, Mahe, Le-Nguyen, Sizun, Ne, Berthault, Perly, "$^1$H NMR structures of endothelin family peptides," In: *Peptides* 1990 *Proceedings of the Twenty-first European Peptide Symposium,* Giralt and Andreu, eds., Escom, Leiden, Netherlands, pp. 553–554, 1991.

Ball and Alewood, "Conformational constraints: nonpeptides β-turn mimetics," *J. Mol. Recog.,* 3:55–64, 1990.

Barany and Merrifield, "Solid-Phase Peptide Synthesis," In: *The Peptides: Analysis, Synthesis, Biology,* Gross and Meinhofer, eds., Academic Press, New York, pp. 3–284, 1980.

Barlos, Chatzi, Gatos, Stavropoulso, *Int. J Peptide Protein Res.,* 37:513–520, 1991.

Bednarek, Bugianesi, Leonard, Felix, "Chemical synthesis and structure-function studies of margatoxin, a potent inhibitor of voltage-dependent potassium channel in human T lymphocytes," *Biochem. Biophys. Res. Comm.,* 198:619–625, 1994.

Benedetti et al., *Transplantation,* 63:1206–1209, 1997.

Bernstein et al., *J. Mol. Biol.,* 233:123–138, 1977.

Bischoff, Cordier, Rasmussen, Schlesinger, Gachet, Jaquinod, Tripet, Chong, Pavirani, "Synthesis and characterization of photoactivable peptide agonists of the human thrombin receptor," *FEBS Lett.,* 349:301–306, 1994.

Bontems, Gilquin, Roumestand, Menez, Toma, "Analysis of side-chain organization on a refined model of charybdotoxin: structural and functional implication," *Biochem.,* 31:7756–7764, 1992.

Boyd, White, Cerpa, Kaiser, Leeman, "Photoaffinity labeling the substance P receptor using a derivative of substance P containing p-benzoylphenylalanine," *Biochemistry,* 30:336–342, 1991.

Bracken, Gulyas, Taylor, Baum, "Synthesis and nuclear magnetic resonance structure of an α-helical, bicyclic, lactam-bridged hexapeptide," *Journal of the American Chemical Society,* 116:6431–6432, 1994.

Bradford, *Anal. Biochem.,* 72:248–254, 1976.

Bullard et al., *Proc. Natl. Acad. Sci. USA,* 93:2116–2121, 1996.

Byrnes, Mahnir, Kern, Pennington, *Protein Peptide Lett.,* 1:239–245, 1995.

Cahalan, Chandy, Grissmer, "Potassium channels in development, activation, and disease in T-lymphocytes," *Curr. Topics in Membranes* 39:357–394, 1991.

Camisa et al., *Psoriasis,* Blackwell Scientific, Boston, 1994.

Campbell, "Monoclonal Antibody Technology, Laboratory Techniques in Biochemistry and Molecular Biology," Vol. 13, Burden and Von Knippenberg, Eds. pp. 75–83, Elsevier, Amsterdam, 1984.

Castaneda, Sotolongo, Amor, Stocklin, Anderson, Harvey, Engstrom, Wernstedt, Karlsson, *Toxicon,* 33:606–613, 1995.

Catteral W. A., "Pharmacologic properties of voltage-sensitive sodium channels in chick muscle fibers developing in vitro," *Dev. Biol.,* 78(1):222–230, 1980.

Catterall, "Structure and function of voltage-gated ion channels," *TINS,* 16:500–506, 1993.

Catterall, *Ann. Rev. Biochem.,* 64:493–531, 1995.

Chandy and Gutman, "Voltage-gated potassium channel genes," Ch. 1 In: *CRC Handbook of Receptors and Channels,* CRC Press, Boca Raton, Fla., pp. 1–71, 1995.

Chandy et al., "Autologous mixed lymphocyte reaction in man: XV. Cellular and molecular basis of deficient autologous mixed lymphocyte response in insulin-dependent diabetes mellitus," *J. Clin. Immunol.,* 4(6):424–428, 1984.

Chandy, Aiyar, Rizzi, Withka, Lee, Singleton, Andrews Nguyen, Simon, Dethlefs, Hanson, Cahalan, Gutman, "Ion channels in T-cells: Targets for novel immunosuppressants," K-channel I.B.C. Conference, 1995.

Chen, Chrusciel, Nakanishi, Raktabutr, Johnson, Sato, Weiner, Hoxie, Saragovi, Greene, Kahn, "Design and synthesis of a CD4 β-turn mimetic that inhibits human immunodeficiency virus envelope glycoprotein gp120 and infection of human lymphocytes," *Proc. Natl. Acad. Sci. USA,* 89:5872–5876, 1992.

Chesnut, Carpenter, Strichartz, "Effects of venom from *Conus striatus* on the delayed rectifier potassium current of molluscan neurons," *Toxicon,* 25:267–278, 1987.

Chorev, Epand, Rosenblatt, Caulfield, Epand, *Int. J. Peptide Protein Res.,* 42:342–350, 1993.

Chou and Fasman, "Conformational Parameters for Amino Acids in Helical, β-Sheet, and Random Coil Regions Calculated from Proteins," *Biochemistry,* 13(2):211–222, 1974b.

Chou and Fasman, "Empirical predictions of protein conformation," *Adv. Enzymol.,* 47:251:276, 1978.

Chou and Fasman, "Empirical Predictions of Protein Conformation," *Ann. Rev. Biochem.,* 47:251–276,1978b.

Chou and Fasman, "Prediction of β-Turns," *Biophys. J.,* 26:367–384,1979.

Chou and Fasman, "Prediction of Protein Conformation," *Biochemistry,* 13(2):222–245, 1974a.

Clackson and Wells, "A hot spot of binding energy in a hormone-receptor interface," *Science,* 267:383–386, 1995.

Couvreur et al., "Nanocapsules, a New Lysosomotropic Carrier," *FEBS Lett.,* 84:323–326, 1977.

Couvreur, "Polyalkyleyanoacrylates as Colloidal Drug Carriers," *Crit. Rev. Ther. Drug Carrier Syst.*, 5:1–20, 1988.

Crankshaw and Grant, (eds.) *Identification of Modified PTH Amino Acids in Protein Sequencing Analysis*, 1st ed., Association for Biomolecular Resource Facilities, Bethesda, Md., 1993.

Crest, Jacquet, Gola, Zerrouk, Benslimane, Rochat, Mansuelle, Martin-Eauclaire, *J. Biol. Chem.*, 267:1640–1647, 1992.

Dauplais, Lecoq, Song, Cotton, Jamin, Gilquin, Roumestand, Vita, de Medeiros, Rowan, et al., "On the convergent evolution of animal toxins. Conservation of a diad of functional residues in potassium channel-blocking toxins with unrelated structures," *J. Biol. Chem.*, 272:4302–9, 1997.

de Castiglione, Tam, Liu, Zhang, Galantino, Bertolero, Vaghi, "Alanine Scan of Endothelin," In: *Peptides: Chemistry and Biology, Proceedings of the Twelfth American Peptide Symposium*, Escom, Leiden, Netherlands, pp. 402–403, 1992.

Deutsch, Price, Lee, King, Garcia, "Characterization of high affinity sites for charybdotoxin in human T lymphocytes," *J. Biol. Chem.*, 266:3668–3674, 1991.

Ellman, *Arch. Biochem. Biophys.*, 82:70, 1959.

Escobar, Root, MacKinnon, "Influence of protein surface charge on the bimolecular kinetics of a potassium channel peptide inhibitor," *Biochem.*, 32:6982–6987, 1993.

Felix, Heimer, Wang, Lambros, Fournier, Mowles, Maines, Campbell, Wegrzynski, Toome, Fry, Madison, "Synthesis, biological activity and conformational analysis of cyclic GRF analogs," *Int. J. Pept. Prot. Res.*, 32:441–454, 1988.

Felix, Wang, Heimer, Fournier, "Applications of BOP reagent in solid phase synthesis. II. Solid phase side chain to side chain cyclizations using BOP reagent," *Int. J. Peptide Protein Res.*, 31:231–238, 1988.

Fernandez et al., *Biochemistry*, 33:14256–14263, 1994.

Fogh, Kem, Norton, "Solution structure of neurotoxin I from the sea anemone *Stichodactyla helianthus*. A nuclear magnetic resonance, distance geometry and restrained molecular dynamics study," *J. Biol. Chem.*, 265:13016–13028, 1990.

Gabizon and Papahadjopoulos, "Liposomes formulations with prolonged circulation time in blood and enhanced uptake by tumors," *Proc. Natl. Acad. Sci. USA*, 85:6949–6953, 1988.

Galantino, de Castiglione, Tam, Liu, Zhang, Cristiani, Vaghi, "D-Amino acid scan of endothelin," In: *Peptides Chemistry and Biology Proceedings of the Twelfth American Peptide Symposium*, Smith and Rivier, eds., Escom, Leiden, Netherlands, pp. 404–405, 1992.

Galvez, Gimenez-Gallego, Rueben, Roy-Contancin, Feigenbaum, Kaczorowski, Garcia, *J. Biol. Chem.*, 265:11083–10090, 1990.

Garcia, Galvez, Garcia-Calvo, King, Vasquez, Kaczorowski, "Use of toxins to study potassium channels," *J. Bioen. Biomemb.*, 23:615–646, 1991.

Garcia, Garcia-Calvo, Hildalgo, Lee, MacKinnon, "Purification and characterization of three inhibitors of voltage-dependent K+ channels from *Leiurus quinquestriatus* var. *hebraeus* venom," *Biochem.*, 33:6834–6839, 1994.

Garcia-Calvo, Leonard, Novick, Stevens, Schmalhofer, Kaczorowski, Garcia, *J. Biol. Chem.*, xx:18866–18874, 1993.

Garsky, Lumma, Freidinger, Pitzenberger, Randall, Veber, Gould, Freidman, "Chemical synthesis of echistatin, a potent inhibitor of platelet aggregation from *Echis carinatus*: synthesis and biological activity of selected analogs," *Proc. Natl. Acad. Sci. USA*, 86:4022–4026, 1989.

Gefter et al., *Somat. Cell Genet.*, 3:231–236, 1977.

Giangiacomo, Sugg, Garcia-Calvo, Leonard, McManus, Kaczorowski, Garcia, "Synthetic charybdotoxin-iberiotoxin chimeric peptides define toxin binding sites on calcium-activated and voltage-dependent potassium channels," *Biochem.*, 32, 2363–2370, 1993.

Gilson et al., "On the calculation of electrostatic interactions in proteins," *J. Mol. Biol.*, 184(3):503–516, 1985.

Goding, "Monoclonal Antibodies: Principles and Practice," pp. 60–74. 2nd Edition, Academic Press, Orlando, Fla., 1986.

Goldstein, Pheasant, Miller, "The charybdotoxin receptor of a Shaker K+ channel: peptide and channel residues mediating molecular recognition" *Neuron*, 12:1377–1388, 1994.

Gorka, McCourt, Schwartz, "Automated synthesis of C-terminal photoprobe using combined Fmoc and t-Boc synthesis strategies on a single automated peptide synthesizer," *Peptide Res.*, 2:376–380, 1989.

Granger et al., *Transplantation*, 59:183–186, 1995.

Grissmer, Nguyen, Aiar, Hanson, Mather, Gutman, Karmilowics. Auperin, Chandy, "Pharmacological characterization of five cloned voltage-gated Kv channels, types Kv 1.1, 1.2, 1.3, 1.5, and 3.1, stably expressed in mammalian cell lines." *Mol. Pharmacol.*, 45:1227–1234, 1994.

Guy and Durell, "Using sequence homology to analyze the structure and function of voltage-gated ion channel proteins," In: *Molecular Evolution of Physiological Processes*, Fambrough, ed., Rockefeller Univ. Press, New York, pp. 197–212, 1994.

Haniu, Acklin, Kenney, Rhode, *Int. J. Pept. Protein Res.*, 43:81, 1994.

Harvey and Anderson, In: *Snake Toxins*, Harvey, A. L. (ed.), Pergamon Press, New York, N.Y., pp. 425–447, 1991.

Harvey, *Med. Res. Rev.*, 13:81–104, 1993.

Heath, Tam, Merrifield, "Improved deprotection of cysteine-containing peptides in HF," *Int. J. Peptide Protein Res.*, 28:498–507, 1986.

Henry-Michelland et al., "Attachment of Antibiotics to Nanoparticles; Preparation, Drug-Release and Antimicrobial Activity in vitro," *Int. J. Pharm.*, 35:121–127,1987.

Hidalgo and MacKinnon, "Revealing the architecture of a K+ channel pore through mutant cycles with a peptide inhibitor," *Science*, 268:307–310, 1995.

Hill, Grant, Volberg, Rapp, Faltynek, Miller, Pagani, Biazman, Wang, Guiles, Krafte, *Molecular Pharmacol.*, 48:98–104, 1995.

Ho et al., "Site-Directed Mutagenesis by Overlap Extension Using the Polymerase Chain Reaction," *Gene*, 77:51–59, 1989.

Holm and Sander, *J. Mol. Biol.*, 233:123–138, 1993.

Honig and Hubbell, "Stability of "salt bridges" in membrane proteins." *Proc. Natl. Acad. Sci. USA*, 81(17):5412–5416, 1984.

Houston Jr., Gannon, Kay, Hodges, "Lactam bridge stabilization of α-helical peptides: ring size, orientation and positional effects," *Journal of Peptide Science*, 1:274–282, 1995.

Hruby and Bonner, "Design of novel synthetic peptides including cyclic conformationally and topographically constrained analogs," In: *Methods in Molecular Biology, Vol. 35, Peptide Synthesis Protocols*, Pennington and Dunn, eds., Humana Press, Totowa, N.J., pp. 201–240, 1994.

Hunter and Greenwood, *Nature* (London), 194:495–496, 1962.

Hurst, Busch, Kavanaugh, Osborne, North, Adelman, "Identification of amino acid residues involved in dendrotoxin block of rat voltage-dependent potassium channels," *Mol. Pharmacol.,* 40:572–576, 1991.

Hyberts, Goldberg, Havel, Wagner, *Protein Sci.,* 1:736–751, 1992.

Jameson and Wolf, "The Antigenic Index: A Novel Algorithm for Predicting Antigenic Determinants," *Compu. Appl. Biosci.,* 4(1):181–6, 1988.

Jameson and Wolf, *Compu. Appl. Biosci.,* 4(l):181–6,1988.

Jameson, McDonnell, Marini, Korngold, "A rationally designed CD4 analogue inhibits experimental allergic encephalomyelitis," *Nature,* 368:744–746, 1994.

Johnson and Sugg, *Biochemistry,* 31:8151–8159, 1992.

Johnson, Stevens, Williamson, *Biochemistry,* 33:15061–15070, 1994.

Juvvadi, Vunnam, Merrifield, "Synthetic melittin, its enantio, retro, and retroenantio isomers, and selected chimeric analogs: their antibacterial, hemolytic, and lipid bilayer action," *J. Am. Chem. Soc.,* 118:8989–8997, 1996.

Kaczorowski and Koo, *Persp. Drug Disc. Design,* 2:233–241, 1994.

Kahn, "Peptide secondary structure mimetics: recent advances and future challenges," *Synlett,* 821–826, 1993.

Kaiser, Nicholson, Kohlbau, Voelter, *Tet. Lett.,* 37:1187–1190, 1996.

Kaizer and Kezedy, "Secondary structure of proteins and peptides in amphiphilic environments (A Review)," *Proc. Natl. Acad. Sci. USA,* 80:1137–1143, 1983.

Kamber, Hartmann, Eisler, Riniker, Rink, Sieber, Rittel, "The synthesis of cystine peptides by iodine oxidation of S-trityl cysteine and S-acetamidomethyl-cysteine peptides," *Helv. Chim. Acta,* 63:899–915, 1980.

Kanmera, Mori, Minegishi, Nakao, "Conformationally constrained PTH-related protein antagonists," In: *Peptides 1994: Proceedings of the 23rd European Peptide Symposium,* Maia, ed., Escom, Leiden, Netherlands, pp. 650–651, 1995.

Karlsson, Adem, Aneiros, Castaneda, Harvey, Jolkkonen, Sotolongo, *Br. J. Pharmacol,* 104:34P, 1991.

Karlsson, Aneiros, Casteneda, Harvey, In: *Recent Advances in Toxinology Research,* Gopalakrishankone, P. and Tan, C. K. (Eds.), National University of Singapore, Singapore, Vol. 2, pp. 378–391, 1992.

Kauer, Ericksson-Viitanen, Wolfe Jr., DeGrado, "p-Benzoyl-L-phenylalanine, a new photoreactive amino acid," *J. Biol. Chem.,* 261:10695–10700, 1986.

Kavanaugh et al., "Multiple subunits of a voltage-dependent potassium channel contribute to the binding site for tetraethylammonium," *Neuron,* 8(3):493–497, 1992.

Kem, Parten, Pennington, Dunn, Price, "Isolation, characterization and amino acid sequence of a polypeptide neurotoxin occurring in the sea anemone *Stichodactyla helianthus,*" *Biochem.,* 28:3483–3489, 1989.

Kemp, Boyd, Muendel, *Nature,* 352:451–454, 1991.

Kern, Sanyals, Williams, Pennington, *Lett. Peptide Sci.,* 3:69–72, 1996.

Kieber-Emmons, Murali, Greene, "Therapeutic peptides and peptidomimetics," *Curr. Opin. Biotechnol.,* 8:435–441, 1997.

Kim et al., *J. Biol. Chem.,* 269:23876–23878, 1994.

Kim, Takahashi, Ogura, Kohno, Kudo, Sato, In: *Peptides 1994: Proceedings of the 23rd European Peptide Symposium,* (H. L. S. Maia, Ed.), Escom, Leiden, Netherlands, pp. 135–136, 1995.

King, Fields, Fields, "A cleavage method which minimizes side reactions following Fmoc solid phase synthesis," *Int. J. Peptide Protein Res.,* 36:255–266, 1990.

Kirby, Britton, Aubert, Rivier, "Identification of high-potency neuroreptide Y analogues through systematic lactamization," *J. Med. Chem.,* 40:210–215, 1997.

Kloog, Ambar, Sokolovsky, Zkochva, Wollberg, Bdolah, *Science,* 242:268–270, 1988.

Kohler and Milstein, *Eur. J. Immunol.,* 6:511–519, 1976.

Kohler and Milstein, *Nature,* 256:495–497, 1975.

Koo, Blake, Talento, Nguyen, Lin, Sirotina, Shah, Mulvany, Horn, Cunningtham, Wunderler, McManus, Slaughter, Bugianesi, Felix, Cartin, Williamson, Kazozowski, Sigal, Springer, Feeney, *J. Immunol.,* 158:5120–5128, 1997.

Kraulis, *J. Appl. Crystallogr.,* 24:946–950, 1991.

Krezel, Kasibhatla, Hidalgo, MacKinnon, Wagner, *Protein Sci.,* 4:1478–1489, 1995.

Krstenansky, Owen, Yates, Mao, "Desin synthesis and antithrombin activity for conformationally restricted analogs of peptide anticoagulants based on the C-terminal region of the leech peptide, hirudin," *Biochimica Biophysica Acta,* 957:53–59, 1988.

Kuby, J., "Immunology" 2nd Edition. W.H. Freeman & Company, New York, 1994.

Kyte and Doolittle, *J. Mol. Biol.,* 157(1):105–132,1982.

Kyte and Doolittle, *J. Mol. Biol.,* 157:105–132, 1982.

Lavretsky and Jarvik, "A group of potassium-channel blockers-acetylcholine releaseres: new potentials for Alzheimer disease? A review," *J. Clin. Psychopharmacol,* 12(2):110–118, 1992.

Leach et al., *Am. J. Pathol,* 148:1503–1515, 1996.

Lerner, Qian, Blaskovich, Fossum, Vogt, Sun, Cox, Der, Hamilton, Sebti, "Ras CAAX peptidomimetic FTI-277 blocks oncogenic Ras signaling by inducing cytoplasmic accumulation of inactive Ras-Raf complexes," *J. Biol. Chem.,* 270:26802–26806, 1995.

Leonard, Garcia, Slaughter, Reuben, "Selective blockers of voltage-gate K+ channels depolarize human T-lymphocytes: Mechanism of the antiproliferative effect of charybdotoxin," *Proc. Natl. Acad. Sci. USA,* 89:10094–10098, 1992.

Lewis and Cahalan, "Potassium and calcium channels in lymphocytes," *Ann. Rev. Immunol.,* 13:623–653, 1995.

Li et al., "Minimization of a polypeptide hormone," *Science,* 270(5242):1657–1660, 1995.

Lin et al., *J. Exp. Med.,* 177:637–645, 1993.

Lobl, Beibel, Yem, "On-resin biotinylation of chemically synthesized proteins for one-step purification," *Anal. Biochem.,* 170:502–511, 1988.

Loffet and Zhang, "Allyl-based groups for side-chain protection of amino acids," *Int. J. Peptide Protein Res.,* 42:346–351, 1993.

Maloy et al, "Microbial Genetics" 2nd Edition. Jones and Barlett Publishers, Boston, Mass., 1994.

Maloy, S. R., "Experimental Techniques in Bacterial Genetics" Jones and Bartlett Publishers, Boston, Mass., 1990.

Manoleras and Norton, "Three-dimensional structure in solution of neurotoxin III from the sea anemone *Anemonia sulcata,*" *Biochem.,* 33:11051–11061, 1994.

Marshall, Gorin, Moore, "Peptide conformation and biological activity," *Ann. Rev. Med. Chem.,* 13:227–238, 1978.

Massacesi et al., *Ann. Neurol.,* 37:519–530, 1995.

McFarlin et al., *J. Immunol.,* 113:712, 1974.

Meara, Cao, Urban, Nakanishi, Yeung, Kahn, "Design and synthesis of small molecule initiators of a α-helix structure in short peptides in water," In: *Peptides 1994: Proceedings of the 23rd European Peptide Symposium,* Maia, ed., Escom, Leiden, Netherlands, pp. 692–693, 1995.

Meyers, Zafaralla, Gray, Abbott, Cruz, Olivera, "α-Conotoxins, small peptide probes of nicotinic acetyl choline receptors," *Biochem.*, 30:9370–9377, 1991.

Miller, "Diffusion-controlled binding of a peptide neurotoxin to its K+ channel receptor," *Biochem.*, 29:5320–5325, 1991.

Miller, Hadac, Powers, "Preparation of radiolabeled photolabile probes of high specific radioactivity for affinity labeling," *Anal. Biochem.*, 220:434–435, 1994.

Miller, *Science*, 252:1092–1096, 1991.

Moczydlowski, Lucchesi, Ravindran, *J. Membr. Biol.*, 105:95–111, 1988.

Monks, Pallaghy, Scanlon, Norton, Structure, 3:791–803, 1995.

Nakamura et al., "Enzyme Immunoassays: Heterogenous and Homogenous Systems," Chapter 27., 1987.

Nguyen et al., "Novel nonpeptide agents potently block the C-type inactivated conformation of Kv1.3 and suppress T cell activation," *Mol. Pharmacol*, 50(6):1672–1679, 1996.

Niwa et al., "Fibrinogen Mitaka II: a hereditary dysfibrinogen with defective thrombin binding caused by an A alpha Glu-11 to Gly substitution," *Blood*, 82(12):3658–3663, 1993.

Nomizu, Inagaki, Iwamatsu, Kishiwabara, Ohta, Morita, Mishikori, Otaka, Fujii, Roller, "Solid phase peptide synthesis of human endothelin precursor peptides using two hard acid deprotection/cleavage methods," *Int. J. Peptide Protein Res.*, 38:580–587, 1991.

Ohizumi et al., Specific inhibition of [3H] saxitoxin binding to skeletal muscle sodium channels by geographutoxin II, a polypeptide channel blocker," *J. Biol. Chem.*, 261(14):6149–6152, 1986.

Ohnishi et al., "Potent aquaretic agent. A novel nonpeptide selective vasopressin 2 antagonist (OPC-31260) in men," *J. Clin. Invest.*, 92(6):2653–2659, 1993.

Pallaghy, Duggan, Pennington, Norton, "Three-dimensional structure in solution of the calcium channel blocker w-conotoxin," *J. Mol. Biol.*, 234:405–420, 1993.

Pallaghy, Nielsen, Craik, Norton, *Protein Sci.*, 3:1833, 1994.

Pallaghy, Scanlon, Monks, Norton, "Three-dimensional structure in solution of the polypeptide cardiac stimulant anthopleurin-A," *Biochem.*, 34:3782–3794, 1995.

Park and Miller, *Biochemistry*, 31:7749–7755, 1992.

Pennington et al., "An Essential Binding Surface for ShK Toxin Interaction with Rat Brain Potassium Channels," *Biochem.*, 35(51):16407–16411, 1996.

Pennington et al., "Chemical synthesis and characterization of ShK toxin: a potent potassium channel inhibitor from a sea anemone," *Int. J. Peptide Res.*, 46:354–358, 1995.

Pennington et al., "Synthesis of the cardiac inotropic polypeptide anthopleurin-A," *Int. J. Peptide Protein Res.*, 43:463–470, 1990.

Pennington, "Site specific chemical modification procedures," In: *Methods in Molecular Biology; Vol. 35, Peptide Synthesis Protocols*," Pennington and Dunn, eds., Humana Press, Totowa, N.J., pp. 171–185, 1994.

Pennington, Byrnes, Zaydenberg, Khaytin, de Chastonay, Krafte, Hill, Mahnir, Volberg, Gorczyca, Kem, *Int. J. Peptide Protein Res.*, 46:354–358, 1995.

Pennington, Kem, Dunn, "Synthesis and biological activity of six monosubstituted analogs of a sea anemone polypeptide neurotoxin," *Peptide Res.*, 3:228–232, 1990.

Pennington, Mahnir, Baur, MacVaugh, Behm, Kem, *Protein and Peptide Letters*, 4(4):237–242, 1997.

Pennington, Mahnir, Khaytin, Zaydenberg, Byrnes, Kem, *Biochemistry*, 35:16407–16411, 1996b.

Pennington, Mahnir, Krafte, Zaydenberg, Byrnes, Khaytin, Crowley, Kem, *Biochem. Biophys. Res. Comm.*, 219:696–701, 1996a.

Pettinelli et al., *J. Immunol.*, 127:1420–1423, 1985.

Phelan, Skelton, Braisted, McDowell, "A general method for constraining short peptides to an α-helical conformation," *J. Am. Chem. Soc.*, 119:455–460, 1997.

Picus et al., *Transplantation*, 39:297–301, 1985.

Pohl, Hubalek, Byrnes, Nielsen, Woods, Pennington, "Assignment of the three disulfide bonds in ShK toxin: a potent potassium channel inhibitor from the sea anemone *Stichodactyla helianthus*," *Letter in Peptide Sci.*, 1:291–297, 1995.

Pohl, In: *Methods in Molecular Biology, Vol. 36: Peptide Analysis Protocols*, Dunn, B. M. and Pennington, M. W. (eds.), Humana Press, Totowa, N.J., pp. 107–129, 1994.

Powers, Fourmy, Gaisano, Miller, "Intrinsic photoaffinity labeling probes for cholecystokinin (CCK)-Gastrin family receptors," *J. Biol. Chem.*, 263::5295–5300, 1988.

Price, Lee, Deutsch, "Charybdotoxin inhibits proliferation and interleukin 2 production in human peripheral blood lymphocytes," *Proc. Natl. Acad. Sci. USA*, 86:10171–10175, 1989.

Prokop, A., and Bajpai, R. K. "Recombinant DNA Technology I" *Ann. N.Y. Acad Sci.* Vol. 646, 1991.

Raine et al., *Lab. Invest.*, 5:534–546, 1984.

Rist, Zerbe, Ingenhoven, Scapozza, Peers, Vaughan, McDonald, Wieland, Beck-Sickinger, "Modified, cyclic dodecapeptide analog of neuropeptide Y is the smallest full agonist at the human Y2 receptor," *FEBS Lett.*, 94:169–173, 1996.

Rivier and McClintock, *J. Chromatogr.*, 268:112–119, 1983.

Romi, Crest, Gola, Sampieri, Jacquet, Zerrouk, Mansuelle, Sorokirie, Van Dorsselaer, Rochat, Martin-Eauclaire, Van Rietschoten, "Synthesis and characterization of kaliotoxin. Is the 26–32 sequence essential for potassium channel recognition?" *J. Biol. Chem.*, 268:26302–26309, 1993.

Rose, Gierasch, Smith, "Turns in peptides and proteins," *Adv. Protein Chem.*, 37:1–109, 1985.

Sabatier, Lecomte, Mabrouk, Darbon, Oughideni, Canarelli, Rochat, Martin-Eauelaire, Van Rietschoten, *Biochemistry*, 35:10641–10647, 1996.

Salgado and Kem, "Actions of three structurally distinct sea anemone toxins on crustacean and insect sodium channels," *Toxicon*, 30:1365–1381, 1992.

Sambrook, J. et al., "Molecular Cloning: A Laboratory Manual," Cold Spring Harbor Laboratory, Cold Spring Harbor, N.Y., 1989.

Sato, Ishida, Wakamatsu, Kato, Honda, Ohizumi, Nakamura, Ohya, Lanelin, Kohda, Inagaki, "Active site of μ-conotoxin GIIIA, a peptide blocker of muscle sodium channels," *J. Biol. Chem.*, 266:16990–16991, 19xx.

Schmidt et al., *Transplantation Proceedings*, 29:1521, 1997.

Schrohenloher and Bennett, In: *Practical Protein Chemistry—A Handbook*, Darbre, A. (Ed.), Wiley, Chichester, pp. 149–163, 1994.

Schweitz, Bruhn, Guillemare, Moinier, Lancelin, Beress, Lazdunski, *J. Biol. Chem.*, 270:25121–25126, 1995.

Scott, Muniz, Sewing, Lichtinghagen, Parcej, Pongs, Dolly, "Antibodies specific for distinct Kv subunits unveil a hetero-oligomeric basis for subtypes of alphadendrotoxin-sensitive K+ channels in bovine brain," *Biochem.*, 33:1617–1623, 1994.

Seale, Srinivasan Rose, *Protein Sci.* 3:1741–1745, 1994.

Segal, I. H., "Biochemical Calculations" 2nd Edition. John Wiley & Sons, New York, 1976.

Selsted and Harwig, "Determination of the disulfide array in the human defensin HNP-2: a covalently cyclized peptide," *J. Biol. Chem.,* 264:4003–4007. 1989.

Shoelson, Lynch, Chatterjee, Chaudhuri, Feng, "Bpa-insulins: photoactivatable analogs for identifying site-site interactions between insulin and the insulin receptor," In: *peptides Chemistry and Biology: Proceedings of the Twelfth American Peptide Symposium,* Smith and Rivier, eds., Escom, Leiden, Netherlands, pp. 57–58, 1992.

Skarzynski, *J. Mol. Biol.,* 224:671, 1992.

Smith and Pease, "Reverse turns in peptides and proteins," *CRC Crit. Rev. Biochem.,* 8(4):315–399, 1980.

Spinella, Malik, Everitt, Anderson, "Design and synthesis of a specific endothelin 1 antagonist: Effects on pulmonary vasoconstriction," *Proc. Natl. Acad Sci. USA,* 88:7443–7446, 1991.

Stampe, Kolmakova-Partenensky, Miller, "Intimations of K+ channel structure from a complete map of the molecular surface of charybdotoxin," *Biochemistry,* 33:443–450, 1994.

Stocker and Miller, "Electrostatic distance geometry in a K+ channel vestibule," *Proc. Natl. Acad. Sci. USA,* 91:9509–9513, 1994.

Stocker, Pongs, Hoth, Heinemann, Stuhmer, Schroter, Ruppersberg, "Swapping of functional domains in voltage-gated K+ channels," *Proc. Natl. Acad. Sci. USA,* 85:8742–8746, 1991.

Strong, *Pharmac. Ther.,* 46:137–162, 1990.

Suadek, Hoflack, Pelton, *FEBS Lett.,* 257:145–148, 1989.

Sugg, Garcia, Reuben, Patchett, Kaczorowski, *J. Biol. Chem.,* 265:18745–18748, 1990.

Tanabe et al., *J. Urol.,* 152:562–566, 1994.

Tejedor and Catterall, "Site of covalent attachment of α-scorpion toxin derivatives in domain I of the sodium channel a subunit," *Proc. Natl. Acad Sci. USA,* 85:8742–8746, 1988.

Trainer, Baden, Catterall, "Identification of the peptide components; of the brevetoxin receptor site of rat brain sodium channels," *J. Biol. Chem.,* 269:19904–19909, 1994.

Tudor, Pallaghy, Pennington, Norton, *Nature Structural Biology,* 3:317–320, 1996.

Vasquez, Feigenbaum, King, Kaczorowski, Garcia, "Characterization of high affinity binding sites for charybdotoxin in synaptic plasma membranes from rat brain. Evidence for a direct association with an inactivating, voltage-dependent, potassium channel," *J. Biol. Chem.,* 265:15564–15571, 1990.

Veber, Milkowski, Varga, Denkewalter, Hirschmann, "Acetamidoinethyl. A novel protecting group for cysteine," *J. Am. Chem. Soc.,* 94:5456–5461, 1972.

Vita, Bontems, Bouet, Tauc, Poujeol, Vatanpour, Harvey, Menez, Toma, "Synthesis of charybdotoxin and of two N-terminal truncated analogues. Structural and functional characterization," *Eur. J. Biochem.,* 217:157–169, 1993.

Wasserman, "New methods in the formation of cacrocyclic lactanis and lactones of biological interest," *Aldrichim. Acta,* 20:63–74, 1987.

Weiland and Molinoff, "Quantitative analysis of drug-receptor interactions: I. Determination of kinetic and equilibrium properties," *Life Sci.,* 29:313–330, 1981.

Wilcox, Fogh, Norton, "Refinement of the solution structure of the sea anemone neurotoxin ShI," *J. Biol. Chem.,* 268:24707–24719, 1993.

Wilson et al., *J. Immunol.,* 151:1571–1578, 1993.

Wolf et al., "An Integrated Family of Amino Acid Sequence Analysis Programs," *Compu. Appl. Biosci.,* 4(1):187–91, 1988.

Wolf et al., *Compu. Appl. Biosci.,* 4(1):187–91,1988.

Yu and Taylor, "A new strategy applied to the synthesis of an α-helical bicyclic peptide constrained by two overlapping i, i4–7 side-chain bridges of novel design," *Tetrahedron Letters,* 37:1731–1734, 1996.

Zamvil et al., *Nature,* 317:355–358, 1985.

Zhang, Dawe, Jiang, Becket, Naider, "A superactive peptidomimetic analog of a farnesylated dodecapeptide yeast pheromone," *Biochem. Biophys. Res. Comm.,* 224:327–331, 1996.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method of inhibiting Kv1 potassium channel activity in a lymphocyte cell of an animal, comprising providing to said animal an amount of a polypeptide composition effective to inhibit said channel activity in said cell wherein Arg11 of SEQ ID NO:1 is substituted with alanine, glutamine, glutamic acid; or Phe15 is substituted with alanine, tryptophan or p-azidophenalanine; or Lys22 is substituted with alanine, norleucine, ornithine, homocitrulline, arginine, phenylalanine, glutamic acid or diaminopinielic acid; or Tyr23 is substituted with alanine, glutamine, glutamic acid phenylalanine, cyclohexlalanine, p-benzoylphenylalanine, p-nitrophenylalanine or aminophenylalanine; or Leu25 is substituted with alanine.

2. The method of claim 1 wherein said animal is a human.

3. The method of claim 2, wherein said human is diagnosed with an autoimmune disease selected from the group consisting of psoriasis, lupus, Sjogren's syndrome, rheumatoid arthritis, ulcerative colitis, Crohn's disease, and sympathetic ophthalmia.

4. A method of inhibiting Kv1 potassium channel activity in a lymphocyte cell of an animal, comprising providing to said cell an amount of a polypeptide composition effective to inhibit said channel activity in said cell wherein the polypeptide composition comprises the amino acid sequence of any of SEQ ID NO:2 to SEQ ID NO:61.

5. A polypeptide composition comprising a polypeptide having diaminopropionic acid substituted for Lys at amino acid position 22 of SEQ ID NO:1.

6. The polypeptide composition of claim 5 wherein said polypeptide composition is administered to an animal with an immunosuppressive agent.

7. The method of claim 6, wherein said immunosuppressive agent is selected from the group consisting of cyclosporin, rapamycin, azathioprine, prednisone, and deoxyspergualin, or a salt or an analog thereof.

8. A composition comprising a polypeptide that has the amino acid sequence of any of SEQ ID NO:4–SEQ ID NO:61 and an immunosuppressive agent in a pharmaceutically-acceptable excipient.

9. The composition of claim 8, wherein said immunosuppressive agent is a peptidomimetic.

10. The composition of claim 8, wherein said immunosuppressive agent is selected from the group consisting of cyclosporin, rapamycin, azathioprine, prednisone, and deoxyspergualin, or a salt or an analog thereof.

11. A kit comprising, in suitable container means, a polypeptide having the sequence of any of SEQ ID NO:2–61 and a pharmaceutically acceptable excipient.

12. The kit of claim 11, further comprising a single container means.

13. The kit of claim 11, wherein said polypeptide and said excipient are present within distinct container means.

14. The kit of claim 11, wherein said polypeptide is suitable for parenteral, intramuscular, or intravenous administration.

15. The kit of claim 11, wherein said polypeptide is suitable for oral or topical administration.

16. The kit of claim 11, further comprising an immunosuppressive agent.

17. The kit of claim 11, wherein the immunosuppressive agent is a peptidomimetic having immunosuppressive properties.

18. The kit of claim 11 or claim 16 wherein the polypeptide has the amino acid sequence of SEQ ID NO:56.

19. A method of suppressing an immune response in an animal, comprising administering to said animal an amount of a composition comprising a polypeptide having the amino acid sequence of any of SEQ ID NO:2–SEQ ID NO:61 effective to suppress said response in said animal.

20. A polypeptide composition comprising a polypeptide having the amino acid sequence of any of SEQ ID NO:2 to SEQ ID NO:61.

21. A method of treating an autoimmune disease in an animal, said method comprising the steps of:

(a) identifying an animal suspected of having an autoimmune disease; and (b) administering to said animal an amount of the polypeptide composition of claim 20 sufficient to treat said autoimmune disease in said animal.

22. The method of claim 21, further comprising administering to said animal an immunosuppressive composition.

23. The method of claim 21, wherein said autoimmune disease s selected from the group consisting of psoriasis, lupus, Sjogren's syndrome, rheumatoid arthritis, ulcerative colitis, Crohn's disease, and sympathetic ophthalmia.

24. The polypeptide composition of claim 20, wherein said polypeptide inhibits potassium channel activity in a lymphocyte T-cell in an animal.

25. The polypeptide composition of claim 20, further comprising a pharmaceutically acceptable excipient.

26. A method of selectively decreasing potassium channel activity in a lymphocyte T-cell, comprising contacting said cell with an amount of a polypeptide composition of claim 20 effective to selectively decrease said channel activity.

27. The method of claim 26, wherein said channel comprises a homotetramer of Kv1.3 subunits.

28. The composition of claim 20 which selectively inhibits T-cell Kv1.3 lymphocyte channel activity, said composition characterized as a modified *Stichodactyla helianthus* polypeptide that interacts with amino acid residue His404, Asp402 or Tyr400 in said T-cell lymphocyte channel.

29. A method of attenuating calcium signaling pathway in a T-lymphocyte comprising contacting said T-lymphocyte with the composition of claim 20 in an amount sufficient to interact with a Kv1.3 channel.

30. A method of selectively decreasing potassium channel activity in a lymphocyte T-cell, comprising contacting said cell with an amount of a polypeptide composition effective to selectively decrease said channel activity, wherein said composition comprises a polypeptide having diaminopropionic acid substituted for lysine at position 22 of SEQ ID NO:1.

31. A method of suppressing T-cell activation in the immune system of an animal, comprising contacting a population of T-cells with a polypeptide, that comprises the amino acid sequence of SEQ ID NO:1, modified at residues Arg11 and Lys22 with an amino acid substitution.

32. The method of claim 31, wherein said T-cell is a mammalian T-cell.

33. The method of claim 32, wherein said mammalian T-cell is a human T-cell.

34. The method of claim 31, wherein said T-cell activation is caused by an immune response in said animal.

35. The method of claim 34, wherein said immune response is the result of heterologous organ rejection or an autoimmune disease.

36. The method of claim 35, wherein said organ is a heart, a lung, a liver, a kidney or a pancreas.

37. The method of claim 31, wherein said T-cell activation is from psoriasis.

38. The method of claim 31, wherein said T-cells are contacted with said polypeptide administered by injection or ingestion of said polypeptide into said animal.

39. A composition which selectively inhibits T-cell Kv1.3 lymphocyte channel activity wherein said composition comprises a polypeptide having a distinct amino substitution at amino acid position Arg11 of SEQ ID NO:1 wherein said substitution is selected from the group consisting of p-azidophenalanine, norleucine, ornithine, homocitrulline, diaminopimelic acid, cyclohexlalanine, p-benzoylphenylalanine and p-aminophenylalanine.

40. A composition comprising a polypeptide having the amino acid sequence of SEQ ID NO:1 wherein Lys at position 22 is substituted with diaminopimelic acid.

41. A polypeptide comprising the amino acid sequence of SEQ ID NO:56.

42. A method of suppressing T-cell activation in the immune system of an animal comprising contacting a population of T-cells with a polypeptide that comprises the amino acid sequence of SEQ ID NO:1 wherein diaminopropionic acid replaces lysine at position 22.

* * * * *

UNITED STATES PATENT AND TRADEMARK OFFICE
CERTIFICATE OF CORRECTION

PATENT NO.   : 6,077,680
DATED        : June 20, 2000
INVENTOR(S)  : Kern et al.

It is certified that error appears in the above-identified patent and that said Letters Patent is hereby corrected as shown below:

On the title page, item [73], line 2, delete "Ing.," and insert the following therefor: -- Inc., --

In claim 1, column 123, line 30, delete "diaminopinielic", and insert the following thereof: --diaminopimelic --.

Signed and Sealed this

Twenty-seventh Day of March, 2001

Attest:

NICHOLAS P. GODICI

Attesting Officer

Acting Director of the United States Patent and Trademark Office

SEQUENCE LISTING (1) GENERAL INFORMATION:

(iii) NUMBER OF SEQUENCES: 61

(2) INFORMATION FOR SEQ ID NO:1:

(i) SEQUENCE CHARACTERISTICS:
      (A) LENGTH: 35 amino acids
      (B) TYPE: amino acid
      (C) STRANDEDNESS:
      (D) TOPOLOGY: linear (xi) SEQUENCE DESCRIPTION: SEQ ID NO:1:

```
Arg Ser Cys Ile Asp Thr Ile Pro Lys Ser Arg Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35
```

(2) INFORMATION FOR SEQ ID NO:2:

(i) SEQUENCE CHARACTERISTICS:
        (A) LENGTH: 34 amino acids
        (B) TYPE: amino acid
        (C) STRANDEDNESS:
        (D) TOPOLOGY: linear (ix) FEATURE:
        (A) NAME/KEY: Modified-site
        (B) LOCATION: 18
        (D) OTHER INFORMATION: /note= "X=N-acetyl histidine"

(xi) SEQUENCE DESCRIPTION: SEQ ID NO:2:

```
Ser Cys Ile Asp Thr Ile Pro Lys Ser Arg Cys Thr Ala Phe Gln Cys
1               5                   10                  15

Lys Xaa Ser Met Lys Tyr Arg Leu Ser Phe Cys Arg Lys Thr Cys Gly
            20                  25                  30

Thr Cys
```

(2) INFORMATION FOR SEQ ID NO:3:

(i) SEQUENCE CHARACTERISTICS:
        (A) LENGTH: 33 amino acids
        (B) TYPE: amino acid
        (C) STRANDEDNESS:
        (D) TOPOLOGY: linear (xi) SEQUENCE DESCRIPTION: SEQ ID NO:3:

```
Cys Ile Asp Thr Ile Pro Lys Ser Arg Cys Thr Ala Phe Gln Cys Lys
1               5                   10                  15

His Ser Met Lys Tyr Arg Leu Ser Phe Cys Arg Lys Thr Cys Gly Thr
            20                  25                  30

Cys
```

(2) INFORMATION FOR SEQ ID NO:4:

(i) SEQUENCE CHARACTERISTICS:
        (A) LENGTH: 35 amino acids
        (B) TYPE: amino acid
        (C) STRANDEDNESS:
        (D) TOPOLOGY: linear (xi) SEQUENCE DESCRIPTION: SEQ ID NO:4:

```
Arg Ser Cys Ile Asp Thr Ile Pro Lys Ser Glu Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35
```

(2) INFORMATION FOR SEQ ID NO:5:

(i) SEQUENCE CHARACTERISTICS:
        (A) LENGTH: 35 amino acids
        (B) TYPE: amino acid
        (C) STRANDEDNESS:

(D) TOPOLOGY: linear (xi) SEQUENCE DESCRIPTION: SEQ ID NO:5:

Arg Ser Cys Ile Asp Thr Ile Pro Lys Ser Arg Cys Thr Ala Phe Glu
1               5                   10                  15

Cys Lys His Ser Met Lys Tyr Arg Leu Ser Phe Cys Arg Lys Thr Cys
                20                  25                  30

Gly Thr Cys
        35

(2) INFORMATION FOR SEQ ID NO:6:

(i) SEQUENCE CHARACTERISTICS:
        (A) LENGTH: 35 amino acids
        (B) TYPE: amino acid
        (C) STRANDEDNESS:
        (D) TOPOLOGY: linear (xi) SEQUENCE DESCRIPTION: SEQ ID NO:6:

Arg Ser Cys Ile Asp Thr Ile Pro Lys Ser Arg Cys Thr Ala Phe Gln
1               5                   10                  15

Cys Lys Lys Ser Met Lys Tyr Arg Leu Ser Phe Cys Arg Lys Thr Cys
                20                  25                  30

Gly Thr Cys
        35

(2) INFORMATION FOR SEQ ID NO:7:

(i) SEQUENCE CHARACTERISTICS:
        (A) LENGTH: 35 amino acids
        (B) TYPE: amino acid
        (C) STRANDEDNESS:
        (D) TOPOLOGY: linear (xi) SEQUENCE DESCRIPTION: SEQ ID NO:7:

Arg Ser Cys Ile Asp Thr Ile Pro Lys Ser Arg Cys Thr Ala Phe Gln
1               5                   10                  15

Cys Lys His Ser Met Glu Tyr Arg Leu Ser Phe Cys Arg Lys Thr Cys
                20                  25                  30

Gly Thr Cys
        35

(2) INFORMATION FOR SEQ ID NO:8:

(i) SEQUENCE CHARACTERISTICS:
        (A) LENGTH: 35 amino acids
        (B) TYPE: amino acid
        (C) STRANDEDNESS:
        (D) TOPOLOGY: linear (ix) FEATURE:
        (A) NAME/KEY: Modified-site
        (B) LOCATION: 23
        (D) OTHER INFORMATION: /note= "X=cyclohexylalanine"

(xi) SEQUENCE DESCRIPTION: SEQ ID NO:8:

Arg Ser Cys Ile Asp Thr Ile Pro Lys Ser Arg Cys Thr Ala Phe Gln
1               5                   10                  15

Cys Lys His Ser Met Lys Xaa Arg Leu Ser Phe Cys Arg Lys Thr Cys
                20                  25                  30

Gly Thr Cys
        35

(2) INFORMATION FOR SEQ ID NO:9:

(i) SEQUENCE CHARACTERISTICS:
        (A) LENGTH: 35 amino acids
        (B) TYPE: amino acid
        (C) STRANDEDNESS:
        (D) TOPOLOGY: linear (ix) FEATURE:
        (A) NAME/KEY: Modified-site
        (B) LOCATION: 27
        (D) OTHER INFORMATION: /note= "X=cyclohexylalanine"

(xi) SEQUENCE DESCRIPTION: SEQ ID NO:9:

```
Arg Ser Cys Ile Asp Thr Ile Pro Lys Ser Arg Cys Thr Ala Phe Gln
1               5                   10                  15

Cys Lys His Ser Met Lys Tyr Arg Leu Ser Xaa Cys Arg Lys Thr Cys
            20                  25                  30

Gly Thr Cys
        35
```

(2) INFORMATION FOR SEQ ID NO:10:

(i) SEQUENCE CHARACTERISTICS:
        (A) LENGTH: 35 amino acids
        (B) TYPE: amino acid
        (C) STRANDEDNESS:
        (D) TOPOLOGY: linear (xi) SEQUENCE DESCRIPTION: SEQ ID NO:10:

```
Arg Ser Cys Ala Asp Thr Ile Pro Lys Ser Arg Cys Thr Ala Ala Gln
1               5                   10                  15

Cys Lys His Ser Met Lys Tyr Arg Leu Ser Phe Cys Arg Lys Thr Cys
            20                  25                  30

Gly Thr Cys
        35
```

(2) INFORMATION FOR SEQ ID NO:11:

(i) SEQUENCE CHARACTERISTICS:
        (A) LENGTH: 35 amino acids
        (B) TYPE: amino acid
        (C) STRANDEDNESS:
        (D) TOPOLOGY: linear (xi) SEQUENCE DESCRIPTION: SEQ ID NO:11:

```
Arg Ser Cys Ile Asp Thr Ile Pro Lys Ser Arg Cys Thr Ala Ala Gln
1               5                   10                  15

Cys Lys His Ser Met Lys Tyr Arg Ala Ser Phe Cys Arg Lys Thr Cys
            20                  25                  30

Gly Thr Cys
        35
```

(2) INFORMATION FOR SEQ ID NO:12:

(i) SEQUENCE CHARACTERISTICS:
        (A) LENGTH: 35 amino acids
        (B) TYPE: amino acid
        (C) STRANDEDNESS:
        (D) TOPOLOGY: linear (xi) SEQUENCE DESCRIPTION: SEQ ID NO:12:

```
Arg Ser Cys Ala Asp Thr Ile Pro Lys Ser Arg Cys Thr Ala Ala Gln
1               5                   10                  15

Cys Lys His Ser Met Lys Tyr Arg Ala Ser Phe Cys Arg Lys Thr Cys
```

```
                20                  25                  30
Gly Thr Cys
         35

(2) INFORMATION FOR SEQ ID NO:13:

(i) SEQUENCE CHARACTERISTICS:
        (A) LENGTH: 35 amino acids
        (B) TYPE: amino acid
        (C) STRANDEDNESS:
        (D) TOPOLOGY: linear (xi) SEQUENCE DESCRIPTION: SEQ ID NO:13:

Ser Ser Cys Ile Asp Thr Ile Pro Lys Ser Arg Cys Thr Ala Phe Gln
1               5                  10                  15

Cys Lys His Ser Met Lys Tyr Arg Leu Ser Phe Cys Arg Lys Thr Cys
                20                  25                  30

Gly Thr Cys
         35

(2) INFORMATION FOR SEQ ID NO:14:

(i) SEQUENCE CHARACTERISTICS:
        (A) LENGTH: 35 amino acids
        (B) TYPE: amino acid
        (C) STRANDEDNESS:
        (D) TOPOLOGY: linear (xi) SEQUENCE DESCRIPTION: SEQ ID NO:14:

Arg Ser Cys Ile Asp Thr Ile Pro Gln Ser Arg Cys Thr Ala Phe Gln
1               5                  10                  15

Cys Lys His Ser Met Lys Tyr Arg Leu Ser Phe Cys Arg Lys Thr Cys
                20                  25                  30

Gly Thr Cys
         35

(2) INFORMATION FOR SEQ ID NO:15:

(i) SEQUENCE CHARACTERISTICS:
        (A) LENGTH: 35 amino acids
        (B) TYPE: amino acid
        (C) STRANDEDNESS:
        (D) TOPOLOGY: linear (xi) SEQUENCE DESCRIPTION: SEQ ID NO:15:

Arg Ser Cys Ile Asp Thr Ile Pro Lys Ser Gln Cys Thr Ala Phe Gln
1               5                  10                  15

Cys Lys His Ser Met Lys Tyr Arg Leu Ser Phe Cys Arg Lys Thr Cys
                20                  25                  30

Gly Thr Cys
         35

(2) INFORMATION FOR SEQ ID NO:16:

(i) SEQUENCE CHARACTERISTICS:
        (A) LENGTH: 35 amino acids
        (B) TYPE: amino acid
        (C) STRANDEDNESS:
        (D) TOPOLOGY: linear (xi) SEQUENCE DESCRIPTION: SEQ ID NO:16:

Arg Ser Cys Ile Asp Thr Ile Pro Lys Ser Arg Cys Thr Ala Ala Gln
1               5                  10                  15
```

```
Cys Lys His Ser Met Lys Tyr Arg Leu Ser Phe Cys Arg Lys Thr Cys
             20                  25                  30

Gly Thr Cys
         35
```

(2) INFORMATION FOR SEQ ID NO:17:

(i) SEQUENCE CHARACTERISTICS:
        (A) LENGTH: 35 amino acids
        (B) TYPE: amino acid
        (C) STRANDEDNESS:
        (D) TOPOLOGY: linear (xi) SEQUENCE DESCRIPTION: SEQ ID NO:17:

```
Arg Ser Cys Ile Asp Thr Ile Pro Lys Ser Arg Cys Thr Ala Trp Gln
1                5                  10                  15

Cys Lys His Ser Met Lys Tyr Arg Leu Ser Phe Cys Arg Lys Thr Cys
             20                  25                  30

Gly Thr Cys
         35
```

(2) INFORMATION FOR SEQ ID NO:18:

(i) SEQUENCE CHARACTERISTICS:
        (A) LENGTH: 35 amino acids
        (B) TYPE: amino acid
        (C) STRANDEDNESS:
        (D) TOPOLOGY: linear (xi) SEQUENCE DESCRIPTION: SEQ ID NO:18:

```
Arg Ser Cys Ile Asp Thr Ile Pro Lys Ser Arg Cys Thr Ala Phe Gln
1                5                  10                  15

Cys Ala His Ser Met Lys Tyr Arg Leu Ser Phe Cys Arg Lys Thr Cys
             20                  25                  30

Gly Thr Cys
         35
```

(2) INFORMATION FOR SEQ ID NO:19:

(i) SEQUENCE CHARACTERISTICS:
        (A) LENGTH: 35 amino acids
        (B) TYPE: amino acid
        (C) STRANDEDNESS:
        (D) TOPOLOGY: linear (ix) FEATURE:
        (A) NAME/KEY: Modified-site
        (B) LOCATION: 21
        (D) OTHER INFORMATION: /note= "X=norleucine"

(xi) SEQUENCE DESCRIPTION: SEQ ID NO:19:

```
Arg Ser Cys Ile Asp Thr Ile Pro Lys Ser Arg Cys Thr Ala Phe Gln
1                5                  10                  15

Cys Lys His Ser Xaa Lys Tyr Arg Leu Ser Phe Cys Arg Lys Thr Cys
             20                  25                  30

Gly Thr Cys
         35
```

(2) INFORMATION FOR SEQ ID NO:20:

(i) SEQUENCE CHARACTERISTICS:
        (A) LENGTH: 35 amino acids
        (B) TYPE: amino acid
        (C) STRANDEDNESS:
        (D) TOPOLOGY: linear (xi) SEQUENCE DESCRIPTION: SEQ ID NO:20:

Arg Ser Cys Ile Asp Thr Ile Pro Lys Ser Arg Cys Thr Ala Phe Gln
1               5                   10                  15

Cys Lys His Ser Met Ala Tyr Arg Leu Ser Phe Cys Arg Lys Thr Cys
            20                  25                  30

Gly Thr Cys
        35

(2) INFORMATION FOR SEQ ID NO:21:

(i) SEQUENCE CHARACTERISTICS:
        (A) LENGTH: 35 amino acids
        (B) TYPE: amino acid
        (C) STRANDEDNESS:
        (D) TOPOLOGY: linear (ix) FEATURE:
        (A) NAME/KEY: Modified-site
        (B) LOCATION: 22
        (D) OTHER INFORMATION: /note= "X=norleucine"

(xi) SEQUENCE DESCRIPTION: SEQ ID NO:21:

Arg Ser Cys Ile Asp Thr Ile Pro Lys Ser Arg Cys Thr Ala Phe Gln
1               5                   10                  15

Cys Lys His Ser Met Xaa Tyr Arg Leu Ser Phe Cys Arg Lys Thr Cys
            20                  25                  30

Gly Thr Cys
        35

(2) INFORMATION FOR SEQ ID NO:22:

(i) SEQUENCE CHARACTERISTICS:
        (A) LENGTH: 35 amino acids
        (B) TYPE: amino acid
        (C) STRANDEDNESS:
        (D) TOPOLOGY: linear (ix) FEATURE:
        (A) NAME/KEY: Modified-site
        (B) LOCATION: 22
        (D) OTHER INFORMATION: /note= "X=ornithine"

(xi) SEQUENCE DESCRIPTION: SEQ ID NO:22:

Arg Ser Cys Ile Asp Thr Ile Pro Lys Ser Arg Cys Thr Ala Phe Gln
1               5                   10                  15

Cys Lys His Ser Met Xaa Tyr Arg Leu Ser Phe Cys Arg Lys Thr Cys
            20                  25                  30

Gly Thr Cys
        35

(2) INFORMATION FOR SEQ ID NO:23:

(i) SEQUENCE CHARACTERISTICS:
        (A) LENGTH: 35 amino acids
        (B) TYPE: amino acid
        (C) STRANDEDNESS:
        (D) TOPOLOGY: linear (ix) FEATURE:
        (A) NAME/KEY: Modified-site
        (B) LOCATION: 22
        (D) OTHER INFORMATION: /note= "X=homocitrulline"

(xi) SEQUENCE DESCRIPTION: SEQ ID NO:23:

Arg Ser Cys Ile Asp Thr Ile Pro Lys Ser Arg Cys Thr Ala Phe Gln

```
1               5              10              15
Cys Lys His Ser Met Xaa Tyr Arg Leu Ser Phe Cys Arg Lys Thr Cys
            20              25              30

Gly Thr Cys
        35

(2) INFORMATION FOR SEQ ID NO:24:

(i) SEQUENCE CHARACTERISTICS:
        (A) LENGTH: 35 amino acids
        (B) TYPE: amino acid
        (C) STRANDEDNESS:
        (D) TOPOLOGY: linear (xi) SEQUENCE DESCRIPTION: SEQ ID NO:24:

Arg Ser Cys Ile Asp Thr Ile Pro Lys Ser Arg Cys Thr Ala Phe Gln
1               5              10              15

Cys Arg His Ser Met Arg Tyr Arg Leu Ser Phe Cys Arg Lys Thr Cys
            20              25              30

Gly Thr Cys
        35

(2) INFORMATION FOR SEQ ID NO:25:

(i) SEQUENCE CHARACTERISTICS:
        (A) LENGTH: 35 amino acids
        (B) TYPE: amino acid
        (C) STRANDEDNESS:
        (D) TOPOLOGY: linear (xi) SEQUENCE DESCRIPTION: SEQ ID NO:25:

Arg Ser Cys Ile Asp Thr Ile Pro Lys Ser Arg Cys Thr Ala Phe Gln
1               5              10              15

Cys Lys His Ser Met Lys Phe Arg Leu Ser Phe Cys Arg Lys Thr Cys
            20              25              30

Gly Thr Cys
        35

(2) INFORMATION FOR SEQ ID NO:26:

(i) SEQUENCE CHARACTERISTICS:
        (A) LENGTH: 35 amino acids
        (B) TYPE: amino acid
        (C) STRANDEDNESS:
        (D) TOPOLOGY: linear (ix) FEATURE:
        (A) NAME/KEY: Modified-site
        (B) LOCATION: 23
        (D) OTHER INFORMATION: /note= "X=nitrophenylalanine"

(xi) SEQUENCE DESCRIPTION: SEQ ID NO:26:

Arg Ser Cys Ile Asp Thr Ile Pro Lys Ser Arg Cys Thr Ala Phe Gln
1               5              10              15

Cys Lys His Ser Met Lys Xaa Arg Leu Ser Phe Cys Arg Lys Thr Cys
            20              25              30

Gly Thr Cys
        35

(2) INFORMATION FOR SEQ ID NO:27:

(i) SEQUENCE CHARACTERISTICS:
        (A) LENGTH: 35 amino acids
        (B) TYPE: amino acid
```

(C) STRANDEDNESS:
            (D) TOPOLOGY: linear (ix) FEATURE:
            (A) NAME/KEY: Modified-site
            (B) LOCATION: 23
            (D) OTHER INFORMATION: /note= "X=aminophenylalanine"

(xi) SEQUENCE DESCRIPTION: SEQ ID NO:27:

Arg Ser Cys Ile Asp Thr Ile Pro Lys Ser Arg Cys Thr Ala Phe Gln
1               5                   10                  15

Cys Lys His Ser Met Lys Xaa Arg Leu Ser Phe Cys Arg Lys Thr Cys
                20                  25                  30

Gly Thr Cys
        35

(2) INFORMATION FOR SEQ ID NO:28:

(i) SEQUENCE CHARACTERISTICS:
            (A) LENGTH: 35 amino acids
            (B) TYPE: amino acid
            (C) STRANDEDNESS:
            (D) TOPOLOGY: linear (xi) SEQUENCE DESCRIPTION: SEQ ID NO:28:

Arg Ser Cys Ile Asp Thr Ile Pro Lys Ser Arg Cys Thr Ala Phe Gln
1               5                   10                  15

Cys Lys His Ser Met Lys Tyr Ala Leu Ser Phe Cys Arg Lys Thr Cys
                20                  25                  30

Gly Thr Cys
        35

(2) INFORMATION FOR SEQ ID NO:29:

(i) SEQUENCE CHARACTERISTICS:
            (A) LENGTH: 35 amino acids
            (B) TYPE: amino acid
            (C) STRANDEDNESS:
            (D) TOPOLOGY: linear (xi) SEQUENCE DESCRIPTION: SEQ ID NO:29:

Ala Ser Cys Ile Asp Thr Ile Pro Lys Ser Arg Cys Thr Ala Phe Gln
1               5                   10                  15

Cys Lys His Ser Met Lys Tyr Arg Leu Ser Phe Cys Arg Lys Thr Cys
                20                  25                  30

Gly Thr Cys
        35

(2) INFORMATION FOR SEQ ID NO:30:

(i) SEQUENCE CHARACTERISTICS:
            (A) LENGTH: 35 amino acids
            (B) TYPE: amino acid
            (C) STRANDEDNESS:
            (D) TOPOLOGY: linear (xi) SEQUENCE DESCRIPTION: SEQ ID NO:30:

Arg Ala Cys Ile Asp Thr Ile Pro Lys Ser Arg Cys Thr Ala Phe Gln
1               5                   10                  15

Cys Lys His Ser Met Lys Tyr Arg Leu Ser Phe Cys Arg Lys Thr Cys
                20                  25                  30

Gly Thr Cys
        35

(2) INFORMATION FOR SEQ ID NO:31:

(i) SEQUENCE CHARACTERISTICS:
        (A) LENGTH: 35 amino acids
        (B) TYPE: amino acid
        (C) STRANDEDNESS:
        (D) TOPOLOGY: linear (xi) SEQUENCE DESCRIPTION: SEQ ID NO:31:

```
Arg Ser Cys Ala Asp Thr Ile Pro Lys Ser Arg Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35
```

(2) INFORMATION FOR SEQ ID NO:32:

(i) SEQUENCE CHARACTERISTICS:
        (A) LENGTH: 35 amino acids
        (B) TYPE: amino acid
        (C) STRANDEDNESS:
        (D) TOPOLOGY: linear (xi) SEQUENCE DESCRIPTION: SEQ ID NO:32:

```
Arg Ser Cys Ile Ala Thr Ile Pro Lys Ser Arg Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35
```

(2) INFORMATION FOR SEQ ID NO:33:

(i) SEQUENCE CHARACTERISTICS:
        (A) LENGTH: 35 amino acids
        (B) TYPE: amino acid
        (C) STRANDEDNESS:
        (D) TOPOLOGY: linear (xi) SEQUENCE DESCRIPTION: SEQ ID NO:33:

```
Arg Ser Cys Ile Asp Ala Ile Pro Lys Ser Arg Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35
```

(2) INFORMATION FOR SEQ ID NO:34:

(i) SEQUENCE CHARACTERISTICS:
        (A) LENGTH: 35 amino acids
        (B) TYPE: amino acid
        (C) STRANDEDNESS:
        (D) TOPOLOGY: linear (xi) SEQUENCE DESCRIPTION: SEQ ID NO:34:

```
Arg Ser Cys Ile Asp Thr Ala Pro Lys Ser Arg Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35
```

(2) INFORMATION FOR SEQ ID NO:35:

(i) SEQUENCE CHARACTERISTICS:
  (A) LENGTH: 35 amino acids
  (B) TYPE: amino acid
  (C) STRANDEDNESS:
  (D) TOPOLOGY: linear (xi) SEQUENCE DESCRIPTION: SEQ ID NO:35:

```
Arg Ser Cys Ile Asp Thr Ile Ala Lys Ser Arg Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35
```

(2) INFORMATION FOR SEQ ID NO:36:

(i) SEQUENCE CHARACTERISTICS:
  (A) LENGTH: 35 amino acids
  (B) TYPE: amino acid
  (C) STRANDEDNESS:
  (D) TOPOLOGY: linear (xi) SEQUENCE DESCRIPTION: SEQ ID NO:36:

```
Arg Ser Cys Ile Asp Thr Ile Pro Ala Ser Arg Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35
```

(2) INFORMATION FOR SEQ ID NO:37:

(i) SEQUENCE CHARACTERISTICS:
  (A) LENGTH: 35 amino acids
  (B) TYPE: amino acid
  (C) STRANDEDNESS:
  (D) TOPOLOGY: linear (xi) SEQUENCE DESCRIPTION: SEQ ID NO:37:

```
Arg Ser Cys Ile Asp Thr Ile Pro Lys Ala Arg Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35
```

(2) INFORMATION FOR SEQ ID NO:38:

(i) SEQUENCE CHARACTERISTICS:
  (A) LENGTH: 35 amino acids
  (B) TYPE: amino acid
  (C) STRANDEDNESS:
  (D) TOPOLOGY: linear (xi) SEQUENCE DESCRIPTION: SEQ ID NO:38:

```
Arg Ser Cys Ile Asp Thr Ile Pro Lys Ser Ala Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
```

35

(2) INFORMATION FOR SEQ ID NO:39:

(i) SEQUENCE CHARACTERISTICS:
        (A) LENGTH: 35 amino acids
        (B) TYPE: amino acid
        (C) STRANDEDNESS:
        (D) TOPOLOGY: linear (xi) SEQUENCE DESCRIPTION: SEQ ID NO:39:

Arg Ser Cys Ile Asp Thr Ile Pro Lys Ser Arg Cys Ala Ala Phe Gln
1               5                  10                  15

Cys Lys His Ser Met Lys Tyr Arg Leu Ser Phe Cys Arg Lys Thr Cys
            20                  25                  30

Gly Thr Cys
        35

(2) INFORMATION FOR SEQ ID NO:40:

(i) SEQUENCE CHARACTERISTICS:
        (A) LENGTH: 35 amino acids
        (B) TYPE: amino acid
        (C) STRANDEDNESS:
        (D) TOPOLOGY: linear (xi) SEQUENCE DESCRIPTION: SEQ ID NO:40:

Arg Ser Cys Ile Asp Thr Ile Pro Lys Ser Arg Cys Thr Ala Ala Gln
1               5                  10                  15

Cys Lys His Ser Met Lys Tyr Arg Leu Ser Phe Cys Arg Lys Thr Cys
            20                  25                  30

Gly Thr Cys
        35

(2) INFORMATION FOR SEQ ID NO:41:

(i) SEQUENCE CHARACTERISTICS:
        (A) LENGTH: 35 amino acids
        (B) TYPE: amino acid
        (C) STRANDEDNESS:
        (D) TOPOLOGY: linear (xi) SEQUENCE DESCRIPTION: SEQ ID NO:41:

Arg Ser Cys Ile Asp Thr Ile Pro Lys Ser Arg Cys Thr Ala Phe Ala
1               5                  10                  15

Cys Lys His Ser Met Lys Tyr Arg Leu Ser Phe Cys Arg Lys Thr Cys
            20                  25                  30

Gly Thr Cys
        35

(2) INFORMATION FOR SEQ ID NO:42:

(i) SEQUENCE CHARACTERISTICS:
        (A) LENGTH: 35 amino acids
        (B) TYPE: amino acid
        (C) STRANDEDNESS:
        (D) TOPOLOGY: linear (xi) SEQUENCE DESCRIPTION: SEQ ID NO:42:

Arg Ser Cys Ile Asp Thr Ile Pro Lys Ser Arg Cys Thr Ala Phe Gln
1               5                  10                  15

Cys Ala His Ser Met Lys Tyr Arg Leu Ser Phe Cys Arg Lys Thr Cys
            20                  25                  30

Gly Thr Cys
    35

(2) INFORMATION FOR SEQ ID NO:43:

(i) SEQUENCE CHARACTERISTICS:
        (A) LENGTH: 35 amino acids
        (B) TYPE: amino acid
        (C) STRANDEDNESS:
        (D) TOPOLOGY: linear (xi) SEQUENCE DESCRIPTION: SEQ ID NO:43:

Arg Ser Cys Ile Asp Thr Ile Pro Lys Ser Arg Cys Thr Ala Phe Gln
1               5                   10                  15

Cys Lys Ala Ser Met Lys Tyr Arg Leu Ser Phe Cys Arg Lys Thr Cys
            20                  25                  30

Gly Thr Cys
    35

(2) INFORMATION FOR SEQ ID NO:44:

(i) SEQUENCE CHARACTERISTICS:
        (A) LENGTH: 35 amino acids
        (B) TYPE: amino acid
        (C) STRANDEDNESS:
        (D) TOPOLOGY: linear (xi) SEQUENCE DESCRIPTION: SEQ ID NO:44:

Arg Ser Cys Ile Asp Thr Ile Pro Lys Ser Arg Cys Thr Ala Phe Gln
1               5                   10                  15

Cys Lys His Ala Met Lys Tyr Arg Leu Ser Phe Cys Arg Lys Thr Cys
            20                  25                  30

Gly Thr Cys
    35

(2) INFORMATION FOR SEQ ID NO:45:

(i) SEQUENCE CHARACTERISTICS:
        (A) LENGTH: 35 amino acids
        (B) TYPE: amino acid
        (C) STRANDEDNESS:
        (D) TOPOLOGY: linear (xi) SEQUENCE DESCRIPTION: SEQ ID NO:45:

Arg Ser Cys Ile Asp Thr Ile Pro Lys Ser Arg Cys Thr Ala Phe Gln
1               5                   10                  15

Cys Lys His Ser Ala Lys Tyr Arg Leu Ser Phe Cys Arg Lys Thr Cys
            20                  25                  30

Gly Thr Cys
    35

(2) INFORMATION FOR SEQ ID NO:46:

(i) SEQUENCE CHARACTERISTICS:
        (A) LENGTH: 35 amino acids
        (B) TYPE: amino acid
        (C) STRANDEDNESS:
        (D) TOPOLOGY: linear (xi) SEQUENCE DESCRIPTION: SEQ ID NO:46:

Arg Ser Cys Ile Asp Thr Ile Pro Lys Ser Arg Cys Thr Ala Phe Gln
1               5                   10                  15

Cys Lys His Ser Met Ala Tyr Arg Leu Ser Phe Cys Arg Lys Thr Cys
            20                  25                  30

Gly Thr Cys
    35

(2) INFORMATION FOR SEQ ID NO:47:

(i) SEQUENCE CHARACTERISTICS:
        (A) LENGTH: 35 amino acids
        (B) TYPE: amino acid
        (C) STRANDEDNESS:
        (D) TOPOLOGY: linear (xi) SEQUENCE DESCRIPTION: SEQ ID NO:47:

Arg Ser Cys Ile Asp Thr Ile Pro Lys Ser Arg Cys Thr Ala Phe Gln
1               5                   10                  15

Cys Lys His Ser Met Lys Ala Arg Leu Ser Phe Cys Arg Lys Thr Cys
            20                  25                  30

Gly Thr Cys
    35

(2) INFORMATION FOR SEQ ID NO:48:

(i) SEQUENCE CHARACTERISTICS:
        (A) LENGTH: 35 amino acids
        (B) TYPE: amino acid
        (C) STRANDEDNESS:
        (D) TOPOLOGY: linear (xi) SEQUENCE DESCRIPTION: SEQ ID NO:48:

Arg Ser Cys Ile Asp Thr Ile Pro Lys Ser Arg Cys Thr Ala Phe Gln
1               5                   10                  15

Cys Lys His Ser Met Lys Tyr Ala Leu Ser Phe Cys Arg Lys Thr Cys
            20                  25                  30

Gly Thr Cys
    35

(2) INFORMATION FOR SEQ ID NO:49:

(i) SEQUENCE CHARACTERISTICS:
        (A) LENGTH: 35 amino acids
        (B) TYPE: amino acid
        (C) STRANDEDNESS:
        (D) TOPOLOGY: linear (xi) SEQUENCE DESCRIPTION: SEQ ID NO:49:

Arg Ser Cys Ile Asp Thr Ile Pro Lys Ser Arg Cys Thr Ala Phe Gln
1               5                   10                  15

Cys Lys His Ser Met Lys Tyr Arg Ala Ser Phe Cys Arg Lys Thr Cys
            20                  25                  30

Gly Thr Cys
    35

(2) INFORMATION FOR SEQ ID NO:50:

(i) SEQUENCE CHARACTERISTICS:
        (A) LENGTH: 35 amino acids
        (B) TYPE: amino acid
        (C) STRANDEDNESS:
        (D) TOPOLOGY: linear (xi) SEQUENCE DESCRIPTION: SEQ ID NO:50:

Arg Ser Cys Ile Asp Thr Ile Pro Lys Ser Arg Cys Thr Ala Phe Gln
1               5                   10                  15

Cys Lys His Ser Met Lys Tyr Arg Leu Ala Phe Cys Arg Lys Thr Cys

```
                   20                  25                  30

Gly Thr Cys
        35

(2) INFORMATION FOR SEQ ID NO:51:

(i) SEQUENCE CHARACTERISTICS:
        (A) LENGTH: 35 amino acids
        (B) TYPE: amino acid
        (C) STRANDEDNESS:
        (D) TOPOLOGY: linear (xi) SEQUENCE DESCRIPTION: SEQ ID NO:51:

Arg Ser Cys Ile Asp Thr Ile Pro Lys Ser Arg Cys Thr Ala Phe Gln
1               5                  10                  15

Cys Lys His Ser Met Lys Tyr Arg Leu Ser Ala Cys Arg Lys Thr Cys
                20                  25                  30

Gly Thr Cys
        35

(2) INFORMATION FOR SEQ ID NO:52:

(i) SEQUENCE CHARACTERISTICS:
        (A) LENGTH: 35 amino acids
        (B) TYPE: amino acid
        (C) STRANDEDNESS:
        (D) TOPOLOGY: linear (xi) SEQUENCE DESCRIPTION: SEQ ID NO:52:

Arg Ser Cys Ile Asp Thr Ile Pro Lys Ser Arg Cys Thr Ala Phe Gln
1               5                  10                  15

Cys Lys His Ser Met Lys Tyr Arg Leu Ser Phe Cys Ala Lys Thr Cys
                20                  25                  30

Gly Thr Cys
        35

(2) INFORMATION FOR SEQ ID NO:53:

(i) SEQUENCE CHARACTERISTICS:
        (A) LENGTH: 35 amino acids
        (B) TYPE: amino acid
        (C) STRANDEDNESS:
        (D) TOPOLOGY: linear (xi) SEQUENCE DESCRIPTION: SEQ ID NO:53:

Arg Ser Cys Ile Asp Thr Ile Pro Lys Ser Arg Cys Thr Ala Pro Gln
1               5                  10                  15

Cys Lys His Ser Met Lys Tyr Arg Leu Ser Phe Cys Arg Ala Thr Cys
                20                  25                  30

Gly Thr Cys
        35

(2) INFORMATION FOR SEQ ID NO:54:

(i) SEQUENCE CHARACTERISTICS:
        (A) LENGTH: 35 amino acids
        (B) TYPE: amino acid
        (C) STRANDEDNESS:
        (D) TOPOLOGY: linear (xi) SEQUENCE DESCRIPTION: SEQ ID NO:54:

Arg Ser Cys Ile Asp Thr Ile Pro Lys Ser Arg Cys Thr Ala Pro Gln
1               5                  10                  15
```

Cys Lys His Ser Met Lys Tyr Arg Leu Ser Phe Cys Arg Lys Ala Cys
            20                  25                  30

Gly Thr Cys
        35

(2) INFORMATION FOR SEQ ID NO:55:

(i) SEQUENCE CHARACTERISTICS:
        (A) LENGTH: 35 amino acids
        (B) TYPE: amino acid
        (C) STRANDEDNESS:
        (D) TOPOLOGY: linear (xi) SEQUENCE DESCRIPTION: SEQ ID NO:55:

Arg Ser Cys Ile Asp Thr Ile Pro Lys Ser Arg Cys Thr Ala Pro Gln
1               5                   10                  15

Cys Lys His Ser Met Lys Tyr Arg Leu Ser Phe Cys Arg Lys Thr Cys
            20                  25                  30

Gly Ala Cys
        35

(2) INFORMATION FOR SEQ ID NO:56:

(i) SEQUENCE CHARACTERISTICS:
        (A) LENGTH: 35 amino acids
        (B) TYPE: amino acid
        (C) STRANDEDNESS:
        (D) TOPOLOGY: linear (ix) FEATURE:
        (A) NAME/KEY: Modified-site
        (B) LOCATION: 22
        (D) OTHER INFORMATION: /note= "X=diaminopropionic acid"

(xi) SEQUENCE DESCRIPTION: SEQ ID NO:56:

Arg Ser Cys Ile Asp Thr Ile Pro Lys Ser Arg Cys Thr Ala Phe Gln
1               5                   10                  15

Cys Lys His Ser Met Xaa Tyr Arg Leu Ser Phe Cys Arg Lys Thr Cys
            20                  25                  30

Gly Thr Cys
        35

(2) INFORMATION FOR SEQ ID NO:57:

(i) SEQUENCE CHARACTERISTICS:
        (A) LENGTH: 35 amino acids
        (B) TYPE: amino acid
        (C) STRANDEDNESS:
        (D) TOPOLOGY: linear (ix) FEATURE:
        (A) NAME/KEY: Modified-site
        (B) LOCATION: 23
        (D) OTHER INFORMATION: /note= "X=benzoylphenylalanine"

(xi) SEQUENCE DESCRIPTION: SEQ ID NO:57:

Arg Ser Cys Ile Asp Thr Ile Pro Lys Ser Arg Cys Thr Ala Phe Gln
1               5                   10                  15

Cys Lys His Ser Met Lys Xaa Arg Leu Ser Phe Cys Arg Lys Thr Cys
            20                  25                  30

Gly Thr Cys
        35

(2) INFORMATION FOR SEQ ID NO:58:

(i) SEQUENCE CHARACTERISTICS:
    (A) LENGTH: 35 amino acids
    (B) TYPE: amino acid
    (C) STRANDEDNESS:
    (D) TOPOLOGY: linear (ix) FEATURE:
    (A) NAME/KEY: Modified-site
    (B) LOCATION: 1
    (D) OTHER INFORMATION: /note= "X=N-acetyl-arginine"

(xi) SEQUENCE DESCRIPTION: SEQ ID NO:58:

Xaa Ser Cys Ile Asp Thr Ile Pro Lys Ser Arg Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35

(2) INFORMATION FOR SEQ ID NO:59:

(i) SEQUENCE CHARACTERISTICS:
        (A) LENGTH: 35 amino acids
        (B) TYPE: amino acid
        (C) STRANDEDNESS:
        (D) TOPOLOGY: linear (ix) FEATURE:
        (A) NAME/KEY: Modified-site
        (B) LOCATION: 15
        (D) OTHER INFORMATION: /note= "X=azidophenylalanine"

(xi) SEQUENCE DESCRIPTION: SEQ ID NO:59:

Arg Ser Cys Ile Asp Thr Ile Pro Lys Ser Arg Cys Thr Ala Xaa Gln
1               5                   10                  15

Cys Lys His Ser Met Lys Tyr Arg Leu Ser Phe Cys Arg Lys Thr Cys
            20                  25                  30

Gly Thr Cys
        35

(2) INFORMATION FOR SEQ ID NO:60:

(i) SEQUENCE CHARACTERISTICS:
        (A) LENGTH: 35 amino acids
        (B) TYPE: amino acid
        (C) STRANDEDNESS:
        (D) TOPOLOGY: linear (ix) FEATURE:
        (A) NAME/KEY: Disulfide-bond
        (B) LOCATION: 3..35

(ix) FEATURE:
        (A) NAME/KEY: Disulfide-bond
        (B) LOCATION: 12..17

(xi) SEQUENCE DESCRIPTION: SEQ ID NO:60:

Arg Ser Cys Ile Asp Thr Ile Pro Lys Ser Arg Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35

(2) INFORMATION FOR SEQ ID NO:61:

(i) SEQUENCE CHARACTERISTICS:

```
        (A) LENGTH: 35 amino acids
        (B) TYPE: amino acid
        (C) STRANDEDNESS:
        (D) TOPOLOGY: linear (ix) FEATURE:
        (A) NAME/KEY: Disulfide-bond
        (B) LOCATION: 3..35

(xi) SEQUENCE DESCRIPTION: SEQ ID NO:61:

Arg Ser Cys Ile Asp Thr Ile Pro Lys Ser Arg Xaa Thr Ala Phe Gln
1               5                   10                  15

Xaa Lys His Ser Met Lys Tyr Arg Leu Ser Phe Cys Arg Lys Thr Cys
            20                  25                  30

Gly Thr Cys
        35
```